United States Patent
Udupa et al.

(10) Patent No.: US 11,232,319 B2
(45) Date of Patent: Jan. 25, 2022

(54) APPLICATIONS OF AUTOMATIC ANATOMY RECOGNITION IN MEDICAL TOMOGRAPHIC IMAGERY BASED ON FUZZY ANATOMY MODELS

(71) Applicant: The Trustees of The University of Pennsylvania, Philadelphia, PA (US)

(72) Inventors: Jayaram K. Udupa, Philadelphia, PA (US); Dewey Odhner, Horsham, PA (US); Drew A. Torigian, Philadelphia, PA (US); Yubing Tong, Norwood, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 82 days.

(21) Appl. No.: 15/311,675

(22) PCT Filed: May 14, 2015

(86) PCT No.: PCT/US2015/030833
§ 371 (c)(1),
(2) Date: Nov. 16, 2016

(87) PCT Pub. No.: WO2015/175806
PCT Pub. Date: Nov. 19, 2015

(65) Prior Publication Data
US 2017/0091574 A1    Mar. 30, 2017

Related U.S. Application Data

(60) Provisional application No. 62/116,222, filed on Feb. 13, 2015, provisional application No. 61/994,494, filed on May 16, 2014.

(51) Int. Cl.
*G06K 9/46* (2006.01)
*G06T 7/11* (2017.01)
(Continued)

(52) U.S. Cl.
CPC ......... *G06K 9/4638* (2013.01); *A61N 5/1039* (2013.01); *G06T 7/0012* (2013.01);
(Continued)

(58) Field of Classification Search
CPC ..................... A61N 5/103; G06K 2209/051
See application file for complete search history.

(56) References Cited

U.S. PATENT DOCUMENTS

| | | | | |
|---|---|---|---|---|
| 5,926,568 A | * | 7/1999 | Chaney | G06K 9/6206 382/128 |
| 8,135,111 B2 | * | 3/2012 | Jaffray | A61B 6/508 378/65 |

(Continued)

OTHER PUBLICATIONS

J. Udupa et al, "Body-wide hierarchical fuzzy modeling, recognition, and delineation of anatomy in medical images", 2014, Medical Image Analysis 18 (2014), p. 752-771.*

(Continued)

*Primary Examiner* — Gandhi Thirugnanam
(74) *Attorney, Agent, or Firm* — BakerHostetler

(57) ABSTRACT

A computerized method of providing automatic anatomy recognition (AAR) includes gathering image data from patient image sets, formulating precise definitions of each body region and organ and delineating them following the definitions, building hierarchical fuzzy anatomy models of organs for each body region, recognizing and locating organs in given images by employing the hierarchical models, and delineating the organs following the hierarchy. The method may be applied, for example, to body regions including the thorax, abdomen and neck regions to identify organs.

21 Claims, 18 Drawing Sheets

(51) Int. Cl.
 G06T 7/143 (2017.01)
 G06T 7/136 (2017.01)
 G06T 7/70 (2017.01)
 A61N 5/10 (2006.01)
 G06T 7/00 (2017.01)

(52) U.S. Cl.
 CPC ............... *G06T 7/11* (2017.01); *G06T 7/136* (2017.01); *G06T 7/143* (2017.01); *G06T 7/70* (2017.01); *A61N 5/103* (2013.01); *G06K 2209/051* (2013.01); *G06T 2207/10081* (2013.01); *G06T 2207/10088* (2013.01); *G06T 2207/20016* (2013.01); *G06T 2207/20128* (2013.01); *G06T 2207/30004* (2013.01)

(56) References Cited

U.S. PATENT DOCUMENTS

| | | | | |
|---|---|---|---|---|
| 11,080,336 | B2* | 8/2021 | Van Dusen | G06Q 30/0279 |
| 2004/0034301 | A1* | 2/2004 | Falco | A61N 5/1049 600/427 |
| 2006/0104494 | A1* | 5/2006 | Collins | G06T 7/0012 382/128 |
| 2007/0003123 | A1* | 1/2007 | Fu | A61N 5/1049 382/131 |
| 2008/0025638 | A1* | 1/2008 | Chen | G06T 7/35 382/284 |
| 2008/0287821 | A1* | 11/2008 | Jung | G16H 10/20 600/544 |
| 2009/0226060 | A1* | 9/2009 | Gering | G06T 7/143 382/128 |
| 2011/0053951 | A1* | 3/2011 | Kemp | C07D 403/06 514/252.05 |
| 2011/0107270 | A1* | 5/2011 | Wang | G06F 19/3481 715/850 |
| 2013/0101189 | A1* | 4/2013 | Robitaille | G06T 5/007 382/128 |
| 2014/0275706 | A1* | 9/2014 | Dean | A61N 5/1031 600/1 |
| 2017/0091574 | A1* | 3/2017 | Udupa | A61N 5/1039 |

OTHER PUBLICATIONS

Y. Tong et al., "Standardized anatomic space for abdominal fat quantification", 2014, Medical Imaging 2014: Image Processing, Proc. of SPIE vol. 9034, p. 1-6.*
P. De Leyn et al., "Revised ESTS guidelines for preoperative mediastinal lymph node staging for non-small-cell lung cancer", 2014, European Journal of Cardio-Thoracic Surgery, vol. 45, Issue 5, May 1, 2014, pp. 787-798.*
Tobias Emrich, Franz Graf, Hans-Peter Kriegel, Matthias Schubert, Marisa Thoma, Alexander Cavallaro, "CT slice localization via instance-based regression," Proc. SPIE 7623, Medical Imaging 2010: Image Processing, (Mar. 12, 2010), p. 1-13 (Year: 2010).*
Cavallaro et al., "Region of Interest Queries in CT Scans", SSTD 2011, p. 1-18 (Year: 2011).*
Jürgen Machann, Claus Thamer MD, Birgit Schnoedt, Michael Haap MD, Hans-Ulrich Haring MD, Claus D. Claussen MD, Michael Stumvoll MD, Andreas Fritsche MD, Fritz Schick PhD, MD, "Standardized assessment of whole body adipose tissue topography by MRI", JMRI, vol. 21, Issue 4, p. 455-462, Mar. 18, 2005 (Year: 2005).*
N. Kovacevic, G. Hamarneh, and M. Henkelman, Anatomically Guided Registration of Whole Body Mouse MR Images, 2003, Medical Image Computing and Computer-Assisted, p. 870-877 (Year: 2003).*
Cabezas, M., Oliver, A., Llado, X., Freixenet, J., Cuadra, M.B., 2011. A review of atlas-based segmentation for magnetic resonance brain images. Comput Methods Programs Biomed 104, 158-177.
Boykov, Y., Veksler, O., Zabih, R., 2001. Fast approximate energy minimization via graph cuts. IEEE Transactions on Pattern Analysis and Machine Intelligence 23, 1222-1239.
Bogovic, J.A., Prince, J.L., Bazin, P.L., 2013. A multiple object geometric deformable model for image segmentation. Computer Vision and Image Understanding 117, 145-157.
Beucher, S., 1992. The Watershed Transformation applied to image segmentation, 10th Pfefferkor Conference on Signal and Image Processing in Microscopy and Microanalysis, pp. 299-314.
Baiker, M., Milles, J., Dijkstra, J., Henning, T.D., Weber, A.W., Que, I., Kaijzel, E.L., Lowik, C.W.G.M., Reiber, J.H.C., Lelieveldt, B.P.F., 2010. Atlas-based whole-body segmentation of mice from low-contrast Micro-CT data. Medical Image Analysis 14, 723-737.
Ashburner, J., Friston, K.J., 2009. Computing average shaped tissue probability templates. Neuroimage 45, 333-341.
Arens, R., Sin, S., Nandalike, K., Rieder, J., Khan, U.I., Freeman, K., Wylie-Rosett, J., Lipton, M.L., Wootton, D.M., McDonough, J.M., Shifteh, K., 2011. Upper Airway Structure and Body Fat Composition in Obese Children with Obstructive Sleep Apnea Syndrome. American Journal of Respiratory and Critical Care Medicine 183, 782-787.
Zhuge, Y., Udupa, J.K., 2009. Intensity standardization simplifies brain MR image segmentation, Computer, Vision and Image Understanding 113, 1095-1103.
Zhuge, Y., Ciesielski, K.C., Udupa, J.K., Miller, R.W., 2013. GPU-based relative fuzzy connectedness image segmentation. Medical Physics 40 (1), 011903-1-011903-10.
Zhuge, Y., Cao, Y., Udupa, J.K., Miller, R.W., 2011. Parallel fuzzy connected image segmentation on GPU. Medical Physics 38(7), 4365-4371.
Zhou, Y.X., Bai, J., 2007. Atlas-based fuzzy connectedness segmentation and intensity non-uniformity correction applied to brain MRI. IEEE Transactions on Biomedical Engineering 54, 122-129.
Zhou, X., Yamaguchi, S., Zhou, X., Chen, H., Hara, T., Yokoyama, R., Kanematsu, M. and Fujita, H., 2013. Automatic organ localization on 3D CT images by using majority-voting of multiple 2D detections based on local binary patterns and Haar-like features, SPIE Medical Imaging. SPIE, pp. 86703A-86701-86703A-86707.
Zhou, J., Rajapakse, J.C., 2005. Segmentation of subcoliical brain structures using fuzzy templates. Neuroimage 28, 915-924.
Van der Lijn, F., de Bruijne, M., Klein, S., den Heijer, T., Hoogendam, Y.Y., van der Lugt, A., Breteler, M.M.B., Niessen, W.J., 2012. Automated Brain Structure Segmentation Based on Atlas Registration and Appearance Models. IEEE Transactions on Medical Imaging 31, 276-286.
Udupa, J.K., Samarasekera, S., 1996. Fuzzy connectedness and object definition: Theory, algorithms, and applications in image segmentation. Graphical Models and Image Processing 58, 246-261.
Udupa et al. in "Fuzzy-model-based body-wide anatomy recognition in medical images", Proc. SPIE Medical Imaging, 8671:8671B (2013).
Udupa et al. in "Fuzzy object modeling," Proc. SPIE Medical Imaging, 7964:7964 B-1 (2011).
Tsechpenakis, G., Chatzis, S.P., 2011. Deformable probability maps: Probabilistic shape and appearance-based object segmentation Computer Vision and Image Understanding 115, 1157-1169.
Torigian, et al., "The evolving role of structural and functional imaging in assessment of age-related changes in the body", Semin Nucl Med, 2007, 37, 64-68.
Tong et al. Standardized anatomic space for abdominal fat quantification. Proc. of SPIE vol. 9034. May 15, 2014. [retrieved Jul. 25, 2015]. Retrieved from Internet: <URL http://www.mipg/upenn.edu/yubing/2014_FAT.pdf.
Staib, L.H., Duncan, U.S., 1992. Boundary Finding with Parametrically Deformable Models. IEEE Transactions on Pattern Analysis and Machine Intelligence 14, 1061-1075.
Souza, A., and Udupa, J.K., 2006. Iterative live wire and live snake: New user-steered 3D image segmentation paradigms, SPIE Medical Imaging. SPIE, pp. 1159-1165.
Shen, T.A., Li, H.S., Huang, X.L., 2011. Active Volume Models for Medical Image Segmentation. IEEE Transactions on Medical Imaging 30, 774-791.

(56) References Cited

OTHER PUBLICATIONS

Shattuck, D.W., Mirza, M., Adisetiyo, V., Hojatkashani, C., Salamon, G., NaIT, K.L., Poldrack, R.A., Bilder, R.M., Toga, A.W., 2008. Construction of a 3D probabilistic atlas of human cortical structures. Neuroimage 39, 1064-1080.

Saha, P.K., Udupa, J.K., 2001. Relative fuzzy connectedness among multiple objects: Theory, algorithms, and applications in image segmentation. Computer Vision and Image Understanding 82, 42-56.

Rusch et al., "The IASLC lung cancer staging project: a proposal for a new international lymph node map in the forthcoming seventh edition of the TNM classification for lung cancer," Journal of Thoracic Oncology, 4(5), 568-577 (2009).

Rousson, M., Paragios, N., 2008. Prior knowledge, level set representations & visual grouping. International Journal of Computer Vision 76, 231-243.

Robertson, D., Konukoglu, E., Shotton, J., Pathak, S., White, S., Siddiqui, K., 2013. Regression forests for efficient anatomy detection and localization in computed tomography scans. Med Image Anal 17, 1293-1303.

Raya, S.P., Udupa, J.K., 1990. Shape-Based Interpolation of Multidimensional Objects. IEEE Transactions on Medical Imaging 9, 32-42.

Pizer, S.M., Fletcher, P.T., Joshi, S., Thall, A., Chen, J.Z., Fridman, Y., Fritsch, D.S., Gash, A.G., Glotzer, J.M., Jiroutek, M.R., Lu, C.L., Muller, K.E., Tracton, G., Yushkevich, P., Chaney, E.L., 2003. Deformable M-reps for 3D medical image segmentation. International Journal of Computer Vision 55, 85-106.

Okada, T., Yokota, K., Hori, M., Nakamoto, M., Nakamura, H., Sato, Y., 2008. Construction of hierarchical multi-organ statistical atlases and their application to multi-organ segmentation from CT images. Med Image Comput Comput Assist Interv 11, 502-509.

Nyul, L.G., Udupa, J.K., 1999. On standardizing the MR image intensity scale. Magnetic Resonance in Medicine 42, 1072-1081.

Mumford, D., Shah, J., 1989. Optimal Approximations by Piecewise Smooth Functions and Associated Variational-Problems Communications on Pure and Applied Mathematics 42, 577-685.

Miranda, P.A.V., Falcao, A.X. and Udupa J.K, 2009. Cloud Bank: A multiple clouds model and its use in MR brain image segmentation, ISBI, pp. 506-509.

Miranda, P.A.V., Falcao, A.X. and Udupa J.K, 2008. Clouds: A model for synergistic image segmentation, ISBI, pp. 209-212.

Meyer, C., Peters, J. and Weese, J., 2011. Fully automatic segmentation of complex organ systems: Example of trachea, esophagus and heart segmentation in CT images, SPIE Medical Imaging. SPIE, pp. 796216-796211.

Maurer, C.R., Qi, R.S., Raghavan, V., 2003. A linear time algorithm for computing exact Euclidean distance transforms of binary images in arbitrary dimensions. IEEE Transactions on Pattern Analysis and Machine Intelligence 25, 265-270.

Malladi, R., Sethian, J.A., Vemuri, B.C., 1995. Shape Modeling with Front Propagation—a Level Set Approach. IEEE Transactions on Pattern Analysis and Machine Intelligence 17, 158-175.

Maji, P., Pal, S.K., 2012. Rough-Fuzzy Pattern Recognition: Applications in Bioinformatics and Medical Imaging, John Wiley & Sons, Inc. New York).

Lu, C., Zheng, Y., Birkbeck, N., Zhang, J., Kohlberger, T., Tietjen, C., Boettger, T., Duncan, J.S., Zhou, S.K., 2012. Precise segmentation of multiple organs in CT volumes using learning-based approach and information theory. Med Image Comput Comput Assist Interv 15, 462-469.

Liu, J.M., Udupa, J.K., 2009. Oriented Active Shape Models. IEEE Transactions on Medical Imaging 28, 571-584.

Linguraru, M.G., Pura, J.A., Pamulapati, V., Summers, R.M., 2012. Statistical 4D graphs for multi-organ abdominal segmentation from multiphase CT. Med Image Anal 16, 904-914.

Klein, S., Staring, M., Murphy, K., Viergever, M.A., Pluim, J.P.W., 2010. Elastix: a toolbox for intensity based medical image registration, IEEE Transactions on Medical Imaging, 29, 196-205.

Kass, M., Witkin, A., Terzopoulos, D., 1987. Snakes—Active Contour Models. International Journal of Computer Vision 1, 321-331.

Journal of Mathematical Imaging and Vision 44, 375-398.

Ichimura et al., "Caudal border of level 2R in the new international lymph node map for lung cancer," Journal Thoracic Oncology, vol. 5 No. 4, Apr. 2010, pp. 579-580 (2010).

Horsfield, M.A., Bakshi, R., Rovaris, M., Rocca, M.A., Dandamudi, V.S.R., Valsasina, P., Judica, E., Lucchini, F., Guttmann, C.R.G., Sormani, M.P., Filippi, M., 2007. Incorporating domain knowledge into the fuzzy connectedness framework: Application to brain lesion volume estimation in multiple sclerosis. IEEE Transactions on Medical Imaging 26, 1670-1680.

Heimann, T., Meinzer, H.P., 2009. Statistical shape models for 3D medical image segmentation: A review. Medical Image Analysis 13, 543-563.

Hansegard, J., Urheim, S., Lunde, K., Rabben, S.I., 2007. Constrained active appearance models for segmentation of triplane echocardiograms. IEEE Transactions on Medical Imaging 26, 1391-1400.

Duta, N., Sonka, M., 1998. Segmentation and interpretation of MR brain images: An improved active shape model. IEEE Transactions on Medical Imaging 17, 1049-1062.

De Leyn et al. Revised ESTS guidelines for preoperative mediastinal lymph node staging for non-small-cell lung cancer. European Journal of Cardio-thoracic Surgery. Feb. 26, 2014. [retrieved Jul. 25, 2015]. Retrieved from internet: <URL: http://www.ests.org/_userfiles/pages/files/Revised%20ESTS%20Guidelines.pdf> pp. 1-12.

Cootes, T.F., Edwards, G.J., Taylor, C.J., 2001. Active appearance models. IEEE Transactions on Pattern Analysis and Machine Intelligence 23, 681-685.

Ciesielski, K.C., Udupa, J.K., Falcao, A.X., Miranda, P.A.V., 2012 Fuzzy Connectedness Image Segmentation in Graph Cut Formulation: A Linear-Time Algorithm and a Comparative Analysis.

Chu, C., Oda, M., Kitasaka, T., Misawa, K., Fujiwara, M., Hayashi, Y., Wolz, R., Rueckert, D. and Mori, K, 2013. Multi-organ segmentation from 3D abdominal CT images using patient-specific weighted-probabilistic atlas, SPIE Medical Imaging. SPIE, pp. 86693Y-86691-86693Y-86697.

Chen, XJ., Udupa, J.K., Bagci, U., Zhuge, Y., Yao, J., 2012. Medical image segmentation by combining graph cut and oriented active appearance models, IEEE Transactions on Image Processing 21(4), 2035-2046.

Chen, X.J., Bagci, U., 2011. 3D automatic anatomy segmentation based on iterative graph-cut-ASM. Medical Physics 38, 4610-4622.

Cerrolaza, J.J., Villanueva, A., Cabeza, R., 2012. Hierarchical Statistical Shape Models of Multiobject Anatomical Structures: Application to Brain MRI. IEEE Transactions on Medical Imaging 31, 713-724.

* cited by examiner

APPLICATIONS OF AUTOMATIC ANATOMY RECOGNITION IN MEDICAL TOMOGRAPHIC IMAGERY BASED ON FUZZY ANATOMY MODELS

CROSS-REFERENCE TO RELATED APPLICATIONS

The instant application is a National Stage Application filed under 35 U.S.C. 371 of International Application No. PCT/US2015/030833, filed May 14, 2015, which claims priority to U.S. provisional patent application Nos. 61/994,494, filed May 16, 2014 and 62/116,222, filed Feb. 13, 2015. These provisional patent applications are hereby incorporated by reference in their entireties.

GOVERNMENT RIGHTS

This invention was made with government support under grant numbers HL105212 and HD052693 awarded by the National Institutes of Health. The government has certain rights in the invention.

TECHNICAL FIELD

The invention relates to applications utilizing a method for analyzing areas of the anatomy that is independent of imaging modality and that uses automatic anatomy recognition to identify all organs within a particular body segment, such as the thorax, abdomen, and neck. Applications include methods for quantifying abdominal fat on CT images using standardized anatomic space, methods for automatic localization of IASLC-defined mediastinal lymph node stations on CT images using fuzzy models, and methods for optimized radiotherapy planning.

BACKGROUND

Since the birth of radiology in 1895, the emphasis in clinical radiology has been on human visualization of internal structures. Although various tomographic image modalities evolved subsequently for deriving anatomic, functional, and molecular information about internal structures, the emphasis on human visualization continued and the practice of clinical radiology has remained mostly descriptive and subjective. Quantification is amply employed in radiology in clinical research. However, in clinical radiological practice, this is not common. In the qualitative mode, quantifiable and/or subtle image information is underutilized, interpretations remain subjective, and subtle changes at early disease stages or due to therapeutic intervention may be underestimated or missed (Torigian, D. A., Alavi, A., 2007. The evolving role of structural and functional imaging in assessment of age-related changes in the body. Semin Nucl Med 37, 64-68). It is generally believed now that if Quantitative Radiology (QR) can be brought to routine clinical practice, numerous advances can be made including: improved sensitivity, specificity, accuracy, and precision of early disease diagnosis; more objective and standardized response assessment of disease to treatment; improved understanding of what is "normal"; increased ease of disease measurement and reporting; and discovery of new disease biomarkers.

To make QR a reality, the inventors believe that computerized Automatic Anatomy Recognition (AAR) during radiological image interpretation becomes essential. To facilitate AAR, and hence eventually QR, and focusing only on the anatomic aspects of shape, geography, and architecture of organs, while keeping the larger goal in mind, the inventors present herein a novel fuzzy strategy for building anatomic models of different regions of the body, and for utilizing these models for automatically recognizing and delineating anatomy in given patient images.

Image segmentation—the process of recognizing and delineating objects in images—has a rich literature spanning over five decades. From the perspective of the direction in which this field is headed, it is useful to classify the methods developed to date into three groups: (a) Purely image-based, or pI approaches (Beucher, S., 1992. The Watershed Transformation applied to image segmentation, 10th Pfefferkorn Conference on Signal and Image Processing in Microscopy and Microanalysis, pp. 299-314; Boykov, Y., Veksler, O., Zabih, R., 2001. Fast approximate energy minimization via graph cuts. IEEE Transactions on Pattern Analysis and Machine Intelligence 23, 1222-1239; Kass, M., Witkin, A., Terzopoulos, D., 1987. Snakes—Active Contour Models. International Journal of Computer Vision 1, 321-331; Malladi, R., Sethian, J. A., Vemuri, B. C., 1995. Shape Modeling with Front Propagation—a Level Set Approach. IEEE Transactions on Pattern Analysis and Machine Intelligence 17, 158-175; Mumford, D., Shah, J., 1989. Optimal Approximations by Piecewise Smooth Functions and Associated Variational-Problems. Communications on Pure and Applied Mathematics 42, 577-685; and Udupa, J. K., Samarasekera, S., 1996. Fuzzy connectedness and object definition: Theory, algorithms, and applications in image segmentation. Graphical Models and Image Processing 58, 246-261), wherein segmentation decisions are made based entirely on information derived from the given image; (b) Object model-based, or OM approaches (Ashburner, J., Friston, K. J., 2009. Computing average shaped tissue probability templates. Neuroimage 45, 333-341; Cootes, T. F., Edwards, G. J., Taylor, C. J., 2001. Active appearance models. IEEE Transactions on Pattern Analysis and Machine Intelligence 23, 681-685; Heimann, T., Meinzer, H. P., 2009. Statistical shape models for 3D medical image segmentation: A review. Medical Image Analysis 13, 543-563; Pizer, S. M., Fletcher, P. T., Joshi, S., Thall, A., Chen, J. Z., Fridman, Y., Fritsch, D. S., Gash, A. G., Glotzer, J. M., Jiroutek, M. R., Lu, C. L., Muller, K. E., Tracton, G., Yushkevich, P., Chancy, E. L., 2003. Deformable M-reps for 3D medical image segmentation. International Journal of Computer Vision 55, 85-106; Shattuck, D. W., Mirza, M., Adisetiyo, V., Hojatkashani, C., Salamon, G., Nan, K. L., Poldrack, R. A., Bilder, R. M., Toga, A. W., 2008. Construction of a 3D probabilistic atlas of human cortical structures. Neuroimage 39, 1064-1080; and Staib, L. H., Duncan, J. S., 1992. Boundary Finding with Parametrically Deformable Models. IEEE Transactions on Pattern Analysis and Machine Intelligence 14, 1061-1075), wherein known object shape and image appearance information over a population are first codified in a model and then utilized on a given image to bring constraints into the segmentation process; (c) Hybrid approaches (Chen, X. J., Bagci, U., 2011. 3D automatic anatomy segmentation based on iterative graph-cut-ASM. Medical Physics 38, 4610-4622; Hansegard, J., Urheim, S., Lunde, K., Rabben, S. I., 2007. Constrained active appearance models for segmentation of triplane echocardiograms. IEEE Transactions on Medical Imaging 26, 1391-1400; Horsfield, M. A., Bakshi, R., Rovaris, M., Rocca, M. A., Dandamudi, V. S. R., Valsasina, P., Judica, E., Lucchini, F., Guttmann, C. R. G., Sormani, M. P., Filippi, M., 2007. Incorporating domain knowledge into the fuzzy connectedness framework: Application to brain lesion volume estimation in multiple sclerosis. IEEE Transactions on Medical Imaging 26, 1670-1680; Liu, J. M., Udupa, J. K., 2009. Oriented Active Shape Models. IEEE Transactions on Medical Imaging 28, 571-584; Rousson, M., Paragios, N., 2008. Prior knowledge, level set representations & visual grouping. International Journal of Computer Vision 76, 231-243; Shen, T. A., Li, H. S., Huang, X. L., 2011. Active Volume Models for Medical Image Segmentation. IEEE Transactions on Medical Imaging 30, 774-791; van der Lijn, F., de Bruijne, M., Klein, S., den Heijer, T., Hoogendam, Y. Y., van der Lugt, A., Breteler, M. M. B., Niessen, W. J., 2012. Automated Brain Structure Segmentation Based on Atlas Registration and Appearance Models. IEEE Transactions on Medical Imaging 31, 276-286; and Zhou, Y. X., Bai, J., 2007. Atlas-based fuzzy connectedness segmentation and intensity non-uniformity correction applied to brain MRI. IEEE Transactions on Biomedical Engineering 54, 122-129), wherein the delineation strengths of the pI methods are combined synergistically with the global object recognition capabilities of the OM strategies. pI algorithms predate other approaches, and they still continue to seek new frontiers. OM approaches go by various names such as statistical models and probabilistic atlases, and continue to be pursued aggressively. Particularly, atlas-based techniques have gained popularity in brain MR image segmentation and analysis (Cabezas, M., Oliver, A., Llado, X., Freixenet, J., Cuadra, M. B., 2011. A review of atlas-based segmentation for magnetic resonance brain images. Comput Methods Programs Biomed 104, 158-177). Hybrid approaches hold much promise for AAR and QR and are currently very actively investigated. Since the focus of the invention is the body torso, and since the nature of the images and of the objects and challenges encountered are different for these regions (from, for example, for the brain), the review below will focus mainly on methods developed for the torso though such methods are not limited to the torso.

Since the simultaneous consideration of multiple objects offers better constraints, in recent years, multi-object strategies have been studied under all three groups of approaches to improve segmentation. Under pI approaches, the strategy sets up a competition among objects for delineating their regions/boundaries (e.g., Bogovic, J. A., Prince, J. L., Bazin, P. L., 2013. A multiple object geometric deformable model for image segmentation. Computer Vision and Image Understanding 117, 145-157; and Saha, P. K., Udupa, J. K., 2001. Relative fuzzy connectedness among multiple objects: Theory, algorithms, and applications in image segmentation. Computer Vision and Image Understanding 82, 42-56). In OM approaches, the strategy allows including inter-relationships among objects in the model to influence their localization and delineation (e.g.; Cerrolaza, J. J., Villanueva, A., Cabcza, R., 2012. Hierarchical Statistical Shape Models of Multiobject Anatomical Structures: Application to Brain MRI. IEEE Transactions on Medical Imaging 31, 713-724 and Duta, N., Sonka, M., 1998. Segmentation and interpretation of MR brain images: An improved active shape model. IEEE Transactions on Medical Imaging 17, 1049-1062). In hybrid approaches, multi-object strategies try to strengthen segmentability by incorporating relevant information in model building, object recognition/localization, and subsequently also in delineation via the pI counterpart of the synergistic approach (Chen, X J., Udupa, J. K., Bagci, U., Zhuge, Y., Yao, J., 2012. Medical image segmentation by combining graph cut and oriented active appearance models, IEEE Transactions on Image Processing 21(4), 2035-2046; Chu, C., Oda, M., Kitasaka, T., Misawa, K., Fujiwara, M., Hayashi, Y., Wolz, R., Rueckert, D. and Mori, K, 2013. Multi-organ segmentation from 3D abdominal CT images using patient-specific weighted-probabilistic atlas, SPIE Medical Imaging. SPIE, pp. 86693Y-86691-86693Y-86697; Linguraru, M. G., Pura, J. A., Pamulapati, V., Summers, R. M., 2012. Statistical 4D graphs for multi-organ abdominal segmentation from multiphase CT. Med Image Anal 16, 904-914; Lu, C., Zheng, Y., Birkbeck, N., Zhang, J., Kohlberger, T., Tietjen, C., Boettger, T., Duncan, J. S., Zhou, S. K., 2012. Precise segmentation of multiple organs in CT volumes using learning-based approach and information theory. Med Image Comput Assist Intery 15, 462-469; Meyer, C., Peters, J. and Weese, J., 2011. Fully automatic segmentation of complex organ systems: Example of trachea, esophagus and heart segmentation in CT images, SPIE Medical Imaging. SPIE, pp. 796216-796211-796216-796211; Okada, T., Yokota, K., Hori, M., Nakamoto, M., Nakamura, H., Sato, Y., 2008. Construction of hierarchical multi-organ statistical atlases and their application to multi-organ segmentation from CT images. Med Image Comput Assist Intery 11, 502509; Shen, T. A., Li, H. S., Huang, X. L., 2011. Active Volume Models for Medical Image Segmentation. IEEE Transactions on Medical Imaging 30, 774-791; and Tsechpenakis, G., Chatzis, S. P., 2011. Deformable probability maps: Probabilistic shape and appearance-based object segmentation. Computer Vision and Image Understanding 115, 1157-1169). Motivated by applications (such as semantic navigation) where the focus is just locating objects in image volumes and not delineating them, a separate group of methods has been emerging (Criminisi, A., Robertson, D., Konukoglu, E., Shotton, J., Pathak, S., White, S., Siddiqui, K., 2013. Regression forests for efficient anatomy detection and localization in computed tomography scans. Med Image Anal 17, 1293-1303; Zhou, J., Rajapakse, J. C., 2005. Segmentation of subcortical brain structures using fuzzy templates. NeuroImage 28, 915-924; and Zhou, X., Yamaguchi, S., Zhou, X., Chen, H., Hara, T., Yokoyama, R., Kancmatsu, M. and Fujita, H., 2013. Automatic organ localization on 3D CT images by using majority-voting of multiple 2D detections based on local binary patterns and Haar-like features, SPIE Medical Imaging. SPIE, pp. 86703A-86701-86703A-86707). They use features characterizing the presence of whole organs or specific anatomic aspects of organs (such as the femoral neck and head) combined with machine learning techniques to locate objects in image volumes by finding the size, location, and orientation of rectangular bounding boxes that just enclose the anatomic entities.

The state-of-the-art in image segmentation seems to leave several gaps that hinder the development of an AAR system applicable to different body regions. First, while multi-object strategies have clearly shown superior performance for all approaches, in all published works they have been confined to only a few (three to five) selected objects and have not taken into account an entire body region or all of its major organs, the only exception being Baiker, M., Mines, J., Dijkstra, J., Henning, T. D., Weber, A. W., Que, I., Kaijzel, E. L., Lowik, C. W. G. M., Reiber, J. H. C., Lelieveldt, B. P. F., 2010. Atlas-based whole-body segmentation of mice from low-contrast Micro-CT data. Medical Image Analysis 14, 723-737, whose focus was whole body segmentation of mice on micro CT images. Second, and as a result, there is no demonstrated single method that operates on different body regions, on all major organs in each body region, and at different modalities. Third, all reported modeling strategies have a statistical framework, either as statistical models of shape and intensity pattern of appearance of objects in the image or as atlases, and none taking a fuzzy approach, except Zhou, J., Rajapakse, J. C., 2005. Segmentation of subcortical brain structures using fuzzy templates. NeuroImage 28, 915-924, and in the inventors' previous work Miranda, P. A. V., Falcao, A. X. and Udupa J. K, 2008. Clouds: A model for synergistic image segmentation, ISBI, pp. 209-212; and Miranda, P. A. V., Falcao, A. X. and Udupa J. K, 2009. Cloud Bank: A multiple clouds model and its use in MR brain image segmentation, ISBI, pp. 506-509, both in the brain only.

Fuzzy set concepts have been used extensively otherwise in image processing and 3D visualization. Fuzzy modeling approaches allow bringing anatomic information in an all-digital form into graph theoretic frameworks designed for object recognition and delineation, obviating the need for (continuous) assumptions made otherwise in statistical approaches about shapes, random variables, their independence, functional form of density distributions, etc. They also allow capturing information about uncertainties at the patient level (e.g., blur, partial volume effects) and population level, and codification of this information within the model. Fourth, objects have complex inter-relationships in terms of their geographic layout. Learning this information over a population and encoding this explicitly in an object hierarchy can facilitate object localization considerably. Although several multi-object methods have accounted for this relationship indirectly, its direct incorporation into modeling, object recognition, and delineation in an anatomic hierarchical order has not been attempted. The AAR approach presented herein is designed to help overcome these gaps and, in exemplary embodiments, to provide a mechanism for quantifying abdominal fat, a mechanism for automatic localization of IASLC-defined mediastinal lymph node stations, and a mechanism for optimizing radiation therapy planning.

Quantifying Abdominal Fat

Obesity and physical inactivity are global epidemics that warrant the immediate attention of the health-care community. An estimated two-thirds of Americans are overweight or obese. The accumulation of abdominal subcutaneous, visceral, and organ fat has adverse effects on health and increased risks of heart disease, diabetes mellitus, metabolic disorders, obstructive sleep apnea, and certain cancers. The ability to accurately measure subcutaneous adipose tissue (SAT) and visceral adipose tissue (VAT) becomes more imperative as their contribution to disease pathophysiology becomes clearer.

Anthropometric biomarkers for central obesity such as waist circumference, waist-hip ratio, and body mass index (BMI) are widely used clinically. However, those are indirect methods for fat measurement, and previous research has shown that BMI alone does not differentiate between obese phenotypes even though body composition (differences in fat distribution given the same BMI) may indicate different phenotypes of obese subjects. To date, magnetic resonance imaging (MRI) and computed tomography (CT) remain the imaging modalities of choice for SAT and VAT assessment. In both modalities, SAT can be usually segmented first by manually drawing the interface boundary between SAT and VAT, and then VAT can be segmented by thresholding the image left after removing the SAT portion of the image. However, several algorithms have also been proposed to make fat quantification more automated and efficient, such as fuzzy clustering, fuzzy c-means clustering, active contour approach, and registration. Clustering and registration algorithms require much computation, and active contour approaches require human interaction. The inventors describe herein a rapid prototyping method that adapts an automatic anatomy recognition (AAR) system based on fuzzy object models that is adapted for anatomy segmentation to the fat quantification application. As explained below, that method demonstrates that fat quantification can be accomplished automatically even when the imaging modalities, subject groups, and number of delineated objects are different from those employed for the AAR model building step. There is no clustering and registration in AAR and it can run quite efficiently once off-line training and model building have been completed.

In clinical practice, a marker of the total amount of body fat is typically obtained by the fat area measured from one transverse abdominal slice (from CT or MRI), commonly acquired at the level of the L4-L5 vertebrae, for various reasons including decreased radiation exposure and cost. It is generally assumed that such an estimate can reliably act as a marker of the burden of fat in the body. There are two issues related to this common practice. First, no studies exist that have examined systematically how to specify spatial location for slices in different subjects consistently so that they are in the same homologous anatomic location. One way is to manually label the spatial location, such as L3-L4 or L4-L5 for all subjects, where the areas of SAT and VAT from every subject are used to calculate correlations with SAT and VAT volumes, respectively, from all subjects. Spatial location L4-L5 is labeled as 0 and then other adjacent/neighboring slices are labeled with continuous numbers, such as '+1', up to '+20'. Seven landmarks are set for every subject where correlation is computed at just those slices corresponding to landmarks. However, the slices between landmarks are omitted and the maximum correlation may happen at some site between landmarks. Slice locations are defined relative to L4-L5, where single-slice image located 5 cm above L4-L5 is used to compare with the slice at level L4-L5. However, the slices at 5 cm above L4-L5 may not be at the same anatomic site for every subject due to variability among subjects. Only the umbilical slice and slice at L4-L5 are labeled and adopted for calculating correlation between SAT/VAT area and volume. These approaches are labor-intensive, especially since it is desired to check all possible slice locations for correlation (whether with single or multiple slices) to determine where maximum correlations may occur. Second, by using a facility for consistency of slice localization, no studies have investigated which single location or multiple locations for the slices yield maximum correlation of the fat areas on the slices with the total fat volume for the SAT and VAT components separately. The methods described herein are adapted to address both of these issues. For the purpose of this description, SAT and VAT volume/area can be quantified from CT or MR images by using any of the above segmentation methods, although the AAR rapid prototyping approach mentioned above is used for demonstrating the concepts and results.

The inventors thus recognize that the quantification of body fat plays an important role in the study of numerous diseases. It is common current practice to use the fat area at a single abdominal CT slice as a marker of the body fat content in studying various disease processes. The inventors propose to answer three questions related to this issue that have not been adequately addressed in the literature. First, at what single anatomic slice location do the areas of subcutaneous adipose tissue (SAT) and visceral adipose tissue (VAT) estimated from the slice correlate maximally with the corresponding fat volume measures? Second, how does one ensure that the slices used for correlation calculation from different subjects are at the same anatomic location? Third, are there combinations of multiple slices (not necessarily contiguous) whose area sum correlates better with volume than does single slice area with volume? Techniques are further described for addressing these questions.

Automatic Localization of IASLC-Defined Mediastinal Lymph Node Stations

Lung cancer is associated with the highest cancer mortality rates among men and women in the United States. The accurate and precise identification of the lymph node stations on computed tomography (CT) images is important for staging disease and potentially for prognosticating outcome in patients with lung cancer, as well as for pretreatment planning and response assessment purposes. To facilitate a standard means of referring to lymph nodes, the International Association for the Study of Lung Cancer (IASLC) has recently proposed a definition of the different lymph node stations and zones in the thorax. However, nodal station identification is typically performed manually by visual assessment in clinical radiology. This approach leaves room for error due to the subjective and potentially ambiguous nature of visual interpretation, and is labor intensive.

The International Association for the Study of Lung Cancer (IA SLC) has recently proposed (Rusch et al., "The IASLC lung cancer staging project: a proposal for a new international lymph node map in the forthcoming seventh edition of the TNM classification for lung cancer," Journal of Thoracic Oncology, 4(5), 568-577 (2009)) a unified way of specifying lymph node stations and zones in thoracic computed tomography (CT) images. This initiative is useful to systematically assess the involvement of regional lymph nodes in lung cancer patients in a standardized manner, which is important for disease staging and potentially for prognostication of patient outcome. While this formulation is helpful in standardizing a means of interpreting and reporting thoracic lymph node disease sites, it still leaves the radiologist with the arduous task of following the detailed specifications and finding the nodal stations and zones on images subjectively. Automation of this task is highly desirable.

Radiation Therapy Planning

Those skilled in the art will appreciate that the contouring of critical organs and of the target tumor in medical images is required for accurate radiotherapy planning to ensure that the proper dose of radiation is delivered to the tumor while radiation is minimized to the healthy organs. There are two major issues with the current clinical practice of contouring that are addressed by the techniques of the invention, namely, poor efficiency (throughput and reproducibility) and poor accuracy. The conventional clinical practice for delineating organs prior to radiation treatment is still performed with little, if any, machine assistance, even though the process is both time consuming and prone to inter-observer variation. Automation of the contouring task is desired to improve efficiency and accuracy and to eliminate observer variations. Also, automating such processes will enable the use of advance radiation therapy (RT) procedures that require repeated contouring of objects to handle anatomic changes taking place during RT due to weight loss or deformation of tumor and normal tissues. Such changes can significantly affect the total dose delivered to the tumor and normal surrounding organs and are particularly important when treating most thoracic malignancies. Proton beam radiation therapy (PERT) can allow for ultra-precise delivery of treatment due to the physical characteristics of the proton beam, eliminate exit dose, maximize dose delivered to the tumor, and minimize radiation dose to adjacent organs at risk, reducing toxicity and patient morbidity, and improving clinical outcomes like overall survival. Yet, because of the poor efficiency and throughput of current software products, re-contouring is rarely done. While the extent of impact of this issue on patient outcome is not known at present, with automation of contouring, advanced RT methods such as IMRT and PBRT can be employed more extensively for improved outcomes.

In spite of recent advances in image segmentation, the inventors believe there to be three main reasons for the current lack of automatic contouring tools. First, in all published works, methods and tools have been confined to only a few (3-5) selected objects and have not extended to an entire body region or all of its major organs, which is often needed for RT planning and can actually facilitate segmentation even if the focus is only on a few objects. Second, as a result, there is no single available method that operates on different body regions and on all major organs in each body region. Typically a new method is/has to be engineered when dealing with a new set of organs, or a new body site, or a new imaging modality/sequence. Third, objects have complex inter-relationships in geographic layout, size co-variations, pose co-variations, image intensity co-variations, neighborhood arrangement, etc. Thorough understanding and subsequently algorithmic encoding of this information are needed to facilitate robust object localization and delineation. These relationships are discontinuous and non-linear, and it is very challenging to incorporate them into methods that require smooth deformations such as atlas approaches.

The AAR methodology described herein is a radically different approach, designed to overcome these barriers, and to be applicable to multitudes of organs body-region-wide and body-wide, with a rapid prototyping capability to adapt the same methodology to different applications and even image modalities. With these features, the AAR approach of the invention will advance image segmentation practice by minimizing/eliminating re-development of tools for different body regions and modalities and thereby reducing developmental cost significantly for RT and other applications.

The above and other limitations in the prior art will be addressed by the methods and systems of the invention described herein.

SUMMARY

To make Quantitative Radiology (QR) a reality in radiological practice, computerized automatic anatomy recognition (AAR) becomes essential to increase accuracy of organ positioning when positioning a patient for radiation, for example. With the goal of building a general AAR system that is not tied to any specific organ system, body region, or image modality, the invention provides an AAR methodology for localizing and delineating all major organs in different body regions based on fuzzy modeling ideas and a tight integration of fuzzy models with an Iterative Relative Fuzzy Connectedness (IRFC) delineation algorithm. The methodology consists of five main steps: (a) gathering image data for both building models and testing the AAR algorithms from patient image sets existing in a health system; (b) formulating precise definitions of each body region and organ and delineating them following these definitions; (c) building hierarchical fuzzy anatomy models of organs for each body region; (d) recognizing and locating organs in given images by employing the hierarchical models; and (e) delineating the organs following the hierarchy. In Step (c), object size and positional relationships are specifically encoded into the hierarchy and subsequently exploited in object recognition in Step (d) and delineation in Step (e).

Modality-independent and dependent aspects are carefully separated in model encoding. At the model building stage, a learning process is carried out for rehearsing an optimal threshold-based object recognition method. The recognition process in Step (d) starts from large, well-defined objects and proceeds down the hierarchy in a global to local manner. A fuzzy model-based version of the IRFC algorithm is created by naturally integrating the fuzzy model constraints into the delineation algorithm.

The AAR system is tested on three body regions—thorax (on CT), abdomen (on CT and MR1), and neck (on MRI and CT)—involving a total of over 35 organs and 130 data sets (the total used for model building and testing). The training and testing data sets are divided into equal size in all cases except for the neck. Overall the AAR method achieves a mean accuracy of about 2 voxels in localizing non-sparse blob-like objects and most sparse tubular objects. The delineation accuracy in terms of mean false positive and negative volume fractions is 2% and 8%, respectively, for non-sparse objects, and 5% and 15%, respectively, for sparse objects. The two object groups achieve mean boundary distance relative to ground truth of 0.9 and 1.5 voxels, respectively. Some sparse objects—venous system (in the thorax on CT), inferior vena cava (in the abdomen on CT), and mandible and naso-pharynx (in neck on MM, but not on CT)—pose challenges at all levels, leading to poor recognition and/or delineation results. The AAR method fares quite favorably when compared with methods from the recent literature for liver, kidneys, and spleen on CT images. The inventors conclude that separation of modality-independent from dependent aspects, organization of objects in a hierarchy, encoding of object relationship information explicitly into the hierarchy, optimal threshold-based recognition learning, and fuzzy model-based IRFC are effective concepts that allowed the inventors to demonstrate the feasibility of a general AAR system that works in different body regions on a variety of organs and on different modalities.

The invention applies the AAR methodology described herein to quantify abdominal fat by developing a strategy for mapping slice locations to a standardized anatomic space so that the same anatomic slice locations arc identified in different subjects. The volume-to-area correlations are then studied to determine where they become maximal. Similar correlation studies are carried out by utilizing 2 and 3 slices for calculating an area sum. Based on 50 abdominal CT data sets, the mapping of the invention achieves significantly improved consistency of anatomic localization compared to current practice. Maximum correlations are achieved at different anatomic locations for SAT and VAT which are both different from the L4-L5 junction commonly utilized currently for single slice area estimation as a marker. The maximum area-to-volume correlation achieved is quite high, suggesting that it is reasonable to estimate body fat by measuring the area of fat from a single anatomic slice at the site of maximum correlation and use this as a marker. The site of maximum correlation is not at L4-L5 as commonly assumed, but is more superiorly located at T12-L1 for SAT and at L3-L4 for VAT. Furthermore, the optimal anatomic locations for SAT and VAT estimation are not the same, contrary to common assumption. The standardized space mapping of the invention achieves high consistency of anatomic localization by accurately managing non-linearities in the relationships among landmarks. Multiple slices achieve greater improvement in correlation for VAT than for SAT. The optimal locations in the case of multiple slices are not contiguous.

The inventors describe herein two approaches for slice localization. The first approach is linear mapping, where slice locations are linearly mapped from all subjects so that the superior-most and inferior-most anatomic slice locations match in the longitudinal direction for all subjects and other locations are linearly interpolated estimations. Although this linear mapping method is similar to the linear interpolation method described in the literature, the methods differ in an essential way. To make interpolation precise, the linear interpolation method requires the patients to be positioned precisely the same way and every patient should also be marked at the iliac crest for scan, which is not required for the approach described herein. In the second approach, slice locations in every subject are mapped non-linearly so that, in addition to the superior-most and inferior-most locations, several key landmark locations chosen in the longitudinal direction also match for all subjects. The methods of the invention thus address the above two issues by exploring anatomic space standardization and correlation calculation for the purpose of fat quantification.

The invention applies the AAR methodology described herein to identify mediastinal lymph node stations automatically during image interpretation. The inventors propose that if such techniques are made possible, then the acceptance of the IASLC standard and the consistency of its interpretation will be greatly facilitated, which may rapidly promote standardized reporting. The invention tests the feasibility of automatically localizing the mediastinal lymph node stations (See Udupa et al. in "Fuzzy object modeling," Proc. SPIE Medical Imaging, 7964:7964 B-1 (2011), and Udupa et al. in "Fuzzy-model-based body-wide anatomy recognition in medical images," Proc. SPIE Medical Imaging, 8671:8671B (2013)) by modifying a previously developed fuzzy-model-based body-wide automatic anatomy recognition (AAR) system to recognize IASLC defined features.

In particular, the method and system described herein provide automatic recognition of the mediastinal IASLC-defined lymph node stations by modifying a hierarchical fuzzy modeling approach previously developed for body-wide automatic anatomy recognition (AAR) in medical imagery. The AAR-lymph node (AAR-LN) system follows the AAR methodology and includes two steps. In the first step, the various lymph node stations are manually delineated on a set of CT images following the IASLC definitions. These delineations are then used to build a fuzzy hierarchical model of the nodal stations which are considered as 3D objects. In the second step, the stations are automatically located on any given CT image of the thorax by using the hierarchical fuzzy model and object recognition algorithms. Based on 23 data sets used for model building, 22 independent data sets for testing, and 10 lymph node stations, a mean localization accuracy of within 1-6 voxels has been achieved by the AAR-LN system of the invention.

In exemplary embodiments, the invention includes a system and method for automatically localizing lymph node stations in an image. Such method includes the steps of gathering image data from patient image sets, manually delineating on the patient image sets various lymph node stations following a standard definition of the lymph node stations, building at least one hierarchical fuzzy anatomy model of the lymph node stations from the delineations on the patient image sets, and automatically locating the lymph node stations on an image of the patient's thorax using at least one hierarchical fuzzy anatomy model. The patient image sets may comprise CT images of the patient's thorax, for example. In an exemplary embodiment, the standard definition of the lymph node stations follows the IASLC standard definitions.

In the exemplary embodiments, the method includes building the lymph node stations as 3D objects. The method may also use object recognition algorithms to locate the lymph node stations. Such object recognition algorithms may include a thresholded optimal search algorithm to refine object pose by an optimal search based on thresholding a test image and an algorithm implementing a one shot method to recognize different objects in a test image. These algorithms may both be used to perform a thresholded optimal search for a first set of objects and a one-shot method to search for a second set of objects.

The invention also applies the AAR methodology described herein to provide a medical imaging algorithm, and its related software, for providing the necessary quality (efficiency, throughput, reproducibility and accuracy) of organ delineation such that an adaptive Radiation Therapy (RT) treatment plan can be developed for use with adaptive RT methods like intensity modulated radiotherapy (IMRT) and Proton Beam Radiation Therapy (PBRT) for use with Computer Tomography (CT) and other imaging modalities. The delineation method addresses an entire body region, and all organs within a region using the Automatic Anatomy Recognition (AAR) methodology described herein. As noted herein, AAR uses Fuzzy Modeling, not the more common statistical framework, and encodes prior information about individual objects and their relationship to other objects, both locally and globally within the anatomical region. This enhances object recognition/localization and delineation to improve the accuracy of treatment planning by allowing the treatment plans to be modified to account for anatomic changes occurring during the course of fractionated radiation therapy over several weeks due to weight loss or deformation of tumor and normal tissues.

In an exemplary embodiment, the invention provides a computerized method of providing radiation therapy planning in patients receiving radiation treatment by: (a) building a fuzzy anatomy model of the body region of interest from an existing set of patient images for the body region; (b) obtaining a pretreatment image of a particular patient body region of interest that is to receive radiation therapy; (c) using automatic anatomy recognition (AAR) to recognize and delineate objects in the particular patient body region of interest; and (d) providing contours of delineated objects as input to radiation treatment planning software. Steps (b)-(d) may be repeated prior to respective patient visits for radiation therapy in order to assess changes between visits.

A radiation therapy system may also be provided that provides radiation therapy planning in patients receiving radiation treatment in accordance with such a method. Such a system nominally includes a database that stores image data from patient image sets, an imaging device that obtains a pretreatment image of a particular patient body region of interest that is to receive radiation therapy, radiation treatment planning software that controls a device for applying radiation to the body region of interest, a memory storing computer instructions for implementing the method, and a processor that processes the computer instructions to build a fuzzy anatomy model of the body region of interest from existing patient image sets for the body region, to recognize and to delineate objects in the particular patient body region of interest using automatic anatomy recognition (AAR), and to provide contours of delineated objects as input to the radiation treatment planning software. The processor may further implement algorithms for implementing the AAR techniques described above as well as abdominal fat quantification and automatic recognition of lymph node stations in images of the thoracic region of a patient as described herein.

These and other characteristic features of the invention will be apparent from the following detailed description of the invention.

BRIEF DESCRIPTION OF THE DRAWINGS

The present application is further understood when read in conjunction with the appended drawings. For the purpose of illustrating the subject matter, there are shown in the drawings exemplary embodiments of the subject matter; however, the presently disclosed subject matter is not limited to the specific methods, devices, and systems disclosed. In addition, the drawings are not necessarily drawn to scale. In the drawings.

DETAILED DESCRIPTION OF ILLUSTRATIVE EMBODIMENTS

Figure 1:
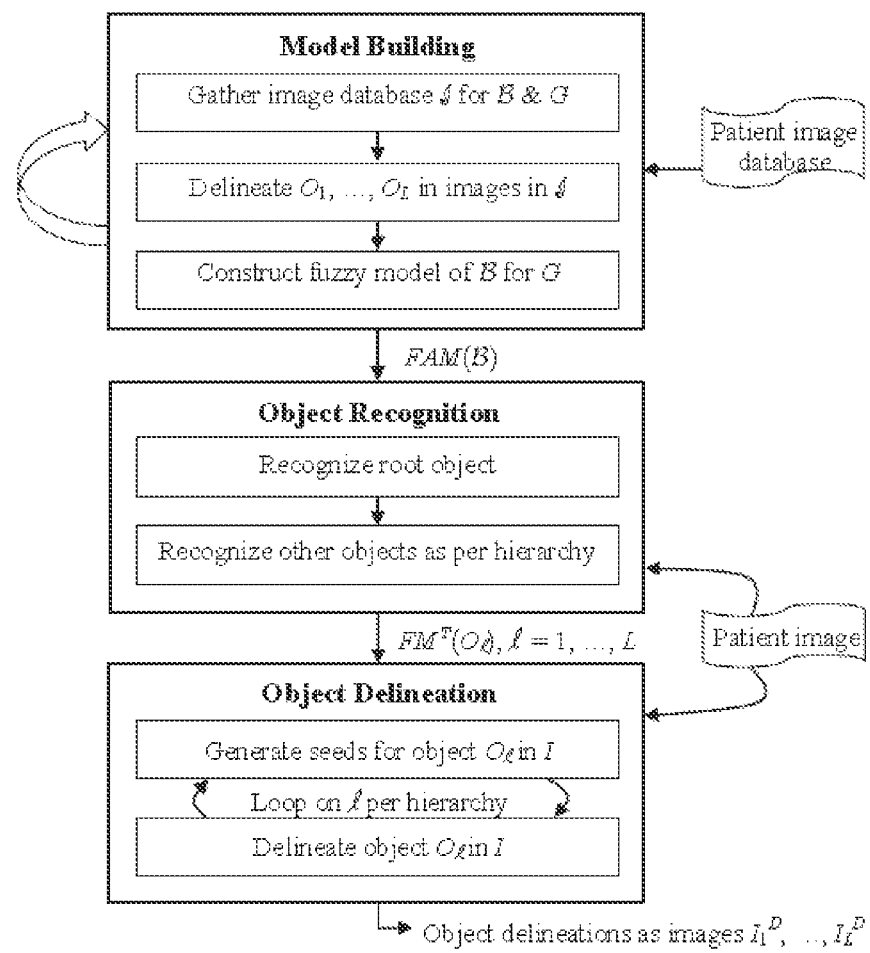
FIG. 1 illustrates a schematic representation of the AAR schema showing the three main steps of model building, object recognition, and object delineation.

Certain specific details are set forth in the following description with respect to FIGS. 1-30 to provide a thorough understanding of various embodiments of the invention. Certain well-known details are not set forth in the following disclosure, however, to avoid unnecessarily obscuring the various embodiments of the invention. Those of ordinary skill in the relevant art will understand that they can practice other embodiments of the invention without one or more of the details described below. Also, while various methods are described with reference to steps and sequences in the following disclosure, the description is intended to provide a clear implementation of embodiments of the invention, and the steps and sequences of steps should not be taken as required to practice the invention.

In the detailed description to follow, the AAR methodology for automatic anatomy recognition for different body regions will be described. Then, examples will be provided for implementing the AAR methodology to quantify abdominal fat, provide automatic localization of IASLC-defined mediastinal lymph node stations, and radiation therapy planning in exemplary embodiments.

Building Fuzzy Model of Body Region B
Notations and Overall Approach

As described herein, the AAR approach has five unique characteristics: (1) direct hierarchical codification of the prior object geographic and geometric relationship information; (2) a "what-you-see-is-what-you-get" entirely digital fuzzy modeling strategy; (3) hierarchical object recognition strategies that go from a broader gestalt to narrower specifics in locating objects; (4) demonstrated generality of applicability of the same approach to different organ systems, body regions, and modalities; and (5) adaptability of the system to different applications. The AAR approach of the invention is graphically summarized in FIG. 1. As illustrated, the body is divided into body regions $B_1, \ldots, B_K$. Models are built for each specific body region $B \in \{B_1, \ldots, B_K\}$ and each population group G (whatever way G is defined). Throughout this description, B and G are treated as variables, and each body region is considered separately and independent of other body regions. The three main blocks in FIG. 1 correspond to model building, object recognition, and object delineation. A fuzzy model $FM(O_l)$ is built separately for each of the L objects $O_l$ in B, and these models are integrated into a hierarchy chosen for B. The output of the first step is a fuzzy anatomic model $FAM(B, G)$ of the body region B for group G. This model is utilized in recognizing objects in a given patient image I of B belonging to G in the second step. The hierarchical order is followed in this process. The output of this step is the set of transformed fuzzy models $FM^T(O_l)$ corresponding to the state when the objects are recognized in I. These modified models and the image I form the input to the third step of object delineation which also follows the hierarchical order. The final output is in the form of delineated objects $O_1^D, \ldots, O_L^D$, where each $O_l^D$ is a binary image.

The following notation is used herein. G: the population group under consideration. B: the body region of focus. $O_1, \ldots, O_L$: L objects or organs of B (such as esophagus, pericardium, etc. for B=Thorax). $\mathcal{I} = \{I_1, \ldots, I_N\}$: the set of images of B for G from N subjects which are used for model building and for training the parameters of the AAR algorithms. $I_{n,l}$: the binary image representing the true delineation of object $O_l$ in the image $I_n \in \mathcal{I}$. $\mathcal{I}^b = \{I_{n,l}: 1 \leq n \leq N \ \& \ 1 \leq l \leq L\}$ is the set of all binary images used for model building. $FM(O_l)$: Fuzzy model of object $O_l$ derived from the set of all binary images $\mathcal{I}_l^b = \{I_{n,l}: 1 \leq n \leq N\}$ of $O_l$. $FAM(B, G)$: Fuzzy anatomy model of the whole object assembly in B with its hierarchy. $FM^T(O_l)$: Transformed (adjusted) $FM(O_l)$ corresponding to the state when $O_l$ is recognized in a given patient image I. $O_l^D$: Delineation of $O_l$ in I represented as a binary image. Any image I will be represented by a pair $I = (C, f)$, where C denotes a 3D rectangular array of voxels, and f is a mapping $f: C \rightarrow \mathbb{I}$ where $\mathbb{I}$ is a set of integers (except when dealing with fuzzy sets, which are also expressed as images for computational purposes, in which case $\mathbb{I}$ is a set of real numbers) denoting the image intensities. For any binary image $J = (C, f_b)$, PAS(J) will be used to denote the principal axes system derived from the set X of voxels of J with value 1. PAS(J) is described by the geometric center of X and the eigenvectors derived from X via principal component analysis.

The following description will follow the schematic of FIG. 1. Table 1 below lists brief anatomic definitions of all objects from all three body regions considered herein.

TABLE 1

| | | Anatomic definitions of organs |
|---|---|---|
| | Acronym | Definition of object. |
| Thoracic objects | | |
| Thoracic skin | TSkn | The outer boundary of the thoracic skin (arms excluded). The interior region constitutes the entire thoracic body region. The inferior boundary is defined to be 5 mm below the base of the lungs and the superior boundary is defined to be 15 mm above the lung apices. |
| Thoracic skeleton | TSk | All skeletal structures contained in the thoracic body region, including the spine, ribs, sternum, and the portions of the scapulae and clavicles that are inside the body region. |
| Respiratory system | RS | Grouping of RPS, LPS, and TB. |
| Right lung | RPS | The outer boundary of the right lung along the right pleura. |
| Left lung | LPS | The outer boundary of the left lung along the left pleura. |
| Trachea and bronchi | TB | The outer boundary of the trachea and bronchi from the superior thoracic trachea to the distal main stem bronchi. |
| Internal mediastinum | IMS | Grouping of PC, E, AS, and VS. |
| Pericardial region | PC | Region within the boundary of pericardial sac. The superior aspect is defined by the branching of the main pulmonary artery. |
| Esophagus | E | The outer boundary of the esophagus from the superior aspect of thorax to the level of gastric cardia. |
| Arterial system | AS | The outer boundary of the ascending aorta, aortic arch, descending thoracic aorta, pulmonary arteries, innominate artery, proximal left common carotid artery, and proximal left subclavian artery. The superior aspect is defined by the branching of the innominate artery. |
| Venous system | VS | The outer boundary of the superior vena cava, right and left brachiocephalic veins, and azygos vein. |
| Abdominal objects | | |
| Abdominal skin | ASkn | The outer boundary of the abdominal skin. The interior region constitutes the entire abdominal body region. The superior boundary is defined by the superior aspect of the liver. The inferior boundary is defined by the bifurcation of the abdominal aorta into the common iliac arteries. |
| Abdominal skeleton | ASk | All skeletal structures contained in the abdominal body region, including lumbar spine and portion of the inferior ribs within the body region. |
| Soft tissue | ASTs | Grouping of Kd, Spl, Msl, AIA, IVC. |
| Kidneys | Kd | Grouping of RKd and LKd. |

TABLE 1-continued

Anatomic definitions of organs

| | Acronym | Definition of object. |
|---|---|---|
| Right kidney | RKd | The outer boundary of the right kidney. All external blood vessels are excluded. |
| Left kidney | LKd | The outer boundary of the left kidney. All external blood vessels are excluded. |
| Spleen | Spl | The outer boundary of the spleen. All external blood vessels are excluded. |
| Muscle | Msl | The outer boundaries of the abdominal musculature, including the rectus abdominis, abdominal oblique, psoas, and paraspinal muscles. |
| Abdominal aorta | AIA | The outer boundary of the abdominal aorta. The superior and inferior slices of AIA are the same as those of the abdominal region. |
| Inferior vena cava | IVC | The outer boundary of the inferior vena cava. The superior and inferior slices of IVC are the same as those of the abdominal region. |
| Liver | Lvr | The outer boundary of the liver. The intrahepatic portal veins and hepatic arteries are included in this region. |
| Fat | Fat | Grouping of SAT and VAT |
| Subcutaneous adipose tissue | SAT | Adipose tissue in the subcutaneous region in the abdomen. |
| Visceral adipose tissue | VAT | Adipose tissue internal to the abdominal musculature. |
| Neck Objects | | |
| Head and Neck skin | NSkn | The outer boundary of the head and neck skin, where the interior region constitutes the entire head and neck body region. The superior boundary is defined by a level 6.6 mm above the superior aspect of the globes. The inferior boundary is defined by a level 6.6 mm inferior to the inferior aspect of the mandible. |
| Air and Bone | A&B | Grouping of Mnd and Phrs. |
| Mandible | Mnd | The outer boundary of the mandible. |
| Pharynx | Phrx | Grouping of NP and OP. |
| Nasopharyngeal airway | NP | The outer contour of the nasal and nasopharyngeal air cavity, extending to the inferior aspect of the soft palate. |
| Oropharyngeal airway | OP | The outer contour of the oropharyngeal air cavities, extending from the inferior aspect of the soft palate to the superior aspect of the epiglottis. |
| Fat pad | FP | The outer boundary of the parapharyngeal fat pad. |
| Neck soft tissues | NSTs | Grouping of Tnsl, Tng, SP, Ad. |
| Palatine tonsils | Tnsl | Grouping of RT and LT. |
| Right palatine tonsil | RT | The outer boundary of the right palatine tonsil. |
| Left palatine tonsil | LT | The outer boundary of the left palatine tonsil. |
| Tongue | Tng | The outer boundary of the tongue. |
| Soft palate | SP | The outer boundary of the soft palate. |
| Adenoid tissue | Ad | The outer boundary of the adenoid tissue. |

Gathering Image Database for B and G

The basic premise of the AAR approach is that the fuzzy anatomic model of B for G should reflect near normal anatomy. Consequently, the cleanest way of gathering image data for model building will be to prospectively acquire image data in a well-defined manner from subjects in group G who are certified to be near normal. Such an approach would be expensive and may involve radiation exposure (in case of CT imaging). For developing the concepts and testing the feasibility of AAR, therefore, the inventors have taken a vastly less expensive and simpler approach of utilizing existing human subject image data sets. For the thoracic and abdominal body regions, a board certified radiologist (co-author DAT) selected all image data sets (CT) from the health system patient image database in such a manner that the images appeared radiologically normal for the body region considered, with exception of minimal incidental focal abnormalities such as cysts, small pulmonary nodules, etc. Images with severe motion/streak artifacts or other limitations were excluded from consideration. For these two body regions, the population groups considered have an age range of approximately 50-60 years. This age range was selected to maximize the chances of finding sufficient number of near normal images. For the neck body region, the inventors utilized image data (MR1) previously acquired from normal subjects for the study of pediatric upper airway disorders. G in this instance is female subjects in the age range of 7-18. The modeling schema is such that the population variables can be defined at any desired "resolution" in the future and the model can then be updated when more data are added.

Some organs in B are better defined in a slice plane different from the slice plane used for imaging others. For example, for B=neck, the best plane for slice imaging is sagittal for tongue and soft palate, while for the upper airways and other surrounding organs, axial slices are preferred. The AAR methodology automatically handles organs defined in images with different orientations of digitization by representing image and object data in a fixed and common scanner coordinate system of reference.

Delineating Objects of B in the Images in the Database

There are two aspects to this task—forming an operational definition of both B and the organs in B in terms of their precise anatomic extent, and then delineating the objects following the definition. These considerations are important for building consistent and reliable models, and, in the future, if similar efforts and results for body-wide models are to be combined, exchanged, and standardized.

Definition of body regions and objects: Each body region is defined consistently in terms of a starting and ending anatomic location. For axial slice data, these locations are determined in terms of transverse slice positions. For example, for B=Thorax, the body region is considered to extend axially from 5 mm below the base of the lungs to 15 mm above the apex of the lungs. Arms are not included in this study. For other orientations of slice planes in slice imaging, the same definitions are applied but translated into other planes. Similarly, each object included in B is defined precisely irrespective of whether it is open-ended—because it straddles body regions (for example, esophagus)—or closed and contained within B but is contiguous with other objects (for example, liver with hepatic portal vein, common hepatic artery, and bile duct). For each body region, the inventors have created a document that delineates its precise definition and the specification of the components and boundaries of its objects. This document is used as a reference by all involved in generating data sets for model building. These definitions are summarized in Table 1 above.

Each body region is carved out manually, following its definition, from the data sets gathered for it. In the notation herein, $\mathcal{J}$ denotes the resulting set of such standard images that precisely cover B as per definition. The inventors assume the scanner coordinate system, SCS, as a common reference system with respect to which all coordinates will be expressed.

Delineation of objects: The objects of B are delineated in the images of j, adhering to their definition, by a combination of methods including live wire, iterative live wire (Souza, A., and Udupa, J. K., 2006. Iterative live wire and live snake: New user-steered 3D image segmentation paradigms, SPIE Medical Imaging. SPIE, pp. 1159-1165), thresholding, and manual painting, tracing and correction. To minimize human labor and to maximize precision and accuracy, algorithms in terms of a proper combination of these methods and the order in which objects are delineated are devised first, all of which operate under human supervision and interaction. For illustration, in the abdomen, to delineate subcutaneous adipose tissues (SAT) as an object, the skin outer boundary ASkn (as an object) is first segmented by using the iterative live wire method. Iterative live wire is a version of live wire in which once the object is segmented in one slice, the user commands next slice, the live wire then operates automatically in the next slice, and the process is continued until automatic tracing fails when the user resorts to interactive live wire again, and so on. Subsequently, the interface between the subcutaneous and visceral adipose compartments is delineated by using also the iterative live wire method. Once these two object boundaries are delineated, the subcutaneous and visceral components are delineated automatically by using thresholding and morphological operations. On MR images, the same approach works if background non-uniformity correction and intensity standardization (Nyul, L. G., Udupa, J. K., 1999. On standardizing the MR image intensity scale. Magnetic Resonance in Medicine 42, 1072-1081) are applied first to the images in $\mathcal{J}$. If direct delineation by manual tracing or even by using live wire is employed, the process would become complicated (because of the complex shape of the adipose and visceral compartments) and much more labor intensive.

Because of the enormity of this task, a number of trainees, some with medical and biomedical but some with engineering background, were involved in accomplishing this task. All tracings were examined for accuracy by several checks—3D surface renditions of objects from each subject in various object combinations as well as a slice-by-slice verification of the delineations overlaid on the gray images for all images. The set of binary images generated in this step for all objects is denoted by $\mathcal{J}^b = \{I_{n,l}: 1 \le n \le N \ \& \ 1 \le l \le L\}$. The set of binary images generated just for object $O_l$ is denoted by $\mathcal{J}^b_l = \{I_{n,l}: 1 \le n \le N\}$.

Constructing Fuzzy Object Models

The Fuzzy Anatomy Model FAM(B, G) of any body region B for group G is defined to be a quintuple:

$$FAM(B,G) = (H, M, \rho, \lambda, \eta). \qquad (1)$$

Figure 2:
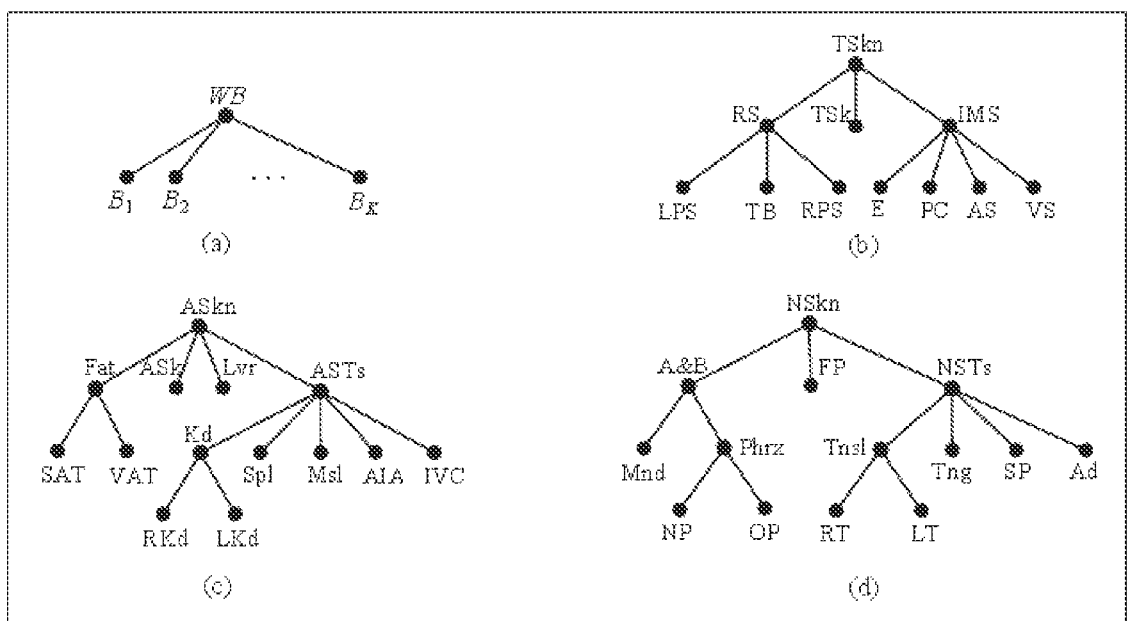
FIG. 2 illustrates the hierarchies devised for the three body regions studied, where H is a hierarchy, represented as a tree, of the objects in a body region B

Briefly, the meaning of the five elements of FAM(B, G) is as follows. H is a hierarchy, represented as a tree, of the objects in B as illustrated in FIG. 2. M is a collection of fuzzy models, one model per object in B. ρ describes the parent-to-offspring relationship in H over G. λ is a set of scale factor ranges indicating the size variation of each object $O_l$ over G. η represents a set of measurements pertaining to the objects in B. A detailed description of these elements and the manner in which FAM(B, G) is derived from $\mathcal{J}$ and $\mathcal{J}^b$ are presented below.

Hierarchy H: This element describes the way the objects of B are considered ordered anatomically as a tree structure. This order currently specifies the inclusion of an offspring object $O_k$ anatomically in the parent object $O_l$ though other arrangements are possible for H. While each B has its own hierarchy, B itself forms the offspring of a root denoting the whole body, WB, as shown in FIG. 2. FIG. 2(a) illustrates the hierarchy for whole body WB, while FIG. 2(b) illustrates the hierarchy for the Thorax, where TSkn: Outer boundary of thoracic skin as an object; RS: Respiratory System; TSk: Thoracic Skeleton; IMS: Internal Mediastinum; RPS, LPS: Right & Left Pleural Spaces; TB: Trachea & Bronchi; E: Esophagus; PC: Pericardium; AS, VS: Arterial & Venous Systems. FIG. 2(c) illustrates the hierarchy for the Abdomen, where ASkn: Outer boundary of abdominal skin; ASk: Abdominal Skeleton; Lvr: Liver; ASTs: Abdominal Soft Tissues; SAT & VAT: Subcutaneous and Visceral Adipose Tissues; Kd: Kidneys; Spl: Spleen; Msl: Muscle; MA: Aorta and Iliac arteries; IVC: Inferior Vena Cava; RKd & LKd: Right and Left Kidneys. FIG. 2(d) illustrates the hierarchy for the Neck, where NSkn: Outer boundary of skin in neck; A&B: Air & Bone; FP: Fat Pad; NSTs: Soft Tissues in neck; Mnd: Mandible; Phrx: Pharynx; Tnsl: Tonsils; Tng: Tongue; SP: Soft Palate; Ad: Adenoid; NP & OP: Nasopharynx and Oropharynx; RT & LT: Right and Left Tonsils.

An object that is exactly a union of its offspring will be referred to herein as a composite object. Examples: RS, Fat, Kd, etc. Note that none of the skin objects is a composite object since the full body region inside the skin is not fully accounted for by the union of the offspring objects. The notion of composite objects is useful in combining objects of similar characteristics at a higher level of the hierarchy, which may make object recognition (and delineation) more effective. Thin tubular objects will be called sparse objects: TB, E, AS, VS, AIA, IVC, Phrx, NP, and OP. Compact, blob-like objects will be referred to as non-sparse: TSkn, RS, IMS, LPS, RPS, PC, ASkn, Fat, SAT, VAT, Lvr, Spl, Kd, RKd, LKd, NSkn, FP, NSTs, Tnsl, Tng, SP, Ad, RT, and LT.

Some objects are a hybrid between these two types, consisting of both features. Examples: TSk, Ask, ASTs, A&B, and Mnd.

Fuzzy model set M: The second element M in the description of FAM(B, G) represents a set of fuzzy models, M={FM ($O_l$): 1≤l≤L}, where FM($O_l$) is expressed as a fuzzy subset of a reference set $\Omega_l \subset Z^3$ defined in the SCS; that is, FM($O_l$)=($\Omega_l$, $\mu_l$). The membership function $\mu_l$(v) defines the degree of membership of voxel v∈$\Omega_l$ in the model of object $O_l$. Ideally, for any l, 1≤l≤L, the inventors would like the different samples of $O_l$ in different subjects to differ by a transformation $A_{n,l}$ involving translation, rotation, and isotropic scaling. The idea behind the concept of the fuzzy model of an object is to codify the spatial variations in form from this ideal that may exist among the N samples of the object as a spatial fuzzy set, while also retaining the spatial relationship among objects in the hierarchical order.

Given the training set of binary images $\mathcal{J}^b_l$ of object $O_l$, the inventors determine $A_{n,l}$, $\mu_l$, and FM($O_l$) for $O_l$ as follows. The inventors permit only such alignment operations, mimicking $A_{n,l}$, among the members of $\mathcal{J}^b_l$, that are executed precisely without involving search and that avoid the uncertainties of local optima associated with optimization-based full-fledged registration schemas. In this spirit, the inventors handle the translation, rotation, and scaling components of $A_{n,l}$ in the following manner.

For translation and rotation, for each manifestation $I_{n,l}$ of $O_l$ in $\mathcal{J}^b_l$, the inventors determine, within SCS, the principal axes system PAS($I_{n,l}$) of $O_l$. Subsequently, all samples are aligned to the mean center and principal axes (though orientation alignment is often not necessary). The scale factor estimation is based on a linear size estimate (in mms) of each sample of De and resizing all samples to the mean size. The size of $O_l$ in $I_{n,l}$ is determined from $\sqrt{e_1+e_2+e_3}$, where $e_1$, $e_2$, and $e_3$ are the eigenvalues corresponding to the principal components of $O_l$ in $I_{n,l}$.

After aligning the members of $\mathcal{J}^b_l$ via $A_{n,l}$ a distance transform is applied to each transformed member for performing shape-based interpolation (Raya, S. P., Udupa, J. K., 1990. Shape-Based Interpolation of Multidimensional Objects. IEEE Transactions on Medical Imaging 9, 32-42; and Maurer, C. R., Qi, R. S., Raghavan, V., 2003. A linear time algorithm for computing exact Euclidean distance transforms of binary images in arbitrary dimensions. IEEE Transactions on Pattern Analysis and Machine Intelligence 25, 265-270). The distances are averaged over all members and converted through a sigmoid function to obtain the membership values $\mu_l$ and subsequently FM($O_l$).

Parent-to-offspring relationship ρ: This element describes the parent-to-offspring spatial relationship in H for all objects in B. Since each object $O_k$ has a unique parent, this relationship is represented by ρ={$\rho_k$: 1≤k≤L} (which also encodes WB to body region relationships, although this is not taken into account in the current implementation). For each $O_k$, $p_k$ codifies the mean position as well as the orientation relationship between $O_k$ and its parent over N samples. The inventors adopt the convention that $\rho_l$ denotes the relationship of the root object of B relative to SCS. Let $GC_{n,l}$ be the geometric center of $O_l$ in $I_{n,l}$. Then, the mean positional relationship $P_{l,k}$ between $O_l$ and $O_k$ is considered to be the mean of the vectors in the set {$GC_{n,k}$−$GC_{n,i}$: 1≤n≤N}. To find the mean orientation $Q_{l,k}$, the inventors make use of the eigenvectors $E^1_{n,l}$, $E^2_{n,l}$, and $E^3_{n,l}$ of the shape of $O_l$ in $I_{n,l}$ estimated over all N samples. The inventors take an average of each $E^i_{n,l}$, over N samples for i=1, 2, 3. However, for some n and i, $E^i_{n,l}$ may be more than 90 degrees from the average, in which case $E^i_{n,l}$ is replaced by −$E^i_{n,l}$ while simultaneously replacing $E^j_{n,l}$ by −$E^j_{n,l}$ for some j different from i so as to keep the system right-handed. The inventors then recalculate the average, and repeat until the eigenvector is within 90 degrees of the average. Then, starting from either the first or the third eigenvector, whichever has the eigenvalue farther from the second, the inventors normalize and make the others orthogonal to it. $Q_{l,k}$ is then taken to be the transformation that aligns the eigenvector system of the parent $O_l$ with that mean orientation. This method guarantees a robust orientation estimate despite the 180-degrees switching property of eigenvectors.

In order not to corrupt $\rho_k$ by the differences in size among subjects, before estimating $\rho_k$, the parent $O_l$ and all offspring objects $O_k$ of $O_l$ are scaled with respect to the center $GC_{n,l}$ of $O_l$ as per a common scale factor, estimated for $O_l$ via the method described above. The reasoning behind this scaling strategy is that an object and its entire offspring should be scaled similarly to retain their positional relationship information correctly.

Scale range λ: The fourth element λ of FAM(B, G) is a set of scale factor ranges, λ={$\Delta_l$=[$\Delta^b_l$, $\lambda^h_l$]: 1≤l≤L}, indicating the size variation of each object $O_l$ over its family $\mathcal{J}^b_l$. This information is used in recognizing $O_l$ in a given image to limit the search space for its pose, as explained in the description of recognizing objects below.

Measurements η: This element represents a set of measurements pertaining to the object assembly in B. Its purpose is to provide a database of normative measurements for future use. This element also serves to improve knowledge about object relationships (in form, geographical layout, etc. in B) and thence in constructing better hierarchies for improving AAR, as explained briefly below.

There are several parameters related to object recognition (next section) and delineation (see below), some of which are image modality specific (They are identified by $T^m_l$ and $Th_l$ in the next section and $\sigma_{\psi o}$, $m_{\psi o}$, $m_{\psi B}$, $\sigma_{\psi O}$ and $\sigma_{\psi B}$ in the following section.) The values of these parameters are also considered part of the description of η. The definition of these parameters and the process of their estimation are described at relevant places in the following sections for ease of reading, although their actual estimation is done at the model building stage.

The fuzzy anatomy model FAM(B, G) output by the model building process is used in performing AAR on any image I of B for group G as described in the following sections.

Recognizing Objects

The process of what is usually referred to as "segmenting an object in an image" may be thought of as consisting of two related phenomena—object recognition (or localization) and object delineation. Recognition is a high-level process of determining the whereabouts of the object in the image. Given this information for the object, its delineation is the meticulous low-level act of precisely indicating the space occupied by the object in the image. The design of the entire AAR methodology is influenced by this conceptual division. The inventors believe that without achieving acceptably accurate recognition it is impossible to obtain good delineation accuracy. The hierarchical concept of organizing the objects for AAR evolved from an understanding of the difficulty involved in automatic object recognition. Once good recognition accuracy is achieved, several avenues for locally confined accurate delineation become available, as discussed in the next section. The goal of recognition in AAR is to output the pose (translation, rotation, and scaling) of FM($O_l$), or equivalently the pose-adjusted fuzzy model $FM^T(O_l)$, for each $O_l$ in a given test image I of $\mathcal{B}$ such that $FM^T(O_l)$ matches the information about $O_l$ present in I optimally.

The recognition process proceeds hierarchically as outlined in the procedure AAR-R presented below. In Step $R_1$, the root object is recognized first by calling algorithm R-ROOT. The inventors assume that the field of view in I fully encloses the root object. For the hierarchies shown in FIG. 2, the root object is the skin outer boundary which is typically more-or-less, although not perfectly, fully included within the imaging field of view. Proceeding down the tree represented by H in the breadth-first order, other objects are recognized by calling algorithm R-OBJECT. The latter makes essential use of the parent fuzzy model and the parent-to-offspring relationship p encoded in FAM(B, G).

| | Procedure AAR-R |
|---|---|
| Input: | An image I of $\mathcal{B}$, FAM($\mathcal{B}$, G). |
| Output: | $FM^T(O_\ell)$, $\ell = 1, ..., L$. |
| Begin | |
| R1. | Call R-ROOT to recognize the root object in H; |
| R2. | Repeat |
| R3. | Find the next offspring $O_k$ to recognize in H (see text); |
| R4. | Knowing $FM^T(O_\ell)$, $\rho_k$, and $\lambda_k$, call R-OBJECT to recognize $O_k$; |
| R5. | Until all objects are covered in H; |
| R6. | Output $FM^T(O_\ell)$, $\ell = 1, ..., L$; |
| End | |

Two strategies are described here for each of algorithms R-ROOT and R-OBJECT. The first, a global approach, does not involve searching for the best pose. The inventors call this the One-Shot Method since the model pose is determined directly by combining the prior information stored in FAM(B, G) and information quickly gathered from the given image I. The one-shot method is used as initialization for a more refined second method called Thresholded Optimal Search.

One-Shot Method

A threshold interval $Th_l$ corresponding to the root object $O_l$ is applied to I followed by a morphological opening operation to roughly segment $O_l$ to produce a binary image J. The purpose of the morphological operation is to exclude as much as possible any significant extraneous material, such as the scanner table and patient clothing, from J. Then the transformed model $FM^T(O_l)$ is found by applying a transformation $T_l^m$ to $FM(P_l)$. $T_l^m$ is devised to express the mean relationship between the roughly segmented $O_l$ and the true segmentation of $O_l$ represented in the binary images $I_{n,l} \in \mathcal{J}^b$. The estimation of $T_l^m$ is done at the model building stage of AAR as mentioned above. To determine $T_l^m$, similar thresholding and morphological operations are performed on each gray image $I_n$ in the training set to obtain a rough segmentation of $O_l$, denoted $J_{n,l}$ in $I_n$. The relationship between this rough segmentation $J_{n,l}$ and the true segmentation $I_{n,l}$ of $O_l$ in $\mathcal{J}^b$ is found as a transformation $T_{n,l}$ that maps $PAS(J_{n,l})$ to $PAS(I_{n,l})$. The mean, denoted $T_l^m$, of such transformations over all training images is then found.

Once the root object $O_l$ is recognized, the poses for other objects in I in the hierarchy H are determined by combining (in the sense of composition) $T_l^m$ with the parent to offspring relationship information stored in $\rho_k$ for each parent-offspring pair. The transformed models $FM^T(O_l)$ are then found from this information. T Thresholded Optimal Search

[This is a strategy to refine the results obtained from the one-shot method. Its premise is that the overall image intensity of the objects in B can be characterized by threshold intervals such that, at the model's pose corresponding to the best match of the model with an underlying object in the given test image I, the mismatch between the thresholded result and the model is minimal. For MR images for this approach to make sense, it is essential to correct for background intensity non-uniformities first followed by intensity standardization (Nyul and Udupa 1999).

Suppose that at the model building stage, the optimal threshold interval $Th_l$ for each object $O_l$ has already been determined automatically from the training image set. It will be explained below as to how this is accomplished. Then, at the recognition stage, the threshold for $O_l$ is fixed at this learned value $Th_l$. Starting from the initial pose found by the one-shot method, a search is made within the pose space for an optimal pose p* of the fuzzy model over I that yields the smallest sum of the volume of false positive and false negative regions, where the model itself is taken as the reference for defining false positive and negative regions. Specifically, let $FM^P(O_l)$ denote the fuzzy model of $O_l$ at any pose p, expressed as an image, and let J denote the binary image resulting from thresholding I at $Th_l$. Then:

$$p^* \in \underset{p}{\operatorname{argmin}}(|FM^P(O_\ell) - J| + |J - FM^P(O_\ell)|). \quad (2)$$

Since arg min is a set, "∈" means one of the values chosen from the set is assigned to p*. Image subtraction here is done in the sense of fuzzy logic, and |x| denotes the fuzzy cardinality of x, meaning that it represents the sum total of the membership values in x. The search space to find p* is limited to a region around the initial pose. This region is determined from knowledge of $\rho_k$ and its variation and the scale factor range $\lambda_k$. For the positional vector, the inventors search in an ellipsoid with its axes in the coordinate axis directions and with length four times the standard deviation of the corresponding coordinate. When searching in orientation space, the inventors search in an ellipsoid with its axes in the direction of the eigenvectors of the rotation vector distribution (covariance matrix) and with length four times the square root of the corresponding eigenvalue. (A rotation vector has magnitude equal to the angle of rotation and direction along the axis of right-handed rotation. The rotation referred to is the rotation of $Q_{l,k}$ required to bring it into coincidence with $E^i_{n,l}$.) For the scale factor, the inventors search in an interval of size four times the standard deviation of the scale factor.

Determining $Th_l$ at the model building stage: To estimate $Th_l$, the inventors run a rehearsal of the recognition method described above as follows, essentially for attempting to learn the recognition process. Imagine the inventors already built M and estimated $\rho$ and $\lambda$. Suppose that the recognition process is now run on the training images. Since the optimal threshold is not known but the true segmentations are known, the idea behind this learning of the recognition process is to test recognition efficacy for each of a number of threshold intervals t and then select the interval $Th_l$ that yields the best match of the model with the known true segmentations for each $O_l$. That is, if $J_n(t)$ is the binary image resulting from thresholding the training image $I_n$ at t, then:

$$Th_\ell \in \underset{p,t}{\operatorname{argmin}} \sum_n |(J_n(t) \times FM^P(O_\ell)) - I_{n,\ell}| + |I_{n,\ell} - (J_n(t) \times FM^P(O_\ell))|. \quad (3)$$

Here, x denotes fuzzy intersection. In words, the optimal threshold $Th_l$ is found by searching over the pose space over all training data sets and all thresholds the best match between the true segmentation of $O_l$ with the result of thresholding $I_n$ restricted to the model. In the present implementation, 81 different values of the intervals are searched (9 for each end of the interval). The 9 positions for the lower end are the $5^{th}$, $10^{th}$, ..., $45^{th}$ percentile values of the cumulative object intensity histogram determined from the training image set. Similarly, for the upper end, the positions are $55^{th}$ to $95^{th}$ percentile values.

To summarize, the thresholded optimal search method starts the search process from the initial pose found by the one-shot method. It uses the optimal threshold values $Th_l$ determined at the training stage for each object $O_l$ and finds the best pose for the fuzzy model of $O_l$ in the given image I by optimally matching the model with the thresholded version of I. The only parameters involved in the entire recognition process are the thresholds $Th_l$, one threshold interval per object, and $T_l^m$. Their values are automatically determined in the model building stage from image and binary image sets $\mathcal{I}$ and $\mathcal{I}^b$ and they become part of the model FAM(B, G) itself.

Delineating Objects

Once the recognition process is completed and the adjusted models $FM^T(O_l)$ are output for a given image I of $\mathcal{B}$, delineation of objects is performed on I in the hierarchical order as outlined in the procedure AAR-D. As in recognition, in Step D1, the root object is first delineated by calling D-ROOT. AAR-D then proceeds in the breadth-first order to delineate other objects by calling D-OBJECT.

| Procedure AAR-D | |
|---|---|
| Input: | An image I of $\mathcal{B}$, FAM($\mathcal{B}$, G), $FM^T(O_\ell)$, $\ell$ = 1, ..., L. |
| Output: | $O_\ell^D$, $\ell$ = 1, ..., L. |
| Begin | |
| D1. | Call D-ROOT to delineate the root object in H; |
| D2. | Repeat |
| D3. | Traverse H and find the next offspring $O_k$ to delineate in H; |
| D4. | Knowing delineation of $O_\ell$, call D-OBJECT to delineate $O_k$ in I; |
| D5. | Until all objects are covered in H; |
| D6. | Output $O_\ell^D$, $\ell$ = 1, ..., L; |
| End | |

For D-ROOT and D-OBJECT, the inventors have chosen an algorithm from the fuzzy connectedness (FC) family in view of the natural and intimate adaptability of the FC methods to prior information coming in the form of fuzzy sets. In particular, since the inventors focus on the problem of delineating one object at a time, for both Steps D1 and D4, the inventors have selected the linear-time Iterative Relative FC (IRFC) algorithm of Ciesielski, K. C., Udupa, J. K., Falcao, A. X., Miranda, P. A. V., 2012. Fuzzy Connectedness Image Segmentation in Graph Cut Formulation: A Linear-Time Algorithm and a Comparative Analysis. Journal of Mathematical Imaging and Vision 44, 375-398, for separating each object $O_l$ from its background. The novel adaptations are in incorporating fuzzy model information into the IRFC formulation and in making the latter fully automatic. These modifications are described below.

Fuzzy Model-Based IRFC (FMIRFC)

There are two aspects that need to be addressed to fully describe the FMIRFC algorithm: affinity function and seed specification. Affinity is a local concept indicating the degree of connectedness of voxels locally in terms of their spatial and intensity nearness. In the FC family, this local property is grown into a global phenomenon of object connectedness through the notion of path strengths.

Affinity function: The FC framework (Udupa and Samara sekera 1996, Ciesielski et al. 2012) is graph-based. An ordered graph (C, α) is associated with the given image I=(C, f) where α is an adjacency relation on C such as 6-, 18-, or 26-adjacency. Each ordered pair (c, d) of adjacent voxels in a is assigned an affinity value k(c, d) which constitutes the weight assigned to arc (c, d) in the graph. To each path π in the graph (or equivalently in I) in the set of all possible paths $\pi_{a,b}$ between two voxels a and b of C, a strength of connectedness K(π) is determined, which is the minimum of the affinities along the path. The connectivity measure K*(a, b) between a and b is then defined to be K*(a, b)=max{K(π): π∈$\pi_{a,b}$}. The notion of connectivity measure can be generalized to the case of "between a set A and a voxel b" by a slight modification: K*(A, b)=max{K(π): π∈$\pi_{a,b}$ & α∈ A}. By using a fast algorithm to compute K*(A, b), the machinery of FC allows a variety of approaches to define and compute "objects" in images by specifying appropriate affinity functions and seed sets. In particular, in IRFC, two seed sets $A_O$ and $A_B$ are indicated for an object O and its background B, respectively. Then the object indicated by $A_O$ is separated optimally from the background indicated by $A_B$ by an iterative competition in connectivity measure between $A_O$ and every voxel c ∈ C and between $A_B$ and c. In published IRFC methods, $A_O$ and $A_B$ are specified usually with human interaction.

In FMIRFC, affinities $K_o(c, d)$ and $K_B(c, d)$ for 0 and B are designed separately. Subsequently, they are combined into a single affinity K by taking a fuzzy union of $K_o$ and $K_B$. Each of $K_o$ and $K_B$ has three components. The description below is for $K_o$. The same applies to $K_B$.

$$K_o(c,a)=w_1\psi_0(c,a)+w_2\varphi_0(c,d)+w_2\gamma_0(c,d). \quad (4)$$

Here, $\psi_0$(c, d) represents a homogeneity component of affinity, meaning, the more similar image intensities f(c) and f(d) are at c and d, the greater is this component of affinity between c and d. As commonly done in the FC literature, the inventors set $$\psi_O(c,d)=\exp[-(f(c)-f(d))^2/2\sigma_{\psi_O}^2], \quad (5)$$

where $\sigma_{\psi_o}$ is a homogeneity parameter that indicates the standard deviation of intensities within object O. $\psi_o$(c, d), the object feature component, on the other hand, describes the "degree of nearness" of the intensities at c and d to the intensity $m_{\psi_o}$ expected for the object O under consideration. Denoting the standard deviation of object intensity by $\sigma_{\psi_o}$, this nearness is expressed by:

$$\varphi_O(c,d)=\exp[-(\max\{(f(c)-m_{\varphi_O})^2,(f(d)-m_{\varphi_O})^2\}^2/2\sigma_{\varphi_O}^2]. \quad (6)$$

The third component $\gamma_o$ incorporates fuzzy model information into affinity by directly taking the larger of the two fuzzy model membership values $\mu_o(c)$ and $\mu_o(d)$ at c and d for the object:

$$\gamma_o(c,d)=\max\{\mu_o(c),\mu_o(d)\}. \quad (7)$$

Finally, a combined single affinity κ on I is constructed by $$\kappa(c,d)=\max\{\kappa_o(c,d),K_B(c,d)\}. \quad (8)$$

The weights in Equation (4) are chosen equal and such that they add up to 1. The homogeneity parameter is set equal for object and background ($\sigma_{\psi_O} = \sigma_{\psi_B}$) and estimated from uniform regions in the training images (after leaving out high gradient regions), as commonly done in the FC literature (Saha and Udupa 2001). The remaining parameters ($\sigma_{\varphi_O}$, $\sigma_{\varphi_B}$, $m_{\varphi_O}$, $m_{\varphi_B}$) are estimated automatically from the training data sets from the knowledge of O and B regions for each object.

Seed specification: Seed sets $A_O$ and $A_B$ are found by a joint criterion of a threshold for image intensity and for model membership for each of O and B. The threshold interval $Th_O$ for O is the same as the one used for recognition, namely $Th_I$. The threshold interval $Th_B$ for background is a union of similar threshold intervals for the background objects. (In principle, all objects other than O can be considered to be background objects of O; however, in practice, only the anatomic neighbors of O matter.) The only new parameters are $Th_O^M$ and $Th_B^M$ used as model thresholds for indicating $A_O$ and $A_B$, respectively. These parameters are used as follows:

---

Algorithm FMIRFC

Input: Image I of $\mathcal{B}$, FAM($\mathcal{B}$, G), $FM^T(O_\ell)$ at recognition. Below, assume O = $O_\ell$.
Output: $O_\ell^D$.
Begin
FC1. Determine background B of O;
FC2. Retrieve affinities $\kappa_O$ and $\kappa_B$ from FAM($\mathcal{B}$, G);
FC3. Compute combined affinity $\kappa$;
FC4. Retrieve thresholds $Th_O$, $Th_B$, $Th_O^M$, and $Th_B^M$ from FAM($\mathcal{B}$, G) and determine seed sets $A_O$ and $A_B$ in I via (9);
FC5. Call the IRFC delineation algorithm with $\kappa$, $A_O$, $A_B$, and I as arguments;
FC6. Output image $O_\ell^D$, returned by the IRFC algorithm;
End

---

$$A_O = \{v \in C : f(v) \in TH_O \& \mu_O(v) \in Th_O^M\},$$

$$A_B = \{v \in C : f(v) \in Th_B \& \mu_B(v) \in Th_B^M\}. \quad (9)$$

In an exemplary implementation, $Th_O^M$ is fixed at [0, 0.9] and [0, 0.5] for non-sparse and sparse objects, respectively, and $Th_B^M$ is set to [0, 0]. The FMIRFC algorithm is summarized above.

Illustrations, Experimental Results and Discussion

Image Data

The data sets used for the three body regions are summarized in Table 2. Data sets DS1 and DS2 are from CT and are selected from a hospital patient image database, and were verified to be of acceptable quality and radiologically normal, with exception of minimal incidental focal abnormalities, in the body regions for which they are chosen. Note the typical clinical resolution for pixel size (~1 mm) and slice spacing (5 mm) in these data sets and hence the challenge for object recognition and delineation. The goal in focusing on these data was to challenge the AAR system to perform on typical clinical data sets. DS3 is from an on-going research project investigating the association of Polycystic Ovary Syndrome with Obstructive Sleep Apnea in obese pediatric female subjects (Arens, R., Sin, S., Nandalike, K., Rieder, J., Khan, U. I., Freeman, K., Wylie-Rosett, J., Lipton, M. L., Wootton, D. M., McDonough, J. M., Shifteh, K., 2011. Upper Airway Structure and Body Fat Composition in Obese Children with Obstructive Sleep Apnea Syndrome. American Journal of Respiratory and Critical Care Medicine 183, 782-787). It consists of both axial and sagittal acquisitions and a mix of T1- and T2-weighted images. DS1-DS3 represent the three body regions for which the hierarchy of organs was depicted in FIG. 2. DS4 (Wagshul, M. E., Sin, S., Lipton, M. L., Shifteh, K., Arens, R., 2013. Novel retrospective, respiratory-gating method enables 3D, high resolution, dynamic imaging of the upper airway during tidal breathing. Magn Reson Med. Doi:10.1002/mrm.24608), however, is used for testing the ability of the AAR method to rapidly prototype an application by using existing models for the same body region. In this case, models built from DS2 from CT are deployed on DS4 from MRI.

TABLE 2

Summary of data sets used in the experiments.

| Data Identifier | Body Region $\mathcal{B}$ | Group G (age) | Number of Subjects N | Image Modality | Imaging Protocol Details | Image Information |
|---|---|---|---|---|---|---|
| DS1 | Thorax | 50-60 male | 50 normal | CT | Contrast-enhanced, axial, breath-hold | 512 × 512 × 51-69, 0.9 × 0.9 × 5 mm³ |
| DS2 | Abdomen | 50-60 male | 50 normal | CT | Contrast-enhanced, axial, breath-hold | 512 × 512 × 38-55, 0.9 × 0.9 × 5 mm³ |
| DS3 | Neck | 8-17 male & female | 15 normal | MRI | T2-weighted, axial & T1- & T2-weighted sagittal. T2: TR/TE = 8274.3/82.6 msec, T1: TR/TE = 517.7/7.6 msec | 400 × 400 × 35-50, 0.5 × 0.5 × 3.3 mm³ |
| DS4 | Abdomen | 8-17 male & female | 14 6 normal, 8 obese patients | MRI | T2-weighted, axial. TR/TE = 1556.9/84 msec | 400 × 400 × 45-50, 0.7 × 0.7 × 6 mm³ |

In all data sets, any extra slices falling outside the body region B as per definition are removed manually first. Note the variation in the size of the body region in Table 2 (expressed roughly as slice spacing×number of slices). In the case of MRI, the resulting images are processed, first to suppress background non-uniformities and subsequently to standardize the image intensities (Nyul and Udupa 1999). Standardization is a post-acquisition image processing technique which significantly minimizes the inter-subject and intra- and inter-scanner image intensity variations for the same tissue and achieves tissue-specific numeric meaning for MR images. It has been shown to significantly improve the accuracy of delineation algorithms (Zhuge, Y., Udupa, J. K., 2009. Intensity standardization simplifies brain MR image segmentation, Computer, Vision and Image Understanding 113, 1095-1103). It is done separately for each MRI protocol and body region. For DS1 and DS2, one half of the image data sets were used for model building, which included the estimation of the parameters of the recognition and delineation algorithms ($T_l^m$, $Th_l$, $\sigma_{\psi O}$, $m_{\varphi B}$, $m_{\varphi B}$, $\sigma_{\varphi O}$, and $\sigma_{\varphi B}$), and the remaining data sets were used for testing the methods. For DS3, the train-test sets were set up as 11 and 4, and this was repeated 30 times for different choices of 11 and 4 data sets. For DS4, all data sets were used for testing, and model building was based on one half of the data sets in DS2. This provided an interesting scenario for the challenge for the AAR method, in that, models built from normal CT data sets for one patient group were used for performing AAR on MRI data sets from normal subjects and patients from another group.

Model Building

Figure 3:
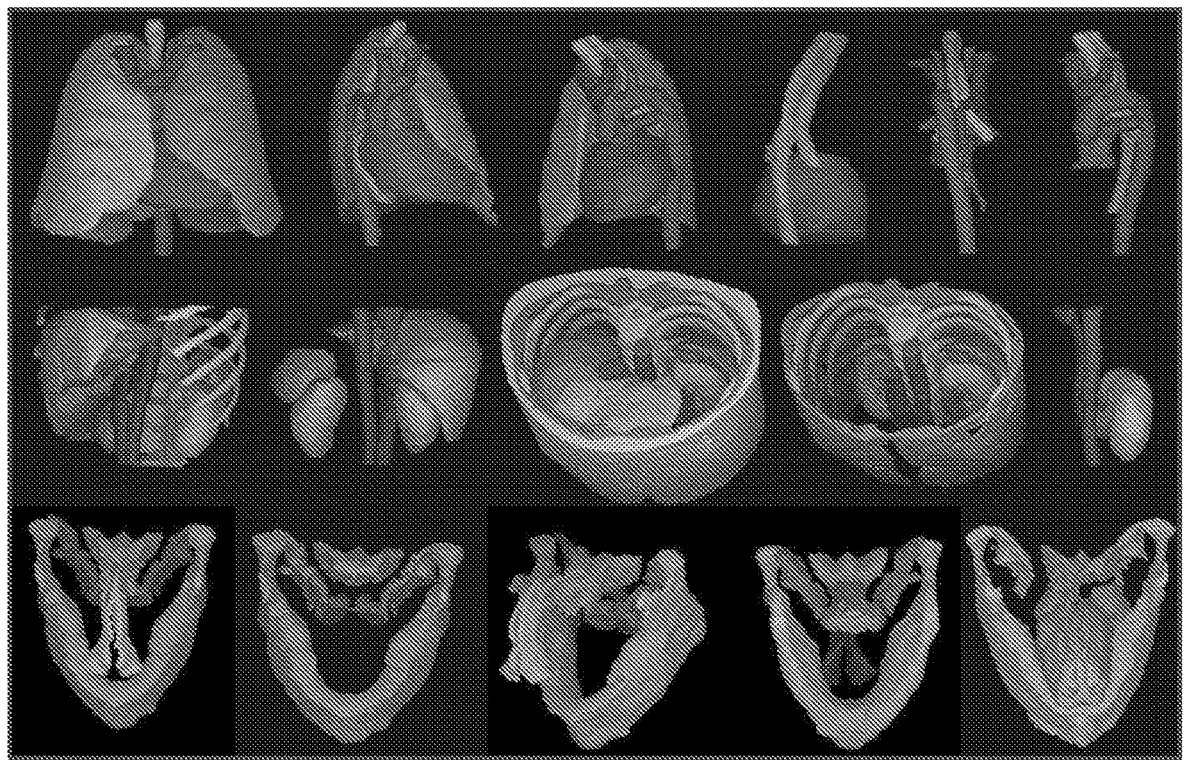
FIG. 3 illustrates organs from one training set for each body region displayed via surface rendering. For each row, objects in one picture are listed as { . . . }. Top row: Thorax. 3rd picture: {RPS, TB, E, AS, VS, PC}. Middle row: Abdomen. 3rd picture: {Ask, Lvr, LKd, IVC, AIA, Spl, SAT, Msl}. Bottom row: Neck. 5th picture: {Mnd, Tng, NP, OP, Ad, FP, Tns1}.

In FIG. 3, the organs defined in the image of one of the subjects employed in model building are displayed for each body region in different combinations of the organs. The inventors have examined all data sets under DS1-DS3 in this manner which has helped in a proper understanding of the organ relationships. This is important for devising effective hierarchies, recognition strategies, and delineation algorithms.

Figure 4:
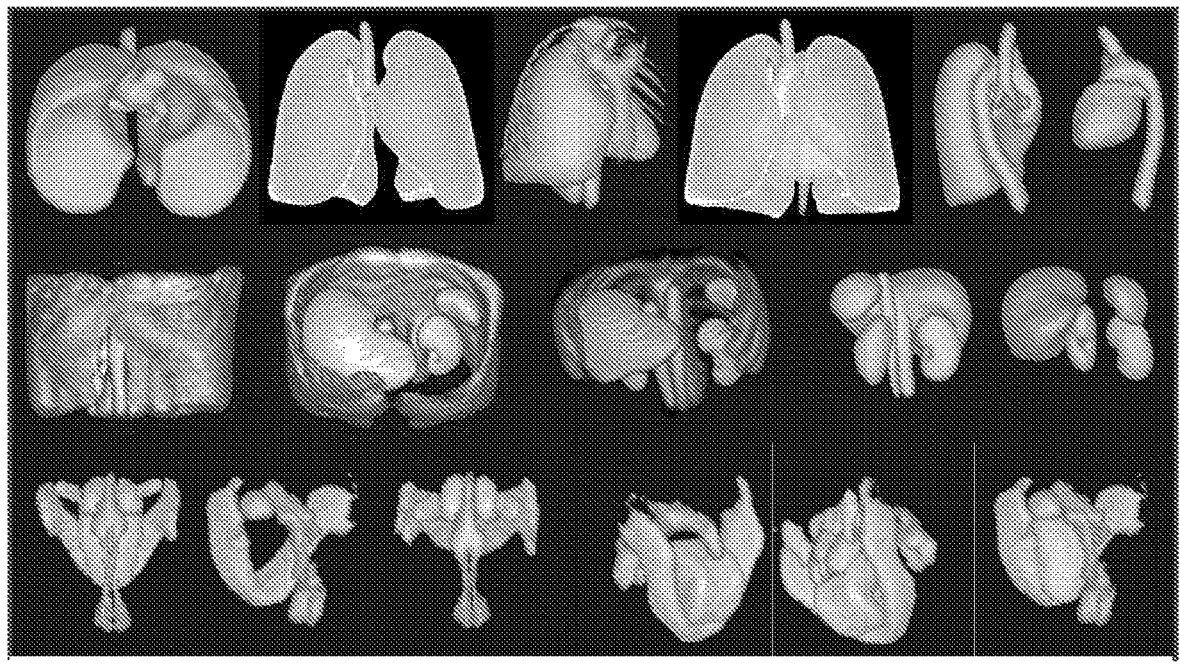
FIG. 4 illustrates volume renditions of fuzzy models of objects in different combinations for the three body regions. For each row, objects in one picture are listed as { . . . }. Top row: Thorax. 5th picture: {LPS, AS, TB}. Middle row: Abdomen. 3rd picture: {ASk, Lvr, LKd, RKd, AIA, IVC, Spl}. Bottom row: Neck. 5th picture: {Mnd, Tng, NP, OP, Ad, FP}.

FIG. 4 displays fuzzy models $FM(O_l)$ of objects in various combinations for the three body regions. Since the volumes are fuzzy, they are volume rendered by using an appropriate opacity function. Note that although the models appear blurred, they portray the overall shape of the objects they represent and the object relationships. From consideration of the difficulties in model building, recognition, and delineation, the inventors divided objects in the body into sparse, non-sparse, and hybrid groups. Sparse objects pose special challenges for recognition and delineation, stemming mostly from difficulties in model building. Variations in the form, shape, and orientation of sparse objects cause them to overlap far less, or often not at all, compared to non-sparse objects, when forming the model by gathering fuzzy overlap information. In other words, the models tend to diffuse or become too fuzzy. For example, in AS (thorax), the descending aortic portion extends from superior to inferior. However, this part is often either bent from the vertical or is crooked, and the pattern of the brachiocephalic and subclavian arteries arising from the aortic arch is different. If the variation is just in orientation only, then aligning by orientation may produce sharper models. But the issue is not one of producing less fuzzy models but of building models that have the right/correct amount of fuzziness so that the recognition process will be least misguided by the model. This dilemma of the disconnection between model building and recognition is common to all model/atlas-based methods and is the real challenge in automatic recognition of sparse and hybrid objects.

Figure 5:
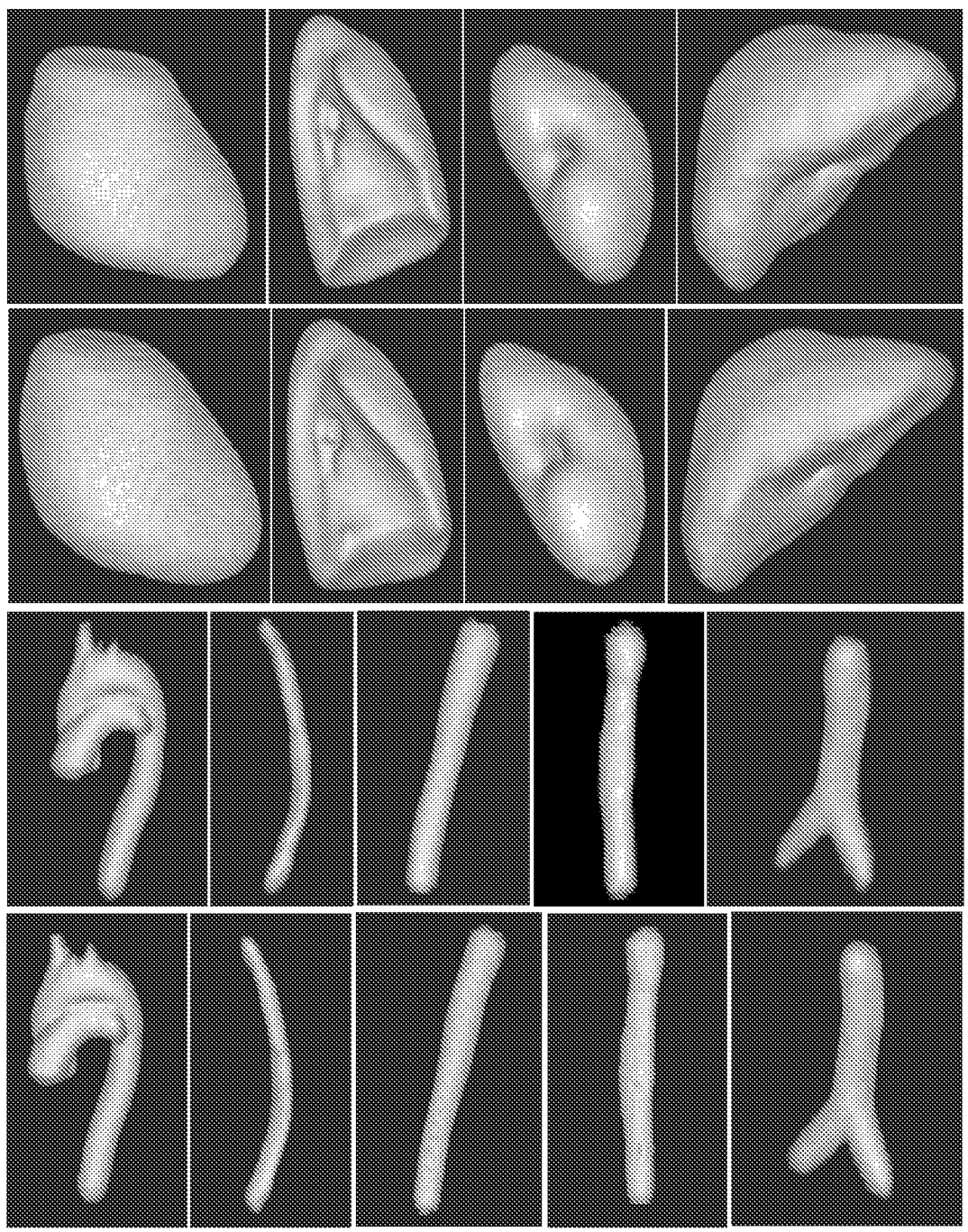
FIG. 5 illustrates volume renditions of fuzzy models created without (Rows 1 and 3) and with (Rows 2 and 4) orientation alignment for several non-sparse (Rows 1 and 2) and sparse (Rows 3 and 4) objects. Row 1: PC, RPS, LKd, Lvr. Row 3: AS, E, AIA, IVC, TB.

To study the effect of orientation alignment, FIG. 5 displays models created without and with orientation adjustment, for several sparse as well as non-sparse objects from all three body regions. The volume renditions were created with exactly the same settings for each object for its two versions of models. Orientation adjustment does not produce any dramatic difference in the models created, although close scrutiny reveals that the model definition improves slightly; examine especially LPS, AIA, AS, and Lvr.

Relating to the fifth element η of FAM(B, G), Tables 3-5 show correlations among objects in their size for the three body regions. Object size is determined as explained above. As may be expected, bilateral organs, such as LPS and RPS, LKd and RKd, and LT and RT, are strongly correlated in size. That is, their sizes go together, whatever way they may be related to the subject's body size. There are also other interesting strong, poor (or no), and even weak negative, correlations, as highlighted in the tables; for example, TSk with RS and RPS; VS with TB, PC, and E; ASkn with ASTs, SAT and Msl; ASTs with SAT and Msl; Ms1 with SAT; NSkn with A&B; Ad with NSkn, FP, NP, and SP. Although the inventors have not explored the utility of such information herein, those skilled in the art will appreciate that this and other information will be useful in devising hierarchies more intelligently than guided by just anatomy, and hence in building better FAM(B, G).

TABLE 3

Size correlation among objects of the Thorax.

|      | TSkn | RS   | TSk  | IMS  | RPS  | TB   | LPS  | PC   | E    | AS   | VS |
|------|------|------|------|------|------|------|------|------|------|------|----|
| TSkn | 1    |      |      |      |      |      |      |      |      |      |    |
| RS   | 0.76 | 1    |      |      |      |      |      |      |      |      |    |
| TSk  | 0.76 | 0.93 | 1    |      |      |      |      |      |      |      |    |
| IMS  | 0.48 | 0.76 | 0.71 | 1    |      |      |      |      |      |      |    |
| RPS  | 0.6  | 0.92 | 0.88 | 0.75 | 1    |      |      |      |      |      |    |
| TB   | 0.06 | 0.41 | 0.5  | 0.56 | 0.59 | 1    |      |      |      |      |    |
| LPS  | 0.64 | 0.93 | 0.87 | 0.74 | 0.96 | 0.57 | 1    |      |      |      |    |
| PC   | 0.47 | 0.51 | 0.45 | 0.65 | 0.28 | 0.11 | 0.3  | 1    |      |      |    |
| E    | 0.42 | 0.65 | 0.56 | 0.58 | 0.72 | 0.58 | 0.78 | 0.18 | 1    |      |    |
| AS   | 0.44 | 0.53 | 0.49 | 0.71 | 0.54 | 0.24 | 0.51 | 0.35 | 0.35 | 1    |    |
| VS   | 0.3  | 0.31 | 0.35 | 0.34 | 0.34 | 0.09 | 0.34 | -.01 | 0.05 | 0.42 | 1  |

TABLE 4

Size correlation among objects of the Abdomen.

|      | ASkn | ASk  | ASTs | Lvr  | SAT  | Msl  | Spl  | RKd  | LKd  | AIA  | IVC |
|------|------|------|------|------|------|------|------|------|------|------|-----|
| ASkn | 1    |      |      |      |      |      |      |      |      |      |     |
| Ask  | 0.68 | 1    |      |      |      |      |      |      |      |      |     |
| ASTs | 0.9  | 0.8  | 1    |      |      |      |      |      |      |      |     |
| Lvr  | 0.61 | 0.48 | 0.58 | 1    |      |      |      |      |      |      |     |
| SAT  | 1    | 0.69 | 0.92 | 0.61 | 1    |      |      |      |      |      |     |
| Msl  | 0.91 | 0.79 | 0.99 | 0.63 | 0.94 | 1    |      |      |      |      |     |
| Spl  | 0.62 | 0.43 | 0.61 | 0.51 | 0.65 | 0.62 | 1    |      |      |      |     |
| RKd  | 0.53 | 0.64 | 0.57 | 0.61 | 0.51 | 0.6  | 0.34 | 1    |      |      |     |
| LKd  | 0.53 | 0.56 | 0.52 | 0.51 | 0.49 | 0.54 | 0.34 | 0.87 | 1    |      |     |
| AIA  | 0.6  | 0.85 | 0.7  | 0.27 | 0.58 | 0.68 | 0.49 | 0.51 | 0.5  | 1    |     |
| IVC  | 0.32 | 0.58 | 0.47 | 0.29 | 0.32 | 0.46 | 0.3  | 0.38 | 0.36 | 0.67 | 1   |

Object Recognition

Figure 6:
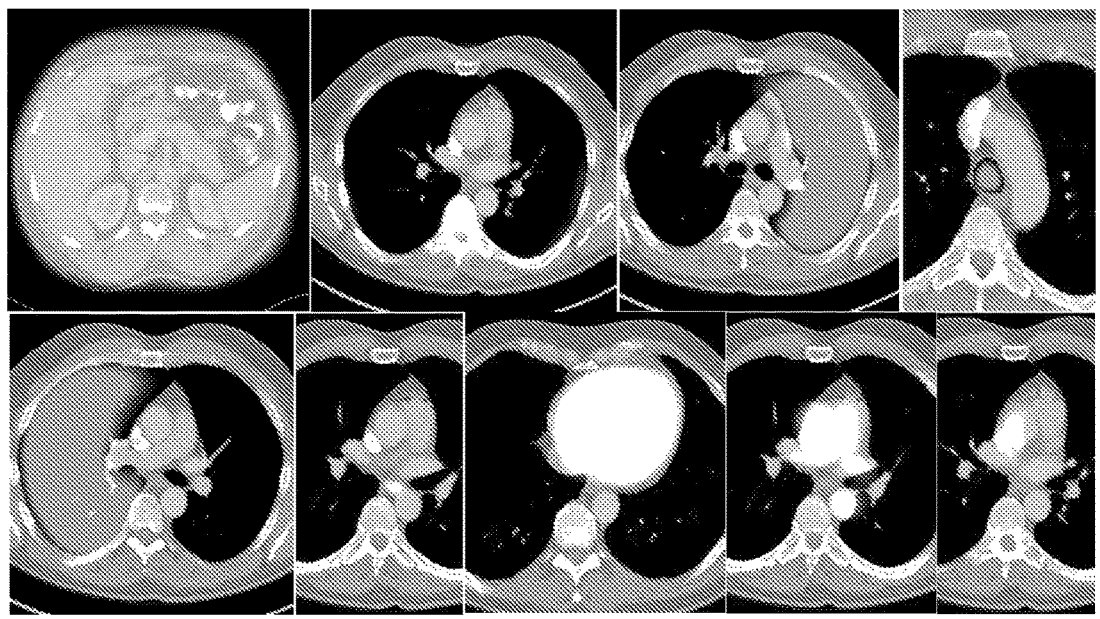
FIG. 6 illustrates sample recognition results for the Thorax for the alignment strategy shown in Equation (10). Cross sections of the model are shown overlaid on test image slices. Left to right: TSkn, TSk, LPS, TB, RPS, E, PC, AS, VS.
Figure 7:
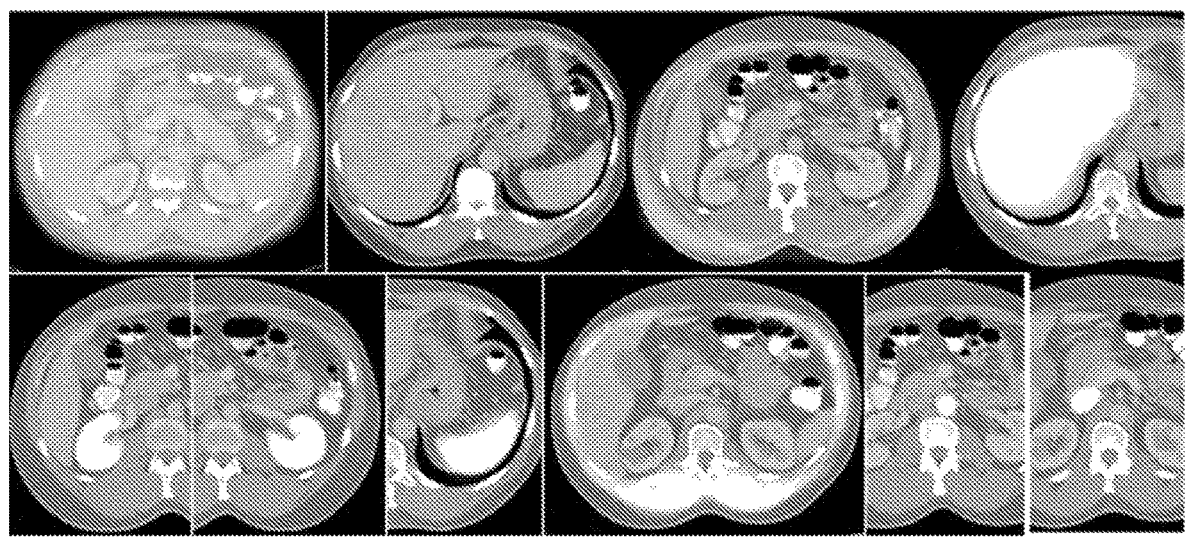
FIG. 7 illustrates sample recognition results for the Abdomen for the alignment strategy shown in Equation (10). Cross sections of the model are shown overlaid on test image slices. Left to right: ASkn, ASk, SAT, Lvr, RKd, LKd, Spl, Msl, AIA, IVC.
Figure 8:
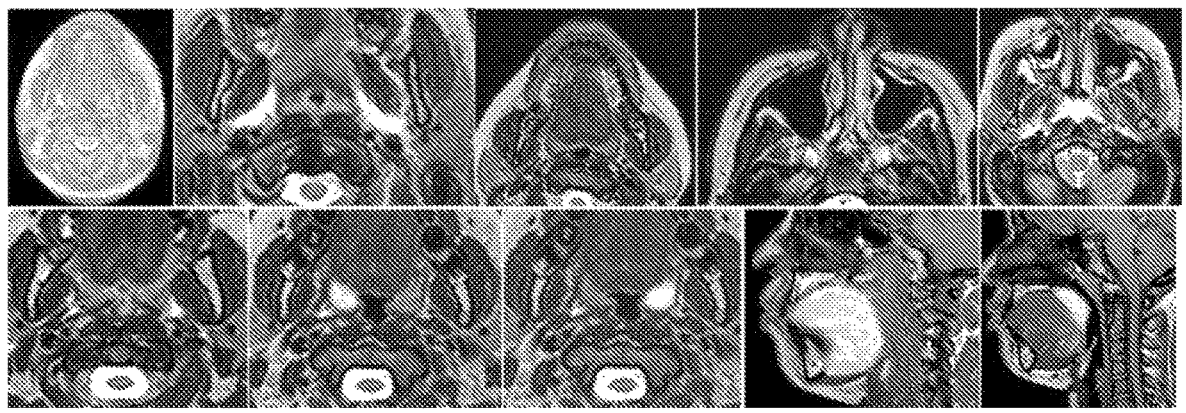
FIG. 8 illustrates sample recognition results for the Neck for the alignment strategy shown in Equation (10). Cross sections of the model are shown overlaid on test image slices. Left to right: NSkn, FP, Mnd, NP (note that NP is a combination of nasal cavity and nasopharynx), Ad, OP, RT, LT, Tng, SP.

Results for recognition are summarized in FIGS. 6-8 and Tables 6-9 for the different body regions. FIGS. 6-8 and Tables 6-8 illustrate recognition results for the three body regions for the best set up involving orientation adjustment selectively for different objects. The alignment strategy was as follows for the different objects in these results.

Non-sparse & hybrid objects: RS, LPS, RPS, TMS, TSk, Ask, Kd, Spl, Msl, LKd, RKd, A&B, FP, NSTs, Mnd, Tnsl, Tng, SP, Ad, RI, LT—no orientation alignment.

Sparse objects: TB, E, AS, VS, AIWA, IVC, Phrx, NP, OP—orientation alignment by all axes. Equation (10)

The recognition accuracy is expressed in terms of position and size. The position error is defined as the distance between the geometric centers of the known true objects regions with some membership value since it is fuzzy. This should not be construed as wrong segmentation. The main issue is if the model placement via recognition is accurate enough to yield good delineation. Similarly and due to the slice visualization mode, sparse object components may appear to be missed or to present with low membership values.

Although the inventors have not conducted extensive experiments to test all possible arrangements for orientation alignment for non-sparse and sparse objects, the inventors generally found that orientation adjustment for non-sparse objects does not improve recognition results. In some cases like PC, it may actually lead to deterioration of results. In the inventors' experience, the set up in Equation (10) turned out to be an excellent compromise from the viewpoint of

TABLE 5

Size correlation among objects of the Neck.

|      | NSkn | A&B  | FP   | Mnd  | NP   | OP   | Tng  | SP   | Ad   | LT  | RT |
|------|------|------|------|------|------|------|------|------|------|-----|----|
| NSkn | 1    |      |      |      |      |      |      |      |      |     |    |
| A&B  | 0.89 | 1    |      |      |      |      |      |      |      |     |    |
| FP   | 0.76 | 0.81 | 1    |      |      |      |      |      |      |     |    |
| Mnd  | 0.75 | 0.96 | 0.83 | 1    |      |      |      |      |      |     |    |
| NP   | 0.39 | 0.12 | −.06 | −.12 | 1    |      |      |      |      |     |    |
| OP   | 0.63 | 0.59 | 0.44 | 0.54 | 0.14 | 1    |      |      |      |     |    |
| Tng  | 0.83 | 0.75 | 0.76 | 0.66 | 0.19 | 0.65 | 1    |      |      |     |    |
| SP   | 0.5  | 0.27 | 0.23 | 0.14 | 0.46 | 0.26 | 0.37 | 1    |      |     |    |
| Ad   | −.2  | 0.61 | −.19 | 0.1  | −.29 | −.06 | −.07 | −.19 | 1    |     |    |
| LT   | 0.61 | 0.56 | 0.58 | 0.48 | 0.28 | 0.5  | 0.64 | 0.25 | −.1  | 1   |    |
| RT   | 0.61 | 0.56 | 0.58 | 0.48 | 0.28 | 0.5  | 0.64 | 0.25 | −.1  | 1   | 1  | in $\mathcal{I}^b$ and the center of the adjusted fuzzy model $FM^T(O_j)$. The size error is expressed as a ratio of the estimated size of the object at recognition and true size. Values 0 and 1 for the two measures, respectively, indicate perfect recognition. Note in FIGS. 6-8 that the model bleeds into adjacent tissue accuracy of results and efficiency. For comparison, recognition results for the thorax are demonstrated in Table 9 with no orientation adjustment for any object in both model building and recognition.

TABLE 6

Recognition results (mean, standard deviation) for Thorax for the strategy in (10). ("Mean" excludes VS.)

|             | TSkn | RS   | TSk  | IMS  | LPS  | TB   | RPS  | E    | PC   | AS   | VS   | Mean |
|-------------|------|------|------|------|------|------|------|------|------|------|------|------|
| Location    | 3.9  | 5.5  | 9.0  | 5.6  | 6.3  | 11.6 | 10.4 | 9.8  | 8.6  | 10.7 | 31.8 | 8.1  |
| Error (mm)  | 1.5  | 2.3  | 5.0  | 3.5  | 3.1  | 5.0  | 4.7  | 4.8  | 5.0  | 5.4  | 12.0 | 4.0  |
| Size        | 1.0  | 0.99 | 0.96 | 0.95 | 0.97 | 0.91 | 0.98 | 0.9  | 0.95 | 1.01 | 0.77 | 0.96 |
| error       | 0.01 | 0.02 | 0.05 | 0.05 | 0.03 | 0.06 | 0.04 | 0.14 | 0.05 | 0.08 | 0.06 | 0.06 |

TABLE 7

Recognition results (mean, standard deviation) for Abdomen for the strategy in (10).

|  | ASkn | SAT | ASk | Lvr | ASTs | Kd | Spl | Msl | AIA | IVC | RKd | LKd | Mean |
|---|---|---|---|---|---|---|---|---|---|---|---|---|---|
| Location | 5.9 | 20.2 | 11.7 | 7.9 | 7.2 | 10.6 | 11.6 | 7.7 | 8.2 | 8.7 | 11.3 | 7.3 | 9.8 |
| Error (mm) | 3.4 | 8.5 | 7.9 | 5.4 | 3.0 | 9.8 | 13.9 | 3.6 | 2.8 | 7.2 | 11.6 | 7.4 | 7 |
| Size | 1.0 | 0.97 | 0.96 | 0.93 | 1.0 | 0.94 | 1.2 | 1.01 | 1.1 | 1.15 | 0.97 | 0.93 | 1.01 |
| error | 0.02 | 0.03 | 0.06 | 0.07 | 0.02 | 0.09 | 0.19 | 0.03 | 0.13 | 0.1 | 0.1 | 0.08 | 0.07 |

TABLE 8

Recognition results (mean, standard deviation) for Neck for the strategy in (10).

|  | NSkn | A&B | FP | NSTs | Mnd | Phrx | Tnsl | Tng | SP | Ad | NP | OP | RT | LT | Mean |
|---|---|---|---|---|---|---|---|---|---|---|---|---|---|---|---|
| Location | 3 | 7.8 | 4.2 | 4.8 | 12.5 | 10.4 | 2.8 | 4.9 | 5.1 | 1.8 | 11.1 | 10 | 2.9 | 2.3 | 5.96 |
| Error (mm) | 1.2 | 3.8 | 2.1 | 2.1 | 3.7 | 4.5 | 1.8 | 2.8 | 1.8 | 0.8 | 6.8 | 8.7 | 2.2 | 2.1 | 1.96 |
| Size | 1 | 0.9 | 1 | 0.92 | 0.74 | 0.8 | 1 | 1.02 | 0.93 | 0.9 | 0.65 | 0.74 | 0.92 | 0.9 | 0.93 |
| error | 0.01 | 0.03 | 0.03 | 0.06 | 0.05 | 0.04 | 0.1 | 0.06 | 0.24 | 0.12 | 0.07 | 0.2 | 0.11 | 0.12 | 0.04 |

TABLE 9

Recognition results for Thorax with no orientation alignment. ("Mean" excludes VS.)

|  | TSkn | RS | TSk | IMS | LPS | TB | RPS | E | PC | AS | VS | Mean |
|---|---|---|---|---|---|---|---|---|---|---|---|---|
| Location | 3.9 | 5.5 | 9 | 5.6 | 6.3 | 8 | 10.4 | 14.2 | 8.6 | 8.1 | 33.6 | 8.0 |
| Error (mm) | 1.5 | 2.3 | 5 | 3.5 | 3.1 | 6.5 | 4.7 | 10.5 | 5 | 7.5 | 15.1 | 4.9 |
| Size | 1.01 | 0.99 | 0.96 | 0.95 | 0.97 | 0.83 | 0.98 | 0.85 | 0.95 | 0.99 | 0.77 | 0.95 |
| error | 0.01 | 0.02 | 0.05 | 0.05 | 0.03 | 0.08 | 0.04 | 0.12 | 0.05 | 0.08 | 0.06 | 0.05 |

Size error is always close to 1 for all body regions and objects. Generally, recognition results for non-sparse objects are excellent with a positional error of mostly 1-2 voxels. Note that for DS1 and DS2, voxels are quite large. In particular, since recognition results do not improve much with finer discretization of the model but only increase computation for recognition, the inventors constructed models with isotropic voxels of side equal to one half of the largest dimension of the voxels in the original data. Thus, for DS1 and DS2, the model voxels are of size 2.5×2.5×2.5 mm³. The inventors observed that the positional accuracy within the slice plane is better than across slices. In other words, errors listed in the tables are mostly in the third dimension in which voxel size is large. Orientation adjustment improves recognition somewhat for some sparse objects, but has negligible effect for non-sparse objects, at least in the thorax.

Figure 9:
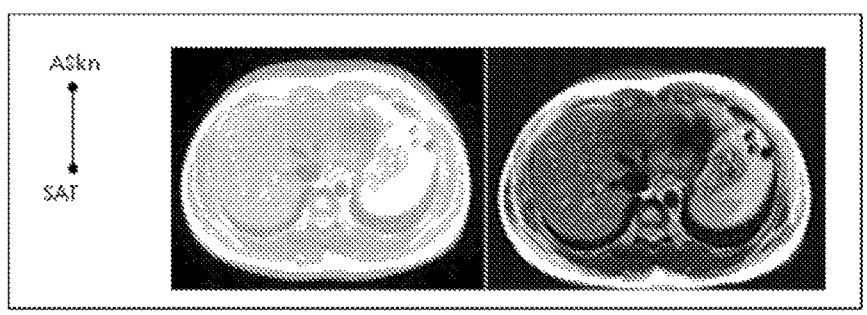
FIG. 9 illustrates the recognition results for the MRI data set DS4 (right) with the model cross-section overlaid on test image slices for ASkn and SAT.
Figure 10:
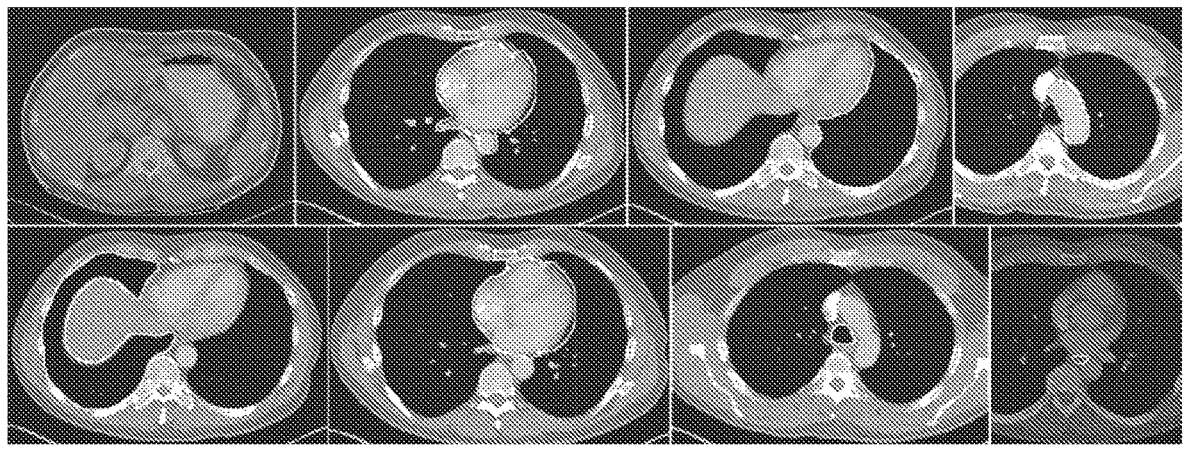
FIG. 10 illustrates sample delineation results for the Thorax. Left to Right: TSkn, TMS, LPS, AS, RPS, PC, TB, E.
Figure 11:
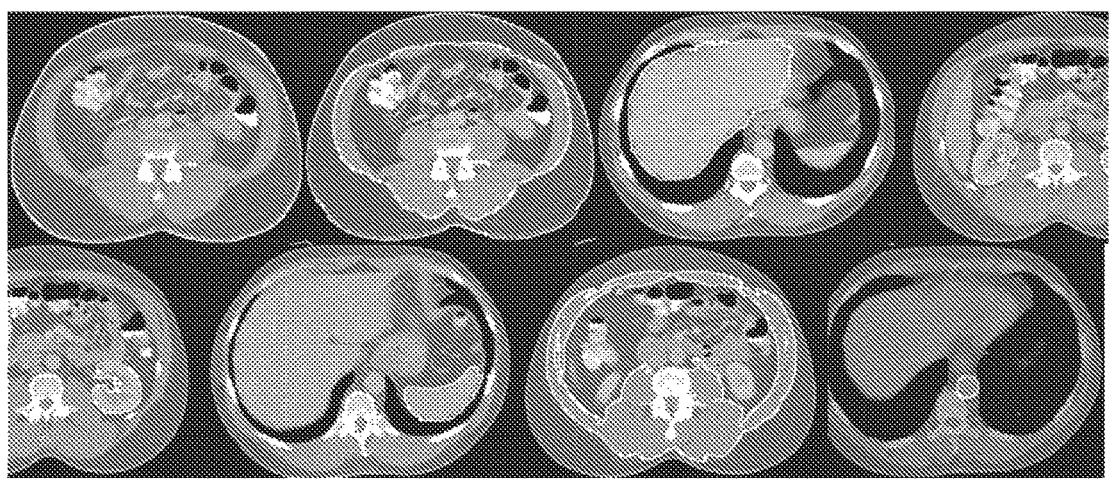
FIG. 11 illustrates sample delineation results for the Abdomen. Left to Right: ASkn, SAT, Lvr, SAT, RKd, LKd, Spl, Msl, AIA.
Figure 12:
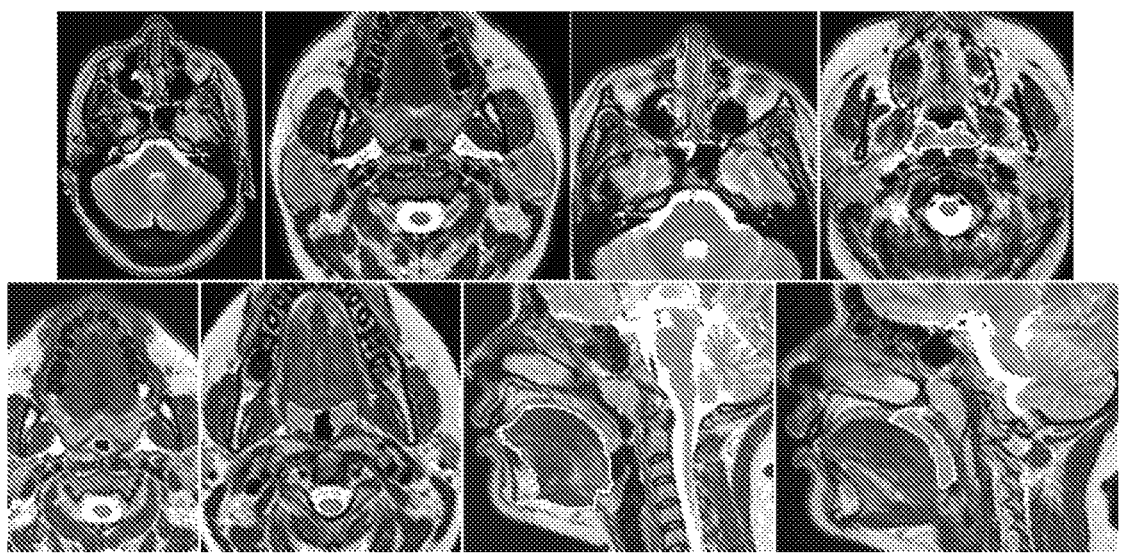
FIG. 12 illustrates sample delineation results for the Neck. Left to Right: NSkn, FP, NP, OP, RT, LT, Tng, SP, Ad.
Figure 13:
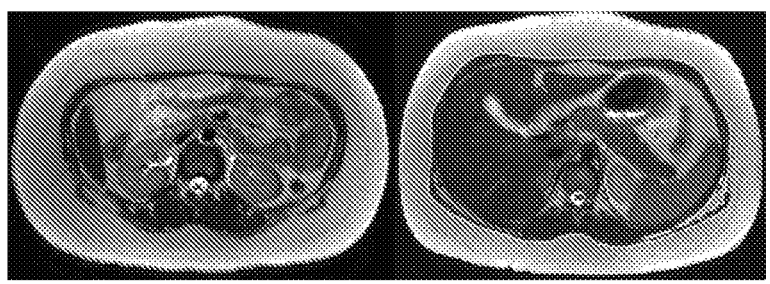
FIG. 13 illustrates sample delineation results for DS4 for ASkn (left) and SAT (right).

The recognition results for the MRI data set DS4 are demonstrated in FIG. 9 and Table 10. Again, since the model is fuzzy, it will encroach into adjacent tissue regions with some membership value. Since the goal here was just to measure subcutaneous adiposity, the hierarchy was simplified as shown in FIG. 9. Again the position error is 1-2 voxels. These results are particularly noteworthy since they are generated by using the models built from image data sets acquired from a different modality, namely CT, and for a different group with an age difference of about 40 years and with a different gender. This underscores the importance of understanding the dichotomy between recognition and delineation. Recognition is a high-level and rough process which gives anatomic context. The models do not have to be detailed attempting to capture fine details. Obtaining the anatomic context is a necessary step for achieving accurate delineation. It is important to note here that for the cross modality operation to work in this manner, the MR image intensities should be standardized (Nyul and Udupa 1999).

TABLE 10

Recognition accuracy for the objects shown in FIG. 9.

|  | ASkn | SAT |
|---|---|---|
| Position | 4.6 | 12.97 |
| Error (mm) | 2.5 | 5.3 |
| Size Error | 1.01 | 1 |
|  | 0.05 | 0.03 |

Object Delineation

Sample delineation results are displayed in FIGS. 10-13 for DS1-DS4. Delineation accuracy statistics for these data sets, expressed as false positive and false negative volume fractions (FPVF, FNVF) as well as mean Hausdorff distance (HD) between the true and delineated boundary surfaces, are listed in Tables 11-14. The HD measure is defined as the mean over all test subjects of the median of the distances of the points on the delineated object boundary surface from the true object boundary surface.

Delineation results for VS (Thorax) are not presented since the recognition accuracy for VS is not adequate for reliable delineation. It is noted that the delineation of 21 non-sparse objects achieves a mean FPVF and FNVF of 0.02 and 0.08, respectively, and a mean HD of 0.9 voxels, which are generally considered to be excellent. Six sparse objects also achieve good delineation outcome, with the above mean measures reading 0.05, 0.15, and 1.5, respectively. However, sparse objects VS, E, IVC, Mnd, and NP pose challenges for effective delineation. Often, even when their recognition is effective, it is difficult to guarantee placement of seed sets $A_O$ and $A_B$ appropriately within and outside these objects because of their sparse nature. In DS3 (MR images of neck), it is very difficult to properly delineate Mnd, NP, and OP because of their poor definition in the image. To test the effectiveness of the models created from these data (DS3) in segmenting the same objects on CT data of a group of three different pediatric subjects, the inventors devised a simple hierarchy with NSkn as the root and with Mnd, NP, and OP as its offspring objects. The delineation results obtained for these four objects were excellent, with a mean FPVF of 0, 0.01, 0, and 0.02, and mean FNVF of 0.01, 0.01, 0.02 and 0.1, respectively.

TABLE 11

Delineation results for Thorax (mean & standard deviation).

|  | TSkn | RS | TSk | IMS | LPS | RPS | E | PC | TB | AS |
|---|---|---|---|---|---|---|---|---|---|---|
| FPVF | 0.02 | 0.0 | 0.19 | 0.03 | 0.01 | 0.01 | 0.0 | 0.01 | 0.01 | 0.01 |
|  | 0.02 | 0.0 | 0.05 | 0.01 | 0.03 | 0.02 | 0.0 | 0.00 | 0.00 | 0.00 |
| FNVF | 0.05 | 0.06 | 0.13 | 0.07 | 0.04 | 0.04 | 0.49 | 0.09 | 0.16 | 0.17 |
|  | 0.06 | 0.04 | 0.07 | 0.07 | 0.02 | 0.02 | 0.19 | 0.06 | 0.14 | 0.17 |
| HD | 3.6 | 1.24 | 10.6 | 6.2 | 2.9 | 2.1 | 3.1 | 3.5 | 5.2 | 5.3 |
| (mm) | 4.5 | 0.42 | 2.4 | 1.8 | 8.8 | 4.7 | 0.87 | 1.3 | 1.8 | 2.5 |

TABLE 12

Delineation results for Abdomen (mean & standard deviation).

|  | ASkn | ASk | Lvr | ASTs | SAT | RKd | LKd | Spl | Msl | AIA |
|---|---|---|---|---|---|---|---|---|---|---|
| FPVF | 0.01 | 0.06 | 0.04 | 0.12 | 0.05 | 0.00 | 0.01 | 0.0 | 0.13 | 0.01 |
|  | 0.00 | 0.01 | 0.02 | 0.05 | 0.03 | 0.00 | 0.01 | 0.0 | 0.03 | 0.0 |
| FNVF | 0.05 | 0.14 | 0.1 | 0.15 | 0.12 | 0.13 | 0.1 | 0.13 | 0.09 | 0.13 |
|  | 0.08 | 0.09 | 0.05 | 0.09 | 0.02 | 0.04 | 0.02 | 0.03 | 0.08 | 0.03 |
| HD | 1.7 | 6.9 | 5.3 | 1.74 | 1.6 | 2.4 | 5.4 | 6.8 | 2.5 | 5.6 |
| (mm) | 2.7 | 1.5 | 1.6 | 1.0 | 0.8 | 1.1 | 4.8 | 6.0 | 1.1 | 1.8 |

TABLE 13

Delineation results for Neck (mean & standard deviation).

|  | NSkn | FP | Mnd | NP | OP | RT | LT | Tng | SP | Ad |
|---|---|---|---|---|---|---|---|---|---|---|
| FPVF | 0.0 | 0.0 | 0.01 | 0.01 | 0.0 | 0.01 | 0.01 | 0.02 | 0.01 | 0.0 |
|  | 0.0 | 0.0 | 0.0 | 0.0 | 0.0 | 0.0 | 0.0 | 0.01 | 0.01 | 0.0 |
| FNVF | 0.0 | 0.1 | 0.49 | 0.32 | 0.2 | 0.06 | 0.06 | 0.02 | 0.08 | 0.07 |
|  | 0.01 | 0.05 | 0.08 | 0.2 | 0.02 | 0.02 | 0.01 | 0.01 | 0.01 | 0.04 |
| HD | 2.8 | 0.83 | 3.3 | 3.8 | 7.6 | 3.3 | 3.2 | 8.4 | 8.03 | 2.2 |
| (mm) | 0.06 | 0.53 | 0.56 | 1.01 | 2.4 | 0.62 | 1.4 | 1.92 | 4.0 | 0.3 |

TABLE 14

Delineation results for DS4.

|  | ASkn | SAT |
|---|---|---|
| FPVF | 0.0 | 0.06 |
| FNVF | 0.03 | 0.01 |
| HD (mm) | 1.7 | 3.9 |

Comparison with a Non-Hierarchical Approach

To study the effect of the hierarchy and the knowledge encoded in it on recognition, Table 15 lists the recognition performance of a non-hierarchical approach. The results are shown for Thorax wherein each object is recognized on its own by using the same fuzzy models $FM(O_j)$ as used in the hierarchical AAR system. The initial pose for search is taken to be the center of the image and search range covers roughly the whole body region with the scale factor range the same as that for the hierarchical approach. In comparison to the hierarchical approach (Tables 6 and 9), it is clear that non-hierarchical recognition performance is much worse.

TABLE 15

Recognition results for Thorax: non-hierarchical approach (mean & standard deviation).

|  | TSkn | RS | TSk | IMS | LPS | TB | RPS | E | PC | AS | VS | Mean |
|---|---|---|---|---|---|---|---|---|---|---|---|---|
| Location | 10.5 | 12.9 | 21.1 | 27.7 | 91.4 | 53.3 | 72.3 | 42.4 | 45.5 | 23.1 | 82.2 | 43.8 |
| error (mm) | 9.5 | 13.1 | 21.8 | 9.8 | 10.8 | 20.9 | 12.9 | 34.5 | 12.5 | 15.2 | 33.8 | 17.7 |
| Size | 1.0 | 1.01 | 0.96 | 0.92 | 0.8 | 0.82 | 0.8 | 0.86 | 0.9 | 0.97 | 0.81 | 0.9 |
| error | 0.02 | 0.09 | 0.08 | 0.07 | 0.09 | 0.06 | 0.07 | 0.14 | 0.06 | 0.11 | 0.08 | 0.08 |

Computational Considerations

Program execution times are estimated on a Dell computer with the following specifications: 4-core Intel Xeon 3.6 GHz CPU with 8 GB RAM and running the Linux-jb18 3.7.10-1.16 operating system. Mean computational times for the AAR steps are listed in Table 16. Model building includes the construction of fuzzy models and the estimation of $\rho$, $\lambda$, and all parameters related to recognition and delineation, including the optimal threshold parameters $Th_j$. This latter step takes about 12 seconds per object. As seen from Table 16, each of the three main operations takes under 1 minute per object. Among these operations, only the time for model building depends on the number of training data sets, while recognition and delineation are independent of this factor. On average, model building times per object per training data set for Thorax, Abdomen, and Neck are, respectively, 1.4 sec, 1.7 sec, and 1 sec. In statistical atlas based methods, the computational time for image registration becomes the bottleneck. The calculation taking Elastix as a representative registration tool kit (Klein, S., Staring, M., Murphy, K., Viergever, M. A., Pluim, J. P. W., 2010. Elastix: a toolbox for intensity based medical image registration, IEEE Transactions on Medical Imaging, 29, 196-205) indicates that the creation of a single atlas for each of the 11 objects of the Thorax at a reduced image resolution of 2.5×2.5×2.5 mm³ for the 25 training data sets of DS1 would take about 23.5 hours compared to 6.4 min for the AAR system. The time per object for recognition and delineation can also take several minutes for these methods. Even with 100 data sets for training and 15 objects in a body region, the total time needed for the AAR model building step would be about 40 minutes, whereas atlas building may take days to complete especially when multi-atlas strategies are used.

TABLE 16

Mean computational time in seconds per object for different operations and body regions.

| Operation | Thorax | Abdomen | Neck |
|---|---|---|---|
| Model building | 35 | 42 | 24 |
| Object recognition | 30 | 46 | 6 |
| Object delineation | 47 | 56 | 24 |

Comparison with Other Methods

The publications reporting works that are directly related to the invention in spirit are (Baiker et al. 2010, Chu et al. 2013, Criminisi et al. 2013, Lu et al. 2012, Linguraru et al. 2012, Okada et al. 2008, Zhou et al. 2012). In Table 17, a comparison to the AAR system of the invention is provided based on the results reported in these works. It is noted that a quantitative grading/understanding of the methods is impossible since the data sets used, acquisition protocols and resolutions, considered objects, training and test data set subdivisions, cross validation strategies, and computing platforms are all different in these methods. Interestingly, a commonality among them is that they all focused on CT image data sets.

TABLE 17

A comparison with the current methods from the literature that are related to the inventive methods. Unknown and irrelevant entries are indicated by "~".

| Method | Objects | Voxel size (mm³) | Training-to-test data proportion | Location error (mm) | Region overlap (Dice, Jackard Index (JI), etc.) |
|---|---|---|---|---|---|
| Lu et al. 2012 | Prostate, bladder, rectum | ~ × ~ × 0.8 to 5 | 141 to 47, 4-fold | 2.4 to 4.2 | ~ |
| Linguraru et al. 2012 | Liver, spleen, kidneys | $(0.5$ to $0.9)^2 \times 1$ to 5 | 27 to 1, 28-fold | 0.8 to 1.2 | 90.9% to 94.8% |
| Okada et al. 2008 | Liver, vena cava, gallbladder | 0.7 × 0.7 × 2.5 | 20 to 8 | (for liver) 1.5 to 2.8 | 88% |
| Chu et al. 2013 | Liver, spleen, pancreas, kidneys | $(0.55$ to $0.82)^2 \times$ 0.7 to 1 (estimated) | 90 to 10, 10-fold | ~ | 56% (pancreas-JI) to 95.2% (liver-Dice) |
| Criminisi et al. 2013 | 26 anatomic structures in the torso | $(0.5$ to $1)^2 \times 1$ to 5 | 318 to 82 | 9.7 to 19.1 (mean for each structure) | ~ |
| Zhou et al. 2012 | 12 organ regions in thorax, abdomen, pelvis | $(0.6$ to $0.7)^3$ | 300 to 1000 | 6 to 14 for mode locations | ~ |
| Baiker et al. 2010 | Brain, heart, kidneys, lungs, liver, skeleton | $(0.332)^3$ | MOBY atlas, 26 datasets | ~ | 47% to 73% |

Among these methods, (Chu et al. 2013, Linguraru et al. 2012, Lu et al. 2012, Okada et al. 2008) comprise one group wherein the body region of focus was the pelvis or abdomen, with 3-5 objects considered for segmentation. They all employ an object localization step, which is achieved either through an atlas (Chu et al. 2013, Linguraru et al. 2012, Okada et al. 2008), statistical shape models (Okada et al. 2008), or machine learning techniques (Lu et al. 2012), and subsequently a delineation step that uses graph cuts (Chu et al. 2013, Linguraru et al. 2012), information theory (Lu et al. 2012), and MAP or ML estimation (Chu et al. 2013, Okada et al. 2008). In the second group (Criminisi et al. 2013, Zhou et al. 2012), the aim is only to locate the objects via machine learning techniques. The third group is constituted by (Baiker et al. 2010), the only work that considered body-wide organs, but in mice, using a kinematic model of the skeletal joints to localize objects relative to different skeletal components.

It is observed that, for the same objects (liver, kidneys, and spleen), the results expressed herein are comparable to, often better than, the current results from literature, especially considering the 5 mm slice spacing and the equal training-to-test data set proportion for the evaluation. Those skilled in the art will appreciate that the development of a general AAR system that can be readily applied and adapted to different body regions, multitudes of organs, and modalities has not yet been demonstrated in the literature.

Observations

The methods presented herein provide a general body of techniques for automatic anatomy recognition and delineation whose principles are not tied to any specific body region, organ system, or imaging modality. The inventors took a fuzzy approach for building the models and attempted to harness as much specific anatomic information as possible to be embedded into the fuzzy anatomic model. The inventors demonstrated the generality of the approach by examining the performance of the same AAR system on three different body regions using CT and MR image data sets. The inventors also illustrated the potential of the system for rapid prototyping by demonstrating its adaptability to a new application on a different modality (DS4). The system is set up to operate fully automatically. All image modality-specific parameters needed—threshold intervals for objects in B for recognition and affinity parameters for delineation—are estimated automatically from the training data sets. When a new application is sought at a modality different from those considered in the anatomy model FAM(B, G), a few sample segmentations of the objects of interest and the matching images are needed for relearning these image intensity-related parameter values (specifically, $Th_l$ and the affinity parameters). All other modality-independent aspects of the model do not need retraining. In the case of MRI, images from each separate MRI protocol have to be standardized for image intensity so that setting up these parametric values becomes sensible. Separation of modality-independent from dependent aspects, organization of objects in a hierarchy, encoding object relationship information into the hierarchy, optimal threshold-based recognition learning, and fuzzy model-based IRFC are novel and powerful concepts with consequences in recognition and delineation, as demonstrated herein.

While the above strengths of the AAR system of the invention are quite unique, the system has some limitations at present. First, the inventors have not studied the performance of the system on patient images that contain significant pathology. However, it is noted that DS4 indeed includes image data sets of patients who are obese. Note also that these image data sets are from a very different age and gender group and on a different imaging modality from those used to build FAM(B, G). The inventors believe that it is important to make the system operate satisfactorily on normal or near-normal images before testing it on images with diverse pathologies. Second, the accuracy is inadequate for some sparse objects for recognition (VS, IVC) and delineation (E, Mnd, NP). Also, the inventors have not considered herein other important and challenging sparse objects such as the adrenal glands, pancreas, and the spinal cord. If recognition is inadequate, delineation will become unacceptable because it becomes impossible to appropriately initialize the delineation process and to exploit the model for making up for missing boundary information in the image in delineation. When these cases were closely examined, it became clear that there are fundamental challenges in the model building stage itself for sparse objects. Generally, the inventors found that sparse objects have much greater variation than their non-sparse counterparts in form, topology, and geographic layout, compared to their size. As an example, consider AS and VS (Thorax). The descending aortic portion of AS is often straight and directed vertically downward while in some subjects it may be inclined, curved, or even tortuous, with other portions, especially the aortic arch, not varying much. The branching pattern of the left and right brachiocephalic veins and the course of the azygos vein in VS also vary considerably. In view of such difficulties, the inventors have come to the realization that sparse objects should not be modeled directly from their precise shape information in the binary image set $\mathcal{I}^b$, instead only their rough super form (such as a minimal super set that subsumes such variations) should be utilized in model building. The inventors are exploring the use of rough sets (Maji, P., Pal, S. K., 2012. Rough-Fuzzy Pattern Recognition: Applications in Bioinformatics and Medical Imaging, John Wiley & Sons, Inc. New York) for this purpose.

The AAR methodology seems to have definite computational advantages over atlas-based approaches. Further, in atlas-based methods, it is perhaps much more challenging to incorporate the extensive object-level knowledge that the AAR approach exploits at various stages for recognition and delineation. These incorporations constitute highly non-linear and discontinuous phenomena which are effected in intensity, geometric, and topological spaces. The kinematic model employed by Baiker et al. 2010 is a good analogy of how one may encode object relationships via a model that are difficult to emulate through continuous and smooth image/atlas deformations.

The problem of automatically determining the body region B following the definition of B within the given data set was not explored herein. As demonstrated in (Chen et al. 2012), it is possible to determine the slices delimiting a body region B automatically based on slice profiles. Furthermore, the information about the relationship between B and WB can also be encoded into the hierarchy as illustrated in FIG. 2(a) for each B.

The use of composite objects often leads to better recognition accuracy. This is because the multiple objects contained in a composite object offer tighter constraints in recognition search. The aspect of how objects can be grouped to achieve optimum recognition results needs further investigation. A related topic is how to device optimal hierarchies for a given body region. The hierarchies the inventors have considered so far are anatomically motivated. Perhaps there are "optimal" hierarchies from the view point of achieving the best recognition (and hence, delineation) results. In such an investigation, matters of how objects should be grouped as well as ordered in the hierarchy can both be addressed simultaneously using graph optimization techniques.

The inventors have set up the AAR-R and AAR-D procedures in a general way. Recognition and delineation algorithms other than those described herein can be used independently for R-ROOT and R-OBJECT and for D-ROOT and D-OBJECT within the same hierarchical set up. Similar to composite object recognition, delineation done simultaneously for multiple objects, unlike the one-object-at-a-time approach of AAR-D, may improve overall accuracy.

Computationally, there are three expensive operations in the AAR system—image interpolation, distance transform, and the delineation algorithm (FMIRFC). To make recognition and delineation operate in practical time in a clinical setting, implementations of these operations will desirably be sped up. Toward this goal, these operations may be implemented in a GPU. GPU implementations of some fuzzy connectedness algorithms have already been published (Zhuge, Y., Cao, Y., Udupa, J. K., Miller, R. W., 2011. Parallel fuzzy connected image segmentation on GPU. Medical Physics 38(7), 4365-4371; and Zhuge, Y., Ciesielski, K. C., Udupa, J. K., Miller, R. W., 2013. GPU-based relative fuzzy connectedness image segmentation. Medical Physics 40 (1), 011903-1-011903-10).

Finally, along the lines of the study underlying DS4, those skilled in the art will appreciate that AAR system may be adapted to several clinical applications. Some of the avenues the inventors are currently exploring for the proposed AAR approach are delineated in the examples provided in more detail below. For example, the AAR techniques described above may be modified for quantifying abdominal fat through the use of standardized anatomic space, providing automatic localization of IASLC-defined mediastinal lymph node stations, and providing radiation therapy planning in exemplary embodiments as described in detail below.

EXAMPLE 1: OPTIMIZATION OF ABDOMINAL FAT QUANTIFICATION ON CT IMAGING THROUGH USE OF STANDARDIZED ANATOMIC SPACE

Notations and Overall Approach

As noted above, it is desired to answer three questions related to fat quantification that have not been addressed in the literature. How does one ensure that the slices used for correlation calculation from different subjects are at the same anatomic location? At what single slice anatomic location do the areas of SAT and VAT estimated from a single slice correlate maximally with the corresponding volume measures? Are there combinations of multiple slices (not necessarily contiguous) whose area sum correlates better with volume than does single slice area with volume? The techniques of the invention adapted the AAR methodology described above to address these questions.

Let V(B, Q, G) denote the set of all possible 3D images of a precisely-defined body region B, taken as per a specified image acquisition protocol Q, from a well-defined group of subjects G. For example, B may be the abdominal region, which is defined by its superior bounding plane located at the superior most aspect of the liver and its inferior bounding plane located at the junction where the abdominal aorta bifurcates into common iliac arteries. Variable Q may be CT imaging with a specified set of acquisition parameters, and G may denote normal male subjects in the age range of 50 to 60 years. The reason for relating all analysis to a specified set V(B, Q, G) is that, it may not be possible to generalize the conclusions drawn about fat distribution when one changes some of the variables associated with V, especially patient group G. The inventors denote by V the set of images available for the study, which is assumed to be a representative subset of V(B, Q, G). Let P be an image in V of some subjects of his body region B. The inventors view $I^s$ as a set of $n_s$ axial slices $$I^s = \{S_1^s, \ldots, S_{n_s}^s\}.$$

Since $I^s$ is an image of B, $S_1^s$ and $S_{n_s}^s$ represent anatomic planes bounding B. It is assumed that they correspond to the superior and inferior bounding planes, $P_H^s$, and $P_D^s$ of B of subject s, respectively. All locations and coordinates are assumed to be specified with respect to a fixed Scanner Coordinate System (SCS) for all subjects. If the acquired images have extra slices, it is assumed that they have been removed to satisfy this condition. Note that if P and P are images in V(B, Q, G) of two subjects s and t, then the number of slices $n_s$ and $n_t$ representing B in the two subjects may not be equal. Similarly, the same numbered slices in $I^s$ and $I^t$ may not correspond to the same anatomic axial location in subjects s and t. Suppose one discretizes the anatomic axial positions in B from $P_H^s$ and $P_D^s$ into L anatomic locations $l_1^s, \ldots, l_L^s$ such that $l_1^s$ and $l_L^s$ always correspond to $P_H^s$ and $P_D^s$, respectively, for all subjects s. For example, position $l_i^s$ may correspond to the location of an axial plane passing through the middle of the body of the L1 lumbar vertebra of subjects; in this case, $l_i^t$ represents an axial plane at the same anatomic location for subject t. Locations $l_1^s, \ldots, l_i^t$ may be also thought of as representing anatomic landmarks labeled $l_1, \ldots, l_L$. In the above example, $l_i$ is the name of the landmark associated with location $l_i^s$. The inventors denote these anatomic landmarks by the ordered set AL=$\{l_1, \ldots, l_L\}$. In order to perform volume to area correlation analysis correctly, the inventors need to first assign a correct label from the set AL to every slice in every image $I^s$ in V. Since it is customary to use the vertebral column as reference for specifying homologous anatomic locations, the inventors will follow this same approach herein. It is noted however that the methods are general and can use any other reference system for locations. The inventors think of anatomic landmarks to be defined in a Standard Anatomic Space (SAS), and the process of assigning labels from AL to slices in any given image $I^s$ as a mapping from SCS to SAS.

Figure 14:
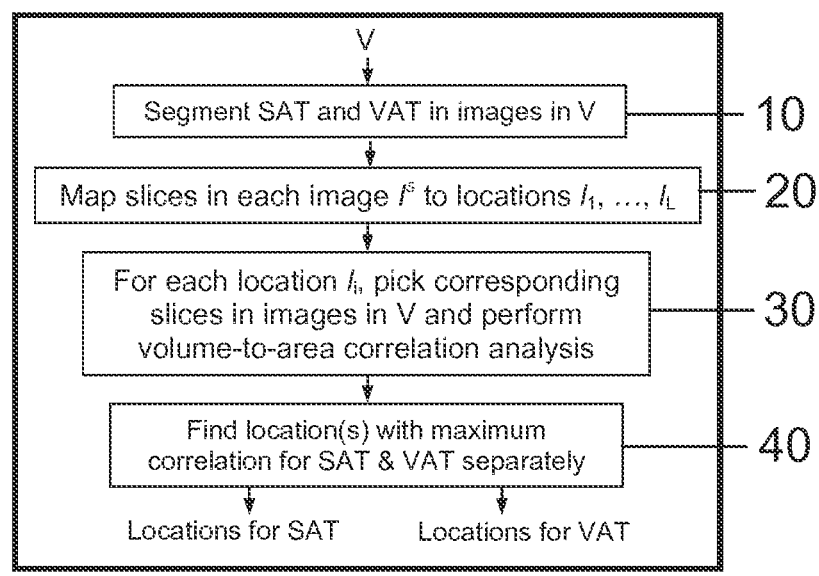
FIG. 14 illustrates a schematic representation of the approach of standardized anatomic space in an exemplary embodiment for quantifying abdominal fat.
Figure 15:
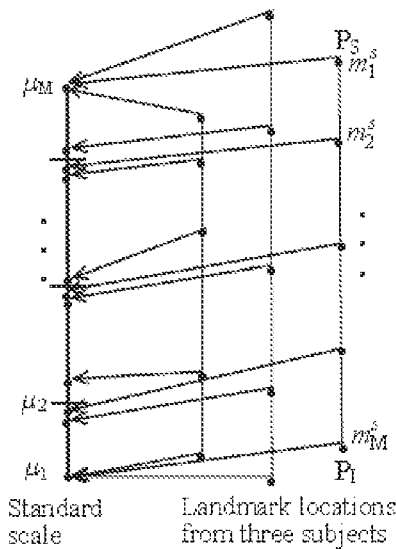
FIG. 15 illustrates calibration to create a standard scale. M standard locations selected on three patients are shown on the right. They are mapped linearly on to the standard scale shown (thick) on the left.

The overall approach to seek answers to the three questions posed above is depicted schematically in FIG. 14. The four steps involved are described below in detail.

Segmenting SAT and VAT Regions in Images in V

In this first step (FIG. 14, step 10), SAT and VAT regions in the images in V are automatically segmented by modifying the automatic anatomy recognition (AAR) system. As described above, the AAR system operates by creating a fuzzy anatomy model for a body region 13 and subsequently using this model to recognize and delineate organs in B. The fuzzy anatomy model consists of a hierarchical arrangement of the organs of B, a fuzzy model for each included organ, and organ relationships in the hierarchical order. The modification for purposes of this application includes considering just three objects—skin boundary, SAT, and VAT, with skin as the root object and SAT and VAT as its offspring objects, in place of all 10-15 major organs of B that are otherwise included in the model. The rest of the processes remain the same as the recognition and delineation methods described above. If V is a set of MR images, then image background non-uniformity correction and intensity standardization will have to be performed before applying AAR-based segmentation.

Assigning Landmark Labels $l_1, \ldots, l_L$ to Slices in Each Image $I^s$

Ideally, once the set AL of anatomic landmarks is selected, one could identify manually the anatomic location, and hence the landmark label, to be assigned to each slice $S_i^s$ of each image $I^s$ of V. Such a manual approach can be realized on CT imagery as follows. First segment the vertebral column in $I^s$, create 3D surface renditions of the column, and interactively indicate in this display the axial locations. The inventors use a visualization software package (e.g., CAVASS) for selecting locations quantitatively precisely on shaded surface renditions. In MR images, however, this approach will be more difficult since segmentation of the vertebral column is challenging. Since this manual approach is labor intensive, the inventors explored two alternative approaches—linear and non-linear, and compared them to the manual approach. In all approaches, the input is the set V of images and the result is a mapping that indicates the anatomic location (label) associated with each slice of each image of V (FIG. 14, step 20).

Linear Approach:

This approach assumes that, once it is guaranteed that the bounding planes $P_H^s$ and $P_D^s$ and hence slices $S_1^s$ and $S_{n_s}^s$ of image $I^s$, correspond to locations $l_1^s$ and $l_L^s$ respectively, then anatomic locations corresponding to slices $S_2^s$ and $S_{n_s-1}^s$ can be found by linearly mapping the $n_s$ slices from $S_1^s$ and $S_{n_s}^s$ to L slices $U_1^s$ and $PU_L^s$ via linear interpolation for any subjects. Note that L can be less than, or greater than, or equal to $n_s$. The only requirement on L is that it should be at least 2. Of course, it is possible that in this approach the mapped location of a slice $U_i^s$ may not match the true location of landmarks. To implement this approach, the inventors first identify the data set in V whose domain is the smallest in the longitudinal direction in terms of the number of slices, take this number to be L, and then linearly interpolate all other data sets to yield this number of slices. The inventors assume the slice locations of this data set to correspond approximately to landmarks $l_1, \ldots, l_L$. Mapping of anatomic locations to all other data sets is now established by the correspondence of the same numbered slices. In this manner, for any given slice number for any subject, the corresponding (linearly mapped) slice numbers for all other subjects are identified. A drawback of the linear approach is that non-linearities in the relationships among anatomic locations used as landmarks in the longitudinal direction cannot be accounted for.

Non-Linear Approach:

In the linear approach, two anatomic landmarks $l_1$ and $l_L$ were employed to anchor the first and the last slice of B and to predict the anatomic location of all other slices. Generally such a linear mapping does not yield locations that are sufficiently close to actual anatomic locations (as demonstrated below) of landmarks. This deficiency can be overcome by non-linear mapping. In this approach, in addition to $l_1$ and $l_L$, other key anatomic landmarks are used to refine mapping. The method consists of two stages—calibration and transformation.

Figure 16:
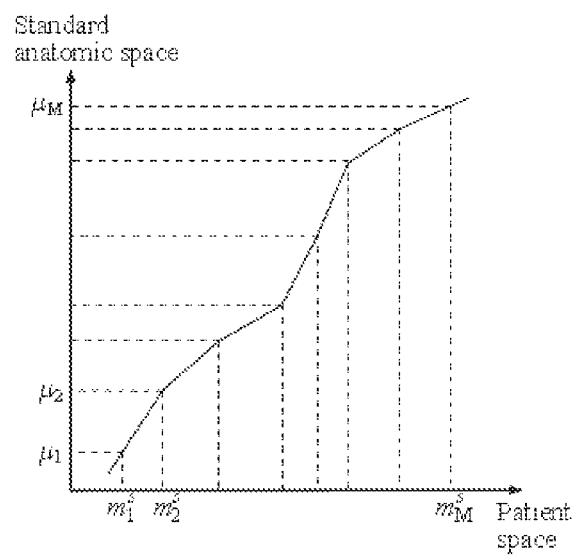
FIG. 16 illustrates non-linear mapping from patient space to standard anatomic space.

The purpose of the calibration stage is to learn any non-linearities that may exist in the relationships among anatomic locations. (Here "learning" does not have the same meaning as "training" widely used in machine learning.) Typically, the inventors select M<L key anatomic landmarks, denoted by $m_1, \ldots, m_M$, from among $l_1, \ldots, l_L$. In the present embodiment, the inventors selected the midpoints (in the vertical direction) of the vertebral bodies from T11 to L4 as key landmarks (so M=6). Next, these key landmarks are identified manually in a set $T \subset V(B, Q, G)$ of images. For any image $I^s$ in T, the locations of these key landmarks for subject s will be denoted by $m_1^s, \ldots, m_M^s$. A standard anatomic scale is then determined to be of length which is the largest of the lengths from $P_H^s$ and $P_D^s$ over all data sets in T. Locations $m_1^s, \ldots, m_M^s$ for every data set in T are then mapped linearly on to the standard scale (see FIG. 15) and the mean positions $\mu_1, \ldots, \mu_M$ of the key points on the standard scale over all mapped data sets of T are computed. The mapping from SCS to SAS is subsequently determined to be the piece-wise linear function that maps $m_1^s, \ldots, m_M^s$ to $\mu_1, \ldots, \mu_M$ as depicted in FIG. 16.

In the transformation stage (FIG. 16), given any image $I^s$, first the locations of its anatomic landmarks $m_1^s, \ldots, m_M^s$ are identified. Then the mapping function from SCS to SAS determined in the calibration stage is used to determine the label to be assigned to each slice $S_i^s$ of $I^s$. The algorithm, called SAS, for mapping to the standardized anatomic space, summarized herein, is straightforward and requires no special data structures or optimization in implementation.

| Algorithm | SAS |
|---|---|
| Input: | Two disjoint sets of images T and V, $T \subset (B, Q, G)$, $V \subset (B, Q, G)$; AL; $\{m_1, \ldots, m_M\}$. |
| Output: | A mapping from SCS to SAS; the set V of images with a label assigned to each slice of each image of V. |
| Begin | |
| Calibration Stage | |
| | C1. Determine standard scale and identify key landmarks $m_1, \ldots, m_M$ in each image in T; |
| | C2. Map key landmarks linearly to standard scale; |
| | C3. Estimate mean locations $\mu_1, \ldots, \mu_M$ of key landmarks on standard scale; |
| Transformation Stage | |
| | T1. For each image $I^s$ of V and for each of its slices, determine its key landmark locations $m_1^s, \ldots, m_M^s$; |
| | T2. Find the mapping of these locations as per SCS to SAS function; |
| | T3. Based on this mapped value assign label to each slice of $I^s$; |

Experimental Results and Discussion

Image Data

Variables G and Q defining V(B, Q, G) for the experiments were as follows. Contrast-enhanced abdominal CT image data sets from fifty 50-60 year-old male subjects with an image voxel size of $0.9 \times 0.9 \times 5$ mm$^3$ were utilized in the study. The subjects were radiologically normal with exception of minimal incidental focal abnormalities. The abdominal body region B was defined in the same way for the 50 subjects, with $P_H^s$ located at the superior most aspect of the liver and $P_D^s$ corresponding to the point of bifurcation of the abdominal aorta into common iliac arteries. Of the 50 data sets, 5 were used for calibration (constituting T) and the rest (constituting V) were used for testing.

Figure 17:
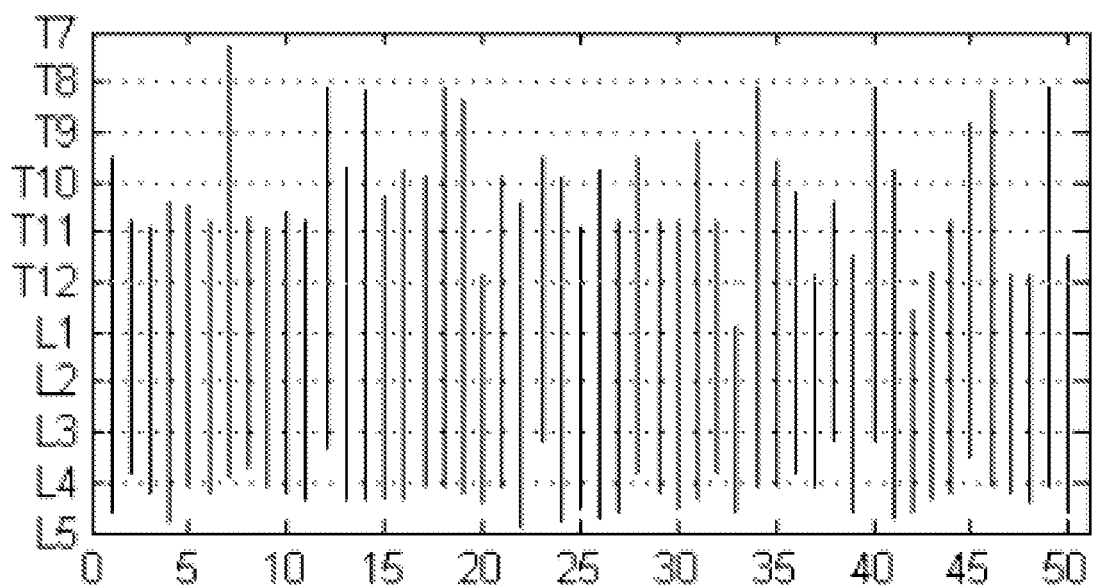
FIG. 17 illustrates anatomic locations of slices in B=the Abdominal Region for 50 subjects. The abscissa shows subject numbers, and the ordinate indicates the extent of B in different subjects in the cranio-caudal direction in terms of the vertebral bodies.

To illustrate the anatomic variability that exists among subjects, FIG. 17 plots schematically the locations of the mid points of vertebral bodies in the cranio-caudal (vertical) direction for all subjects considered in the study. The top and the bottom of the vertical line drawn for each subject indicate the extent of B in relation to the vertebral bodies. For example, in subject numbered 50 (the right-most location on the abscissa), the abdominal region starts from roughly the T11 vertebra and ends at the L5 vertebra. The locations of both the top-most and bottom-most slices have significant variability in terms of anatomic correspondence as seen in FIG. 17. To further illustrate qualitatively the variability in the layout of the vertebrae among subjects, FIG. 18 displays surface renditions of the skeletal components in B for some of the 50 subjects who show wide variation in FIG. 17.

Correlation Analysis

To study the nature of the volume-to-area correlation, the inventors analyzed the relationship between 3D volume and area estimated from a single slice as well as summed up areas estimated from 2 and 3 slices where the slices were selected at all possible locations and not necessarily contiguously situated (FIG. 14, step 30).

Correlation with Single Slice

Figure 18:
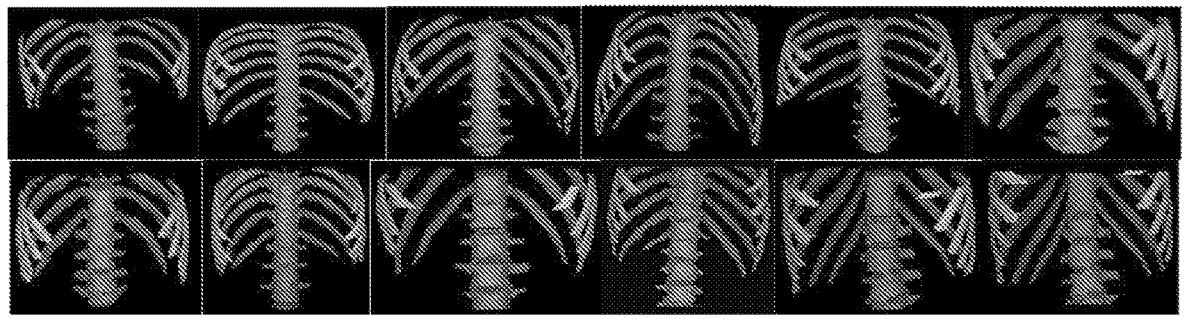
FIG. 18 illustrates surface renditions of the skeletal components in B of some of the subjects who showed wide variation in vertebral positions in FIG. 17 including subjects 4, 7, 11, 12, 14, 20, 22, 23, 33, 34, 37, and 48.

The inventors considered 34 subjects for correlation analysis by selecting those subjects whose body region B covered vertebrae from T10 to L4 as a common/overlap region among the 50 subjects. The reason for this decision is to guarantee that the body region of the subjects for calculating correlation will be in the same anatomic range in SAS. Some subjects for whom slices start from T12 or even higher positions as shown in FIG. 18 are not selected. For all 34 subjects, six spinal landmarks were selected from T10 to L3 as the mid points of the respective vertebral bodies. Although the method is illustrated by using 6 landmarks here, this number can be set to any value greater than or equal to 2 and any other landmarks can also be used.

Figure 19:
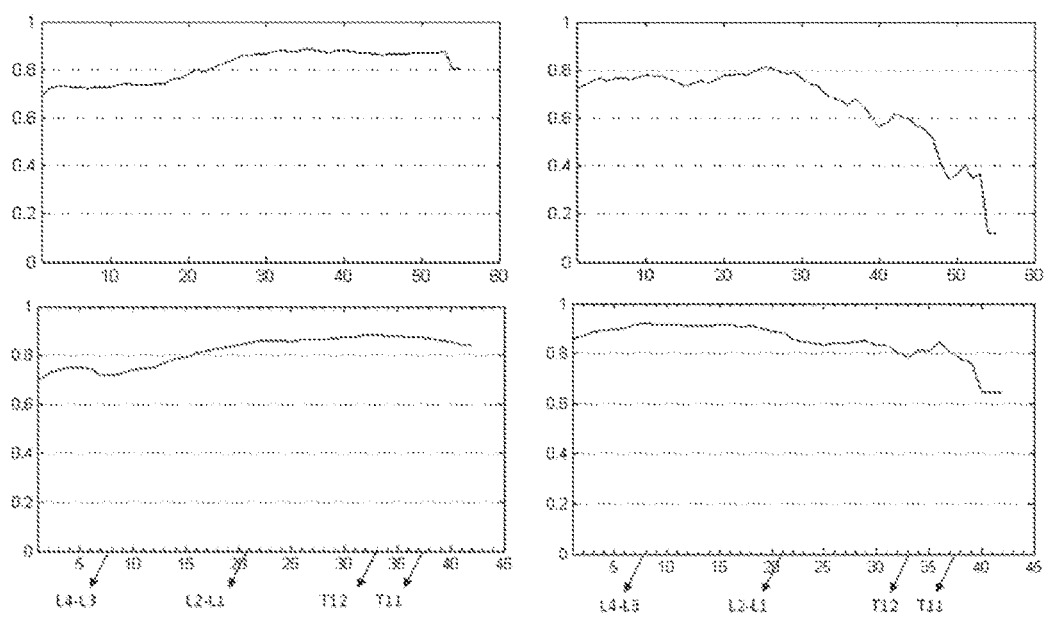
FIG. 19 illustrates correlation values from linear mapping (top row) and non-linear mapping (bottom row) for SAT (left) and VAT (right). The vertical axis shows the correlation value. The horizontal axis shows the location of image slices (Slice 1 is at the inferior most position). Some key landmark positions are indicated along the horizontal axis in the bottom row.

In order to study how correlation may vary for different anatomic slice locations, FIG. 19 (using data from 34 subjects) displays the correlation values as a curve for different slice locations for SAT and VAT by using both linear and non-linear mappings. Some key landmark positions are indicated along the horizontal axis in the bottom row of FIG. 19. The number of slices for linear and non-linear mapping is different and as such there is not much meaning in comparing the slices for the two methods by numbers. This is due to the fact that for linear mapping, the mapped slices are found by mapping the total number of slices to the same number of (smallest/largest) slices for every subject. For non-linear mapping on the other hand, because of the fact that the distance between successive landmarks is allowed to be different for different subjects, the total number of slices in SAS may not be the same as that of linear mapping. To examine how the location of maximum correlation may vary across subjects (FIG. 14, step 40), FIG. 20 displays the anatomic landmark locations at which maximum correlation occurred for SAT and VAT for the two methods for different subjects. FIG. 21 demonstrates the anatomic locations where maximum correlation is achieved by the two methods for two sample subjects, where slice images and their locations in the anatomic space for both SAT and VAT are shown with reference to the 3D rendered spine.

Figure 20:
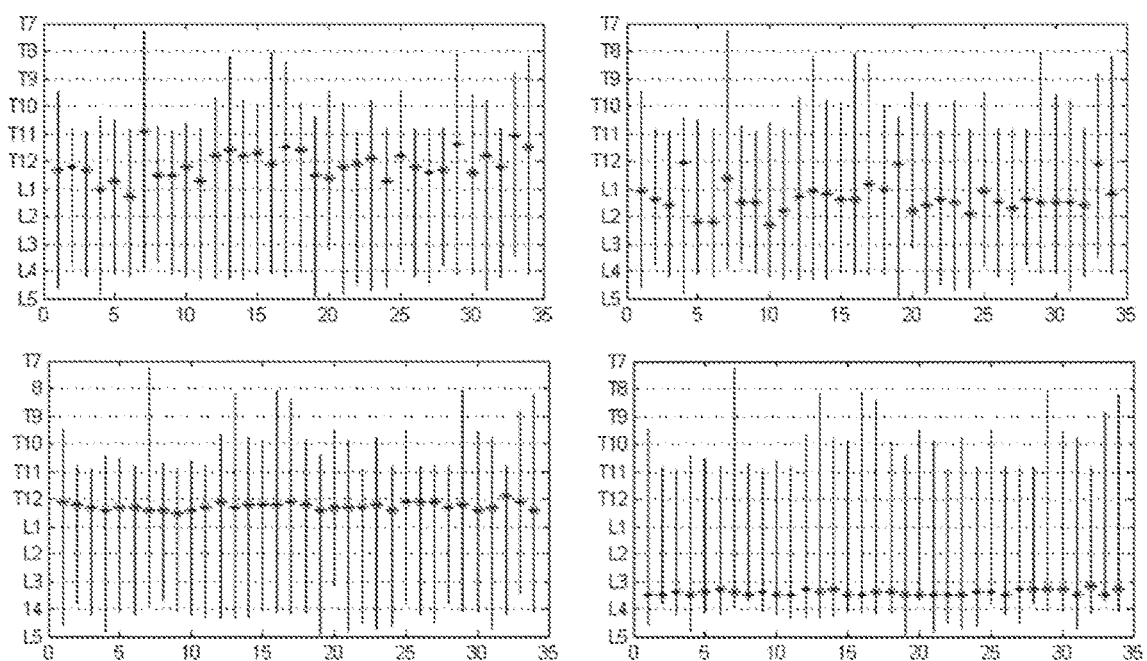
FIG. 20 illustrates anatomic locations (marked with '*') of maximum correlation between (single) slice area and volume (SAT on left, VAT on right, linear method in top row, non-linear method in bottom row). The horizontal axis shows subject numbers, and the vertical axis shows anatomic location from T7 to L5.
Figure 21:
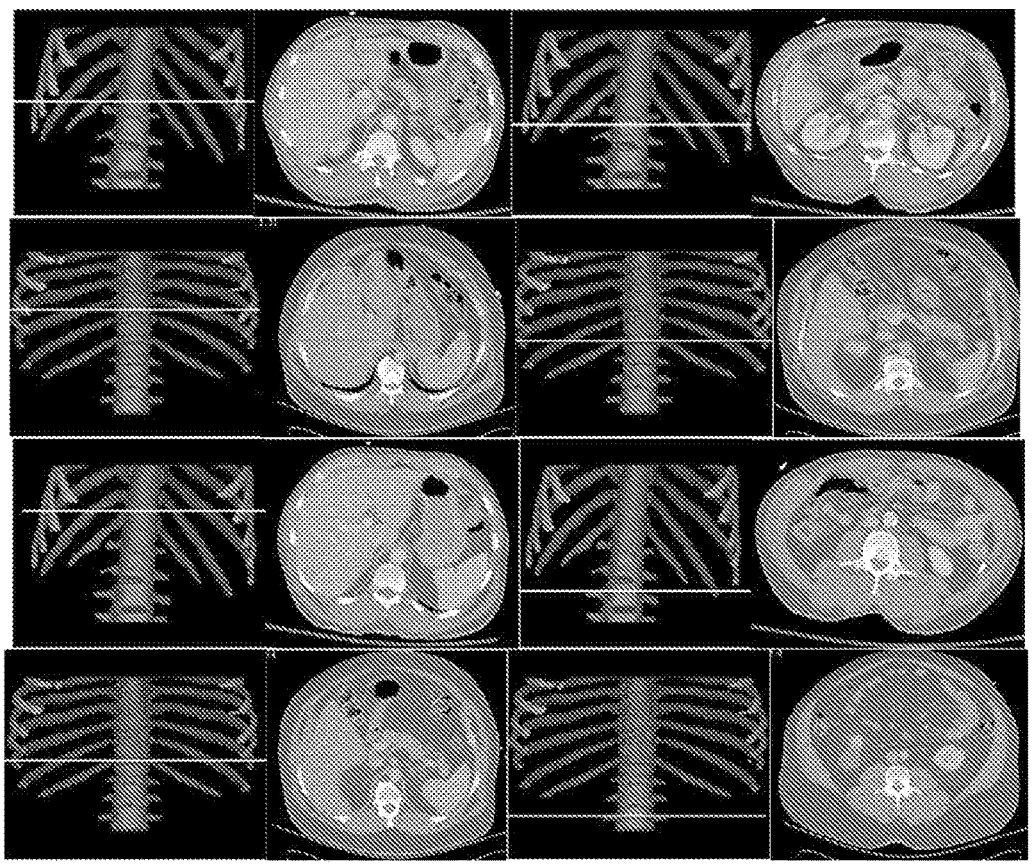
FIG. 21 illustrates anatomic locations where maximum correlation is achieved for the two mapping methods. The top two rows are for SAT (left) and VAT (right) by using linear mapping; and the bottom two rows represent SAT and VAT for non-linear mapping. The 1st and 3rd rows are from the same subject, and the 2nd and 4th rows are from another subject. The spine is used as a reference to show the slice locations (as a white line) of maximum correlation.

The following observations may be made from FIGS. 19-21. The maximum correlation for VAT derived from non-linear mapping achieved a 10% higher value than that of linear mapping. It is also clear that the maximum correlation occurs at different anatomic locations for SAT and VAT. With non-linear mapping, the maximum correlation occurs at T12 for SAT and L3 for VAT as shown in the bottom figures in FIG. 19. The maximum correlation also occurs at different anatomic locations for the different mapping methods. For SAT and VAT, the locations of maximum correlation derived from linear mapping vary considerably among subjects. The goal of correlation calculation is to find one or more anatomic locations which are optimal for estimating abdominal fat distribution. The slices from all subjects used for correlation calculation are expected to be at the same anatomic location. Correlation testing will have no meaning if every subject has the slice considered for correlation calculation at a different location. The site of maximum correlation derived from non-linear mapping has more precision than from simple linear mapping. In the bottom row of FIG. 20, there is a small variation of locations over all subjects which is less than 5.0 mm (same as slice spacing), implying that the slice localizations are anatomically very precise in the SAS (see Table 18). Table 19 shows the correlation derived from a single slice at different true anatomic locations where the maximum correlation for VAT occurs at L3-L4 and at T12-L1 for SAT. The results are similar to the correlation calculated from the non-linear method as shown in the bottom row of FIG. 20. Again, the anatomic location of maximum correlation for SAT is different from that of VAT.

TABLE 18

Correlation coefficients and slice location variation (in mm) for linear and non-linear mapping techniques. Correlations shown are maximum values.

|  | Single slice at L4-L5 | | Linear mapping | | Non-linear mapping | |
| --- | --- | --- | --- | --- | --- | --- |
|  | SAT | VAT | SAT | VAT | SAT | VAT |
| Correlation | 0.74 | 0.87 | 0.89 | 0.81 | 0.88 | 0.92 |
| Location variation (mm) | — | — | 17.80 | 15.70 | 4.38 | 2.63 |

TABLE 19

Correlation with single slice at different true anatomic locations.

| Anatomic slice location | Correlation with single slice | |
| --- | --- | --- |
|  | SAT | VAT |
| T10-T11 | 0.85 | 0.79 |
| T11-T12 | 0.87 | 0.81 |
| T12-L1 | 0.88 | 0.90 |
| L1-L2 | 0.88 | 0.89 |
| L2-L3 | 0.85 | 0.92 |

TABLE 19-continued

Correlation with single slice
at different true anatomic locations.

| Anatomic slice location | Correlation with single slice | |
|---|---|---|
| | SAT | VAT |
| L3-L4 | 0.76 | 0.92 |
| L4-L5 | 0.74 | 0.87 |

Examining the top two rows derived from linear mapping for SAT and VAT in FIG. 21, it is observed that the anatomic locations of maximum correlation are significantly different for different subjects. Yet, for the non-linear mapping, for both SAT and VAT, the anatomic locations of maximum correlation are much closer even though they come from different subjects. In particular, for the non-linear mapping, there appears to be relatively constant high correlation values for SAT in the lower thoracic/upper abdominal region and for VAT in the lower abdomen.

Figure 22:
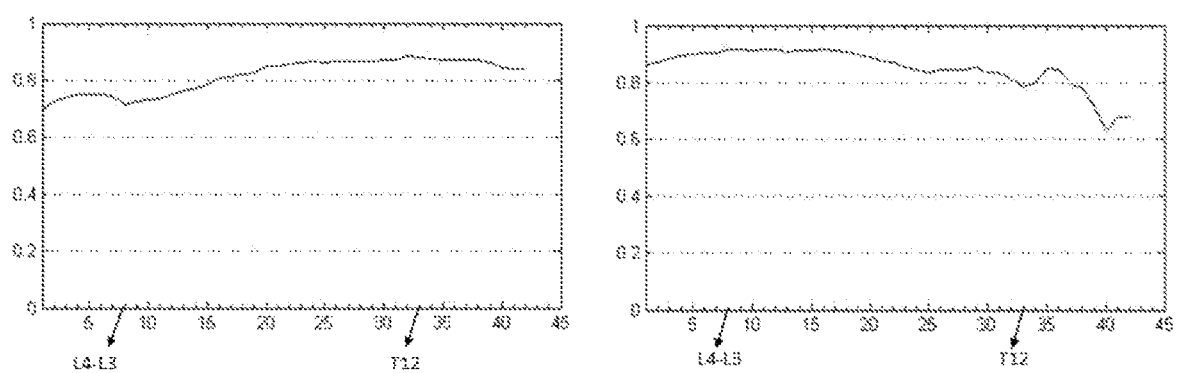
FIG. 22 illustrates correlation curves from non-linear mapping derived from a calibration data set different from that used in FIG. 19. Left: SAT; Right: VAT. The vertical axis shows the correlation value. The horizontal axis shows the location of image slices (Slice 1 is at the inferior most position). Some key landmark positions are indicated along the horizontal axis.

To test the sensitivity of the results to the choice of the calibration data set, FIG. 22 shows the single-slice correlation curves for SAT and VAT derived from a different set of randomly chosen 5 calibration data sets. The maximum correlation achieved was again 0.88 and 0.91 for SAT and VAT, respectively, which are the same as the results in FIG. 19, and the slice locations where fat volume maximally correlated with fat area are also the same. The curves are remarkably similar, as expected, except for some minor differences at the ends of the curves. Compared with linear mapping and earlier methods, one advantage of the proposed non-linear mapping approach is to guarantee that the slice where maximum correlation occurs is at the same anatomical location irrespective of patient-to-patient anatomical variability.

Correlation with Multiple Slices

To address the question as to whether single slice or multiple (contiguous or non-contiguous) slices yield better area-to-volume correlation, the inventors calculated the correlation by using multiple slices with both linear and non-linear mappings.

TABLE 20

Correlation by using one or more slices per subject,
where correlations shown are maximum
values for the two mapping techniques.

| Multiple slices | | 1 slice | 2 slices | 3 slices |
|---|---|---|---|---|
| Linear mapping | SAT | 0.89 | 0.90 | 0.91 |
| | VAT | 0.81 | 0.84 | 0.85 |
| Non-linear mapping | SAT | 0.88 | 0.88 | 0.89 |
| | VAT | 0.92 | 0.95 | 0.95 |
| Slices at L4-L5 | SAT | 0.74 | 0.74 | 0.75 |
| | VAT | 0.87 | 0.88 | 0.89 |

Table 20 lists the maximum correlation achieved by using one, two, and three slices per subject with linear and non-linear mapping. The correlation derived from the slice at the L4-L5 junction is also listed for comparison since this location is most commonly used. For this case, the choice of 2 and 3 slices is such that the slices are contiguous and they are as close to the L4-L5 junction as possible. Note that non-linear mapping with multiple slices achieved the highest correlation. Table 21 lists anatomic locations where maximum correlation is achieved for the two methods. Slice locations are shown after mapping (linear and non-linear) where the maximum correlation is achieved. The values listed in the table are the slice numbers in the volume files (where number 1 indicates the bottom slice of the abdominal region and larger numbers are located closer to the top of the abdominal region). The anatomic locations in SAS are also listed for the non-linear mapping. The locations of maximum correlation for SAT and VAT are again different, and the multiple slices achieving maximum correlation are not contiguous. For non-linear mapping, the sites in the standardized anatomic space where maximum correlation is achieved are also listed in Table 21. One possible explanation for the findings is that discontinuous slice location combination may allow for a more representative sampling of the average fat area per slice across the abdominal region (vs. the scenario where all the slices are from contiguous slices through the abdomen).

TABLE 21

| | | 1 Slice | 2 Slices | 3 Slices |
|---|---|---|---|---|
| Linear mapping | SAT | 36 | 27, 53 | 26, 52, 54 |
| | VAT | 25 | 4, 27 | 3, 25, 29 |
| Non-linear mapping | SAT | 33 (T12) | 22, 37 (L1-L2, T11) | 22, 33, 35 (L1-L2, T12, T11-T12) |
| | VAT | 8 (L3-L4) | 8, 36 (L3-L4, T11) | 8, 16, 36 (L3-L4, L1-L2, T11) |

Figure 23:
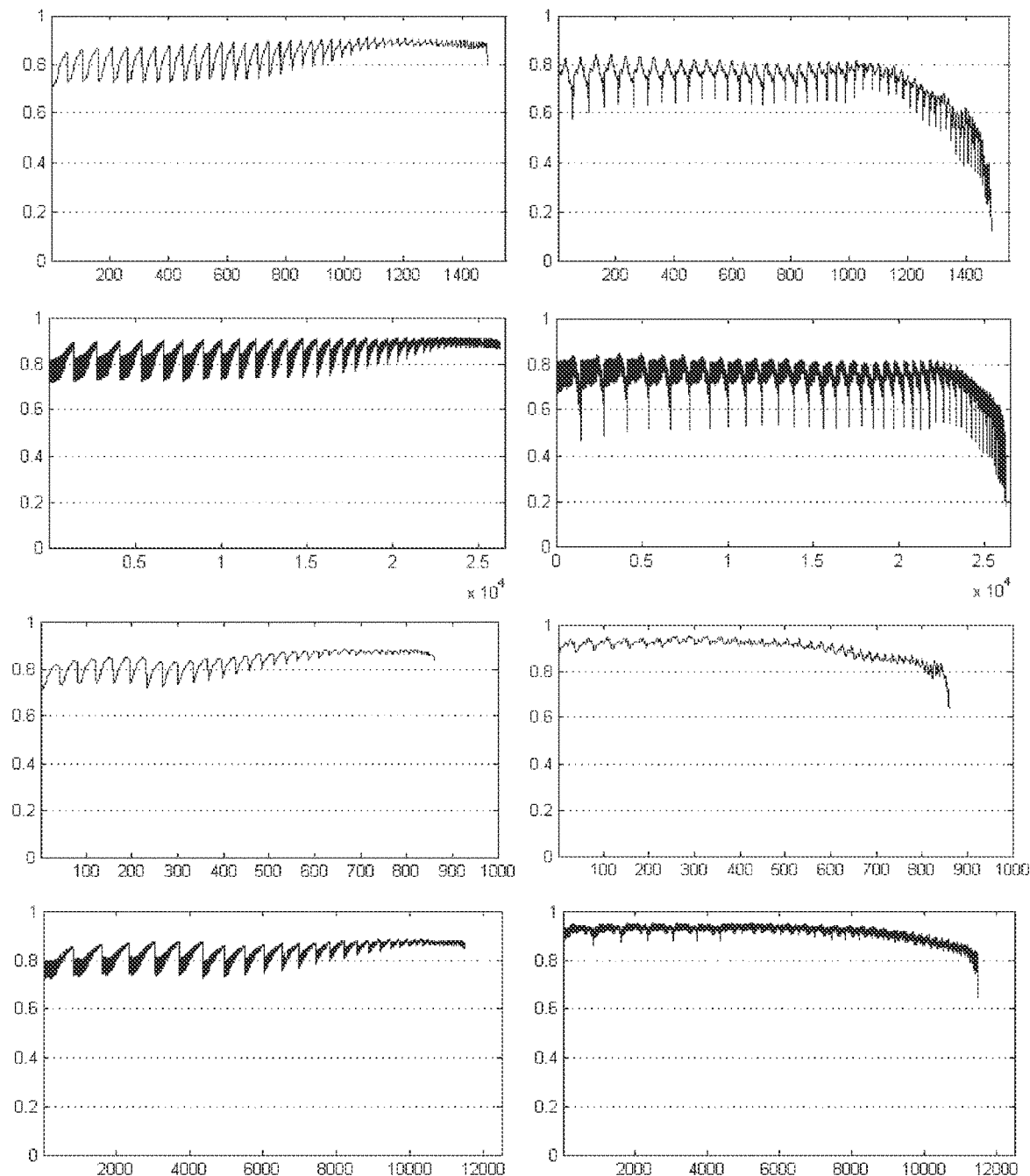
FIG. 23 illustrates correlation curves from linear and non-linear mapping. Rows 1 and 2: SAT (left) and VAT (right) results for linear mapping using 2 and 3 slices. Rows 3 and 4 are similarly for non-linear mapping. The vertical axis shows the correlation values and the horizontal axis shows the combination number for the different combinations among all possible choices of 2 and 3 slices. The oscillations seen are due to the systematic pattern of multiple slice number combinations.

FIG. 23 shows the correlation curves when multiple slices are used for correlation calculation. Here, only the results using 2 and 3 slices are shown since single slice results have been shown above. From FIGS. 19 and 23 one skilled in the art will observe that higher maximum correlation can be achieved when more slices are used for correlation calculation. The maximum correlation for VAT derived from non-linear mapping is substantially (10%) greater than that from linear mapping as shown in Table 20. Especially note that the correlation curves for VAT go down considerably for certain combinations of 2 and 3 slices for linear mapping. This is due to the fact that the multiple slices are in fact from much different anatomic locations among subjects as in the single-slice case, while the non-linear method performs much better since slices are selected anatomically more accurately in the standardized anatomic space.

Observations

Correlation analysis to determine the optimal anatomic slice locations in the abdomen for estimating body fat has not previously been performed. The inventors have found that the optimal anatomic slice locations for single-slice SAT and VAT estimation are not the same, contrary to common assumption. This result is important since these fat components may have different effects upon the pathophysiology of different disease processes. Use of multiple slices can achieve higher correlation than use of a single slice. The optimal locations of slices in this latter case are not contiguous. Experimental results on 50 abdominal CT image data sets showed that the standardized anatomic space created through non-linear mapping of slice locations achieves better anatomic localization than linear mapping. The method of the invention can be extended with greater or fewer landmarks than those adopted herein. The method has been illustrated by using CT image data sets, though the inventors will continue to explore the applicability of this method on MR image data sets in the future.

Overall, one skilled in the art will appreciate the following from the above detailed description of the methods of abdominal fat quantification in accordance with the invention:

1. The maximum area-to-volume correlation achieved is quite high, suggesting that it may be reasonable to estimate body fat by measuring the area of fat from a single anatomic slice at the site of maximum correlation. However, the site of maximum correlation and the degree of correlation itself may both depend on the particular patient group or disease condition studied. This disclosure focused on (near) normal male subjects in the age group of 50-60 years.

2. The site of maximum correlation is not at L4-L5 as commonly assumed, but is more superiorly located at T12-L1 for SAT and at L3-L4 for VAT. Furthermore, the optimal anatomic locations for SAT and VAT estimation are not the same, contrary to common assumption.

3. It is important to make sure that the slices for different subjects are selected at the same anatomic locations for correlation analysis. These locations seem to vary non-linearly from subject to subject, at least for the population (G) and body region (B) considered herein. The standardized space mapping achieves this consistency of anatomic localization by accurately managing non-linearities in the relationships among landmarks. The dependence of VAT on the precision of anatomic localization seems to be far greater than that of SAT, perhaps due to the complex shape of the distribution of VAT compared to SAT.

Multiple slices achieve greater improvement in correlation for VAT than for SAT. The optimal locations of slices are not contiguous.

The method of abdominal fat quantification in accordance with the methods of the invention thus help one skilled in the art to find optimal location(s) of slices for any given patient group and body region utilizing the data sets under any given image modality. Once the optimal locations are determined in the manner demonstrated herein, actual acquisition of images at precisely those locations in clinical practice can be implemented without much difficulty by making appropriate changes to the scan protocol, for example by marking off plane locations on scout views.

One drawback of the described methods is that it is difficult to implement on MR images since it is quite challenging to segment vertebral bodies in MR images. However, if certain features to tag anatomic locations reliably can be identified on slice images, then the method can be implemented in a straightforward manner.

EXAMPLE 2: AUTOMATIC LOCALIZATION OF IASLC-DEFINED MEDIASTINAL LYMPH NODE STATIONS ON CT IMAGES USING FUZZY MODELS

Materials and Methods

The image data sets utilized for this study were 45 routine contrast-enhanced chest CT examinations collected from the patient image database of the University of Pennsylvania health system. Subjects were male patients with an average age of 54.7±3.9 years. The images included were considered to be radiologically near normal by a board-certified radiologist (DAT). The CT examinations had been performed on 16 or 64 multi-detector row CT scanners (Siemens Medical Solutions, Malvern, Pa.) during a full inspiratory breath-hold and during the venous phase of enhancement following intravenous contrast administration. Each examination consisted of an average of 60 axial slices covering the entire thorax, with a pixel size of 0.77 mm×0.77 mm and a slice spacing of 5 mm. For model building and training, image data sets from 23 subjects were used, and the remaining 22 image data sets were utilized for testing the recognition method.

The AAR lymph node (AAR-LN) system utilizing the methods of the invention is comprised of two parts: model building and automatic recognition of the stations.

Model Building

The building of fuzzy models consists of three main processes: (a) gathering the image database, (b) delineating each nodal station on each 3D image to indicate the 3D region occupied by the station, and (c) constructing fuzzy models. Part (a) has been described in the aforementioned articles of Udupa et al. Part (b) describing how the regions were defined and how the delineation was implemented is presented below. Part (c) utilizes the same algorithms as used previously by the inventors for fuzzy modeling of anatomic organs, which take as input the delineated binary images of all samples of all organs for the population and output a hierarchical fuzzy anatomy model of the body region as described above with respect to the AAR system. In the present embodiment, the organs are replaced by the different mediastinal lymph node stations.

Delineating Lymph Node Stations

Figure 24:
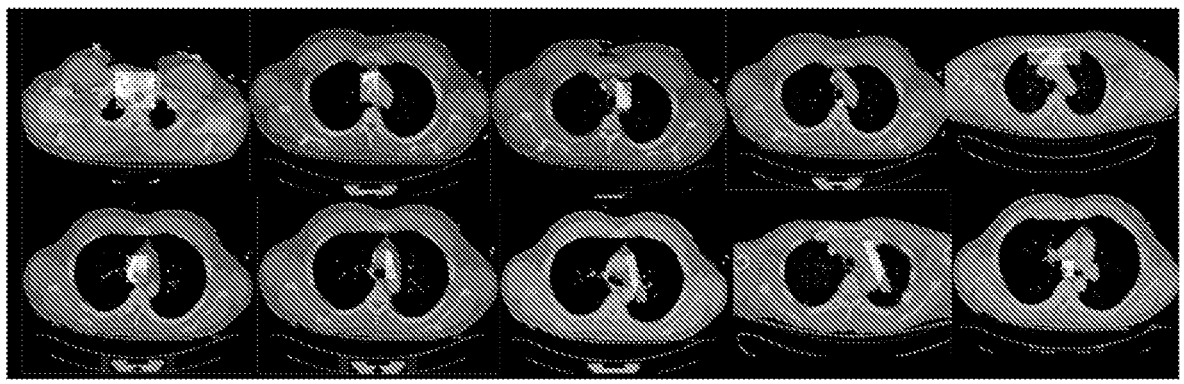
FIG. 24 illustrates examples of the mediastinal lymph node stations delineated on axial CT slices from one study (Top row: Stations 1, 2R, 2L, 3p, 3a; Bottom row: Stations 4R, 4L, 5, 6, 7).
Figure 25:
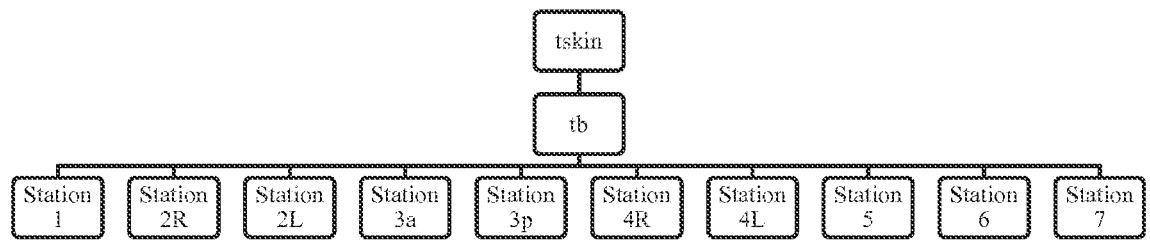
FIG. 25 illustrates hierarchy $H_A$ for automatic recognition, where $H_A$ has the thoracic skin (tskin) object as root and trachea and bronchi (tb) as offspring of tskin and parent of all stations.

Each lymph node station was defined consistently according to the thoracic anatomic landmarks, generally as a 3D hexahedral object. The location and orientation of the faces of the hexahedron were defined in the anterior (A), posterior (P), right (R), left (L), superior (S), and inferior (I) aspects. An illustration of the CT images and the delineated lymph node stations is shown in FIG. 24. The stations were manually outlined according to a modified version of the IASLC definitions by trained specialists under the supervision of a board-certified radiologist (DAT). The modifications of the IASLC were necessary to make the specifications fully defined in terms of image features so as to facilitate its implementation and for handling situations where boundaries were ill-defined by a 2009 proposal for a lymph node map for lung cancer (Ichimura et al., "Caudal border of level 2R in the new international lymph node map for lung cancer," Journal Thoracic Oncology, Vol. 5 No. 4, April, 2010, pp. 579-80 (2010)). Station I was adapted to the lower cervical region in the study as the full cervical region was not completely imaged on the standard chest CT examinations. In Table 22 below, the inventors present the regions that define the nodal stations, and their respective anatomical landmarks as used in the inventors' implementation.

TABLE 22

Description of the mediastinal lymph node stations via boundary definitions of the hexahedron, with the planes that define the hexahedral faces in the anterior (A), posterior (P), right (R), left (L), superior (S), and inferior (I) aspects.

| Region | Definition | Region | Definition |
| --- | --- | --- | --- |
| Station 1 Partial of Low Cervical/ Supra- | A: Plane between anterior clavicles (*) P: Anterior aspect of spine (*) R: Lateral tip of right transverse process of spine (*) | Station 4R Right Lower Para- | A: Anterior wall of superior vena cava or origin of left common carotid artery (whichever is more anterior) (*) P: Posterior wall of trachea (*) |

TABLE 22-continued

Description of the mediastinal lymph node stations via boundary definitions of the hexahedron, with the planes that define the hexahedral faces in the anterior (A), posterior (P), right (R), left (L), superior (S), and inferior (I) aspects.

| Region | Definition | Region | Definition |
| --- | --- | --- | --- |
| clavicular Nodes | L: Lateral tip of left transverse process of spine (*)<br>S: Lung apices (*)<br>I: Superior aspect of manubrium (*) | tracheal Nodes | R: Right pleural sac (*)<br>L: Left wall of trachea<br>S: Axial level/plane where the inferior aspect of left brachiocephalic (innominate) vein crosses anterior to the left side of the trachea (*)<br>I: Inferior aspect of horizontal portion of azygos vein |
| Station 2R<br>Right Upper Paratracheal Nodes | A: Anterior wall of superior vena cava or origin of left common carotid artery (whichever is more anterior) (*)<br>P: Posterior wall of trachea (*)<br>R: Right pleural sac (*)<br>S: Superior aspect of manubrium (*)<br>I: Superior aspect of aortic arch | Station 4L<br>Left Lower Para-tracheal Nodes | A: Anterior wall of superior vena cava or origin of left common carotid artery (whichever is more anterior) (*)<br>P: Posterior wall of trachea (*)<br>R: Left wall of trachea<br>L: Oblique plane along left wall of aortic arch (*)<br>S: Superior aspect of aortic arch<br>I: Superior aspect of left main pulmonary artery |
| Station 2L<br>Left Upper Paratracheal Nodes | A: Anterior wall of superior vena cava or origin of left common carotid artery (whichever is more anterior) (*)<br>P: Posterior wall of trachea (*)<br>R: Left wall of trachea<br>L: Left pleural sac (*)<br>S: Superior aspect of manubrium (*)<br>I: Superior aspect of aortic arch | Station 5<br>Subaortic Nodes | A: Anterior wall of superior vena cava or origin of left common carotid artery (whichever is more anterior) (*)<br>P: Posterior aspect of aortic arch (*)<br>R: Oblique plane along left wall of aortic arch (*)<br>L: Left pleural sac (*)<br>S: Superior aspect of aortic arch<br>I: Superior aspect of left main pulmonary artery |
| Station 3a<br>Prevascular Nodes | A: Posterior wall of sternum<br>P: Anterior wall of superior vena cava or origin of left common carotid artery (whichever is more posterior) (*)<br>R: Lateral tip of a thoracic spinal right transverse process +2 cm (*)<br>L: Lateral tip of a thoracic spinal left transverse process +2 cm (*)<br>S: Superior aspect of manubrium (*)<br>I: Carina | Station 6<br>Para-aortic Nodes | A: Anterior aspect of aortic arch (*)<br>P: Posterior aspect of aortic arch (*)<br>R: Oblique plane along left wall of aortic arch (*)<br>L: Left pleural sac (*)<br>S: Superior aspect of aortic arch<br>I: Inferior aspect of aortic arch |
| Station 3p<br>Retrotracheal Nodes | A: Posterior wall of trachea<br>P: Anterior aspect of spine (*)<br>R: Right wall of trachea (*)<br>L: Left wall of trachea (*)<br>S: Superior aspect of manubrium (*)<br>I: Carina | Station 7<br>Subcarinal Nodes | A: Plane along anterior wall of mainstream bronchi<br>P: Plane along anterior aspect of the thoracic spine<br>R: Left wall of right bronchi (*)<br>L: Right wall of left bronchi (*)<br>S: Carina<br>I: Inferior aspect of bronchus intermedius (on right) and superior aspect of left lower lobe bronchus (on left) (whichever is the most inferior) (*) |

(*) Modified from or added to the original IASLC definitions [1] for consistency and for enabling actual computer implentation.

Constructing Fuzzy Models:

The fuzzy anatomic model, FAM(B), of the stations in the thoracic body region B, is defined to be a quintuple FAM (B)=(H, M, ρ, λ, η), where H is a hierarchical order considered in FAM(B) for the organs and stations in B; M is a set fuzzy models $FM(O_l)$, one model for each organ/station $O_l$; ρ describes the position and orientation relationships, and their variations, between each offspring object $O_k$ and its parent $O_l$ in the hierarchy; λ is a family $\{\lambda_l: 1 \leq l \leq L\}$, where each $\lambda_l$ expresses the variation in scale factor (size) of organ/station $O_l$ over its population; and η represents the statistics of a set of measurements pertaining to the organ/station assembly in B. Details on model building are described by above in the description of the AAR system.

Automatic Recognition of Organs and Lymph Node Stations

The inventors have experimented with automatic recognition, with hierarchy $H_A$. The hierarchy is displayed in FIG. 25; $H_A$ has the thoracic skin (tskin) object as root and trachea and bronchi (tb) as offspring of tskin and parent of all stations. For the recognition process, the inventors used two different methods: thresholded optimal search and the one-shot method as described above in the description of the AAR system. As described therein, the thresholded optimal search algorithm refines object pose by an optimal search based on thresholding the test image. The one-shot method uses knowledge embedded in FAM(B) to recognize the different objects. The inventors combined both methods in a mixed strategy, with part of recognition done by using thresholded optimal search (for the objects tskin, tb and rs) and others by using the one-shot strategy (stations).

Evaluation

To evaluate recognition performance, the inventors used two metrics: distance error and scale ratio. Distance error is the distance between the geometric centers of the known true object and the fuzzy model at the time of recognition. Scale ratio is the size of the estimated model divided by the size of the true object. Object size is measured by the square root of the sum of the cigenvalues where the eigenvalues result from principal component analysis of the object.

Results

Figure 26:
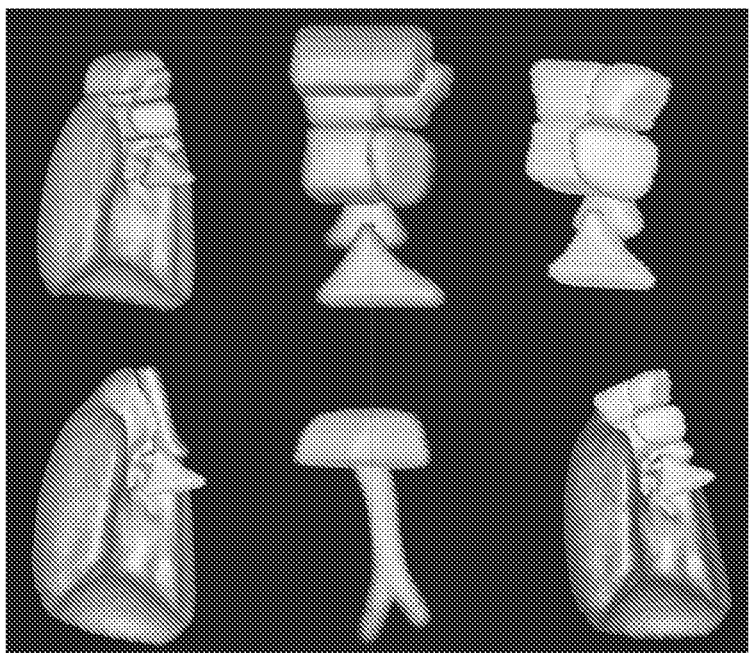
FIG. 26 illustrates volume rendered displays of the generated fuzzy models showing stations 1, 2 (2R, 2L), 3p, 4 (4R, 4L), and 7 and fuzzy models of the right pleural space (rps) and trachea & bronchi (tb) for anatomic context (Top row (L to R): [rps, stations 1, 2R, 2L, 3p, 4R, 4L, and 7], [stations 1, 2R, 2L, 3p, 4R, 4L, and 7], [stations 2R, 2L, 3p, 4R, 4L, and 7]; Bottom row (L to R): [rps, stations 3p and 7], [station 1 and tb], [rps, stations 2R, 2L, 3p, 4R, 4L, and 7]).

FIG. 26 depicts volume renditions of the fuzzy models of several stations and organs constructed from 23 of the 45 image data sets. The remaining 22 data sets were used for testing the recognition process.

Figure 27:
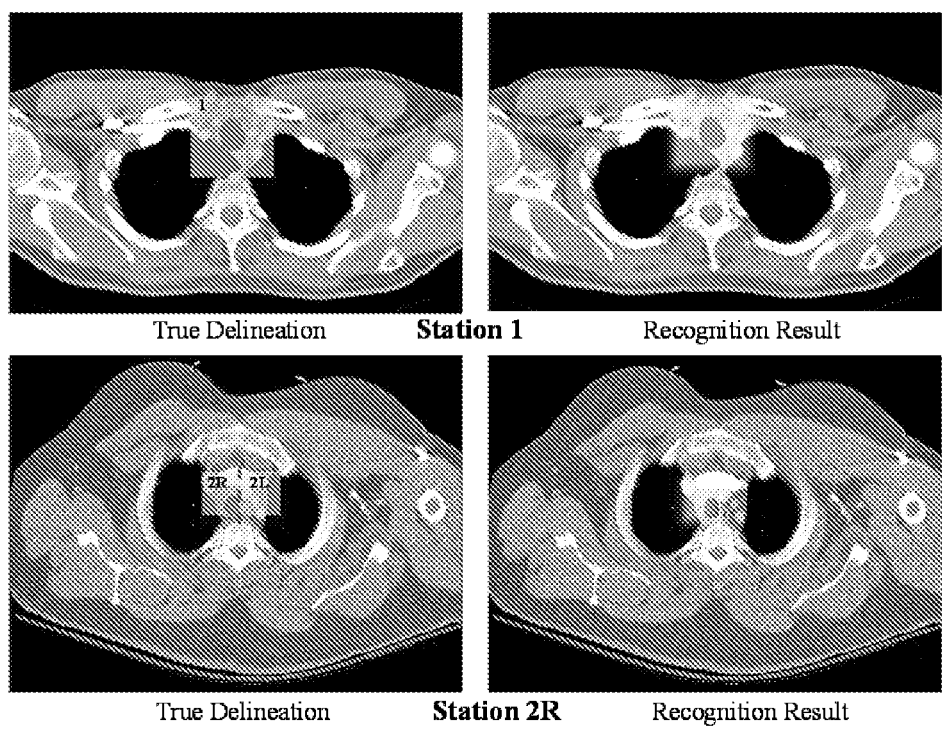
FIG. 27 illustrates recognition results for three stations by overlaying the cross section of the fuzzy model at recognition on a slice of the test image. The true delineation of the stations is also displayed for reference on the corresponding slice.

In FIG. 27, the inventors display recognition results for three stations by overlaying the cross section of the fuzzy model at recognition on a slice of the test image. The true delineation of the stations is also displayed for reference on the corresponding slice.

In Table 23, the inventors present the recognition results for the different hierarchies. The results shown are the mean position error (in mm) for each object and scale ratio, respectively. In Table 23, one can observe that the anatomic organs (tskin, tb and rs) have mean errors from 5.27 to 7.13 mm. These values are comparable to the 5 mm spacing between slices, and are excellent results for automatic recognition. For recognition of the nodal stations, the location error ranges from 6.91 mm to 34.24 mm. Noting that the voxel size is limited by slice spacing, these errors expressed in terms of voxels are in the range of 1 to 6 voxels. Some stations such as #4R and #4L have a mean error of 7.55 mm and 6.91 mm, which is around 1 voxel. For station localization, the inventors believe that these results are excellent. The estimated scale ratio in the automatic recognition is perfect for tskin (1.00) and slightly underestimated for tb (0.90). The scale ratio for the nodal stations follows the ratio of the parent object, where the stations have a size ratio of around 0.90.

node stations on images subjectively, particularly since not all boundaries (superior, inferior, anterior, posterior, right, and left) are precisely defined for each of the lymph node stations. At present, to the inventors' knowledge, no method exists to assist radiologists during image interpretation to automatically identify and indicate IASLC lymph node stations on cross-sectional imaging. The inventors believe that when the AAR-LN system is implemented on dedicated workstations, the acceptance of the IASLC standard and the consistency of its interpretation will be greatly facilitated, not just for CT imaging assessment, but potentially also for magnetic resonance imaging (MRI), positron emission tomography (PET) imaging, and hybrid modalities such as PET/CT and PET/MRI for imaging assessment of the thorax. The inventors note, however, that other standards besides the IASLC standard may be readily used by those skilled in the art without departing from the teachings of the invention.

TABLE 23

Mean position error and standard deviation (in mm) and mean scale ratio.

| | | | Station | | | | | | | | | |
|---|---|---|---|---|---|---|---|---|---|---|---|---|
| Metric | Tskin | Tb | 1 | 2R | 2L | 3a | 3p | 4R | 4L | 5 | 6 | 7 |
| Distance error (std) [mm] | 5.27 (2.51) | 7.13 (5.20) | 17.02 (7.06) | 11.73 (6.73) | 18.51 (9.18) | 11.79 (7.70) | 9.73 (6.10) | 7.55 (2.88) | 6.91 (3.47) | 13.95 (5.96) | 34.24 (7.69) | 13.77 (4.55) |
| Scale ratio | 1.00 | 0.90 | 0.81 | 0.90 | 0.85 | 0.87 | 0.88 | 0.88 | 0.85 | 0.85 | 0.87 | 0.95 |

Observations

The automatic recognition of lymph node stations is a challenging problem. The proposed approach involves two main steps of AAR: fuzzy model building and object recognition. Definition of the lymph node stations was performed consistently and refined for computational specificity in order to obtain reliable computational fuzzy models. The recognition method was based on the one-shot and thresholded optimal search algorithms described above in the description of the AAR system. The results presented here are preliminary but indicate the potential utility of the AAR approach, originally designed for recognizing and delineating anatomy in medical imagery, adapted for automated lymph node station definition and localization. The results indicate that localization of thoracic nodal stations within 1-3 voxels is feasible for a majority of the tested stations. Considering the ambiguity (and fuzziness) that exists in the expert perception of the nodal stations, these results seem to be excellent.

The hierarchy used with the fuzzy anatomy model can impact the results considerably. The inventors are investigating this observation, especially keeping in mind the challenges offered by nodal stations 2R, 2L, and 6. Understanding the relationship among the objects of the thoracic region and lymph node stations as to which relationships are less variable over the patient population may allow the inventors to devise optimal hierarchies with improved recognition accuracy in the future.

While the IASLC formulation is helpful to standardize interpretation and reporting of lymph node disease conditions, it leaves the radiologist with the arduous task of following the detailed specifications and finding the lymph

EXAMPLE 3: USE OF AAR FOR RADIOTHERAPY PLANNING

The AAR approach described above is a significant departure from state-of-the-art segmentation methodologies in the following key considerations:

(1) Fuzzy modeling: All reported model-based approaches have a statistical framework, none taking a fuzzy approach. Fuzzy set concepts have been used extensively otherwise in image processing and visualization. The AAR approach allows bringing anatomic prior information in an all-digital form into graph-based object delineation and recognition algorithms (such as fuzzy connectedness and graph cuts) without having to make "continuous" assumptions on matters such as shapes and random variables and their nature, density distribution, and independence, etc. They also allow capturing information about uncertainties at the patient level (e.g., blur, partial volume effects) and population level, and codification of this information within the model.

(2) Prior information encoding: The AAR methodology takes a novel approach to gathering and encoding in an optimal hierarchical manner very detailed prior information about individual objects and their relationship to other objects, more globally as well as in their neighborhood. This information has a direct bearing on object recognition/localization and delineation. This codification permits gradual refinement starting from conspicuous global information to more subtle local details.

(3) Numerousness of objects, generality of AAR: The AAR approach can handle all major organs in a body region, and is applicable to different body regions, and even image modalities. This generality allows rapid prototyping for a new application for the same body region, involving the same or different image modality. The extensive object-level knowledge that the AAR approach exploits at various stages for recognition and delineation is challenging to incorporate in prior art atlas-based methods and methods that rely on smooth spatial deformations and transformations.

then express the desire of arranging objects in an optimal hierarchy. One possible form for cost is as a function of the spatial and intensity nearness of x and y—very near on both counts should imply high cost. If x is much larger in size than y and if both are similar in image intensity, then x is far less influenced by y during y's localization than vice versa and hence asymmetry of the cost function.

TABLE 24

Figure 28:
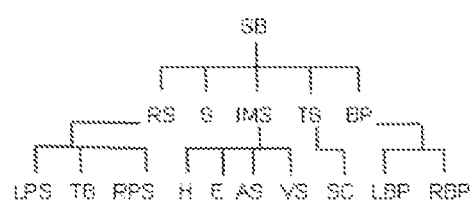
FIG. 28 illustrates a generalized anatomic hierarchy for the thoracic region.
Figure 29:
FIG. 29 illustrates the use of a superset instead of a precise boundary when modeling sparse objects such as the trachea and bronchi or esophagus.

Acronyms used for thoracic objects; see FIG. 28

| SB | Skin Boundary | RS | Respiratory System = LPS + RPS + TB | TS | Thoracic Skeleton | VS | Venous System (main trunks only) |
|---|---|---|---|---|---|---|---|
| LPS | Left Pleural Space | BP | Brachial Plexus | H | Heart | SC | Spinal Cord |
| RPS | Right Pleural Space | S | Stomach | E | Esophagus | LBP | Left Brachial Plexus |
| TB | Trachea & Bronchi | IMS | Internal Mediastinum | AS | Arterial System (main trunks only) | RBP | Right Brachial Plexus |

Using the AAR methodology described herein for radiotherapy planning will shift current clinical practice by facilitating advanced RT methods such as IMRT/PBRT. The clinical benefits of adaptive planning have been well established in improving tumor radiation dosing and reducing dose to normal adjacent structures for head and neck and lung cancers. Despite promising findings showing less toxicity and greater sparing of organs at risk with adaptive planning for use of PBRT for non-small cell lung carcinoma (NSCLC), there is limited momentum in the field to use adaptive planning since it remains highly labor-intensive and impractical to deliver. The AAR approach described herein can be used to dramatically reduce contouring time, making adaptive re-planning much more feasible, facilitating its wide-spread clinical use.

Step 1: Build Hierarchical Fuzzy Anatomy Models (FAMs) of the Region of Interest As noted above, a Fuzzy Anatomy Model of a body region B for a group G, FAM(B, G), is defined as a quintuple: FAM(B, G)=(H, M, ρ, λ, η). H here denotes a hierarchy, represented as a tree, of the objects in B. As noted above, AAR uses anatomic hierarchies, an example of which is shown in FIG. 28. Methods are used in accordance with the methods of the invention to automatically construct a hierarchy that is optimal for object recognition, as explained below. Variable M={FM($O_k$): k=1, ..., L} is a set of fuzzy models, with one model FM($O_k$) per each object $O_k$. For constructing FM($O_k$) the inventors first convert all existing contour data into 3D binary images. Then the inventors follow the above-described approach of codifying as fuzzy membership values the manner in which the different samples of $O_k$ vary spatially over group G from an ideal homothetic affine transformation, while also retaining the spatial relationship among objects in the hierarchical order. Variable ρ describes the parent-to-offspring relationship in H over G in both position and orientation. Variable λ is a set of scale factor ranges indicating the size variation of each object $O_k$ over G. Variable η represents a set of measurements describing the morphology, shape, and image intensity properties of the objects in B over G. FAM(B, G) is then enhanced from this basic form in two ways as described below.

Optimal hierarchies: Consider a directed graph whose nodes are the 16 thoracic objects of Table 24 and in which every pair of objects is connected by a directed arc. Suppose a cost is assigned to each directed arc (x, y) that indicates how undesirable it is to have object x as the parent of y in the hierarchy. An optimal spanning tree for the graph will Sparse object modeling: Sparse objects (such as trachea & bronchi—TB, esophagus—E) are challenging to model because small subject-to-subject variations in their form (e.g., the descending aorta portion of the arterial system (AS) being wavy versus straight) can lead to ill-defined models. This is true for all model-based approaches. The inventors propose to employ rough sets to construct fuzzy models FM($O_k$) for all sparse objects $O_k$. The basic idea is as follows. Instead of using the precise boundary of the object in each training sample, a superset containing the region of the object is used (see FIG. 29). The supersets are defined carefully so that they are as small as possible, their variability over G is as small as possible, and they do not interfere with other nearby objects. The rest of the fuzzy model building process then will proceed as above using the supersets instead of the real object contours.

Step 2: Algorithms for the Automatic Localization and Delineation of Thoracic Objects The AAR object recognition/localization procedure uses the model built in Step 1 and follows the procedure for AAR-R set forth above. Procedure AAR-R proceeds hierarchically in H. It finds the root object first (by calling R-ROOT) and subsequently localizes the offspring objects (by calling R-OBJECT) in a breadth-first order by combining optimally the prior information in FAM(B,G) with the information in the given image I. Different algorithms may be chosen for R-ROOT and R-OBJECT. Several such algorithms may be used, including the one-shot method, ball-scale strategy, Fisher Linear Discriminant, and Thresholded Optimal Search method. Among these, the Thresholded Optimal Search method described above is the top performer.

Methods for delineating objects require the above recognition results as the starting point. The inventors have chosen to base delineation methods on the Iterative Relative Fuzzy Connectedness (IRFC) engine since IRFC is extremely fast, completing segmentation of very large objects (5123) within 5 seconds. It is provably robust to seed set location and size, requires very few seeds, and is naturally adaptable to prior information encoded in the form of fuzzy models. Lastly, even when an object has poorly defined boundaries, it produces effective segmentations when co-object components are properly identified through seeds. Four extensions to the basic algorithm may also be provided as follows: (i) For each object, its topological neighbors will be determined and this anatomic information, encoded in FAM(B,G), is used for automatically specifying seeds for object and co-object components from knowledge of the recognition results for these components. (ii) For each object and its neighbors, their component tissues are identified and their characteristics (mean and standard deviation), determined from the training data sets, are encoded into FAM(B,G). This information is used for automatically and optimally specifying the fuzzy affinity, which forms the core of the IRFC (and any FC) engine. (iii) A fuzzy model component of affinity is designed to bring prior information seamlessly into the IRFC framework. (iv) The spatial, intensity-homogeneity-based, tissue-specific, and the model components of affinity are integrated into TRFC for a globally optimal separation of object and co-object components.

For segmenting images corresponding to different treatment fractions, the effectiveness of propagating recognition results from the previous fraction to the next for initializing recognition and delineation processes is also considered since the changes from fraction to fraction are usually not as much as variations found in the same object, with or without abnormalities, over a patient population.

The AAR methodology has the following strengths and unique features which set it apart from state-of-the-art object localization and delineation methods: (1) It starts with a precise and consistent definition of each body region and all major objects in each body region, which is then implemented in the AAR system. (2) Its generality has been demonstrated on four body regions—neck, thorax, abdomen, and brain—involving about 40 objects and on CT and MRI. (3) It employs a hierarchical arrangement of objects and encodes within this arrangement the non-linear relationship that exists among objects in their geographical layout and in their size over patient populations. (For example, the size of some objects (such as pericardium) changes much less within a patient group compared to others, and similarly the geometric relationship among objects.) Such detailed prior information is exploited within the hierarchy and in devising "optimal" hierarchies. (4) It integrates naturally the fuzzy modeling and fuzzy connectedness delineation approaches. Because of combinatorial optimization and graph-based methods, this integration results in vastly more efficient algorithms than popular methods in the literature such as those using atlases. (5) It allows rapid prototyping for different applications by modifying the hierarchy to suit the application.

The AAR software system described herein is preferably used for optimized radiation therapy planning in patients with malignancies treated with PBRT or other advanced adaptive RT methods. Those skilled in the art will appreciate that PBRT allows for ultra-precise delivery of treatment due to the physical characteristics of the proton beam and eliminates exit dose received by normal critical structures. However, small changes (on the order of mm's) in anatomy can result in under-dosing of tumor and overdosing of adjacent normal structures. Achieving optimal total dose delivery to the tumor while sparing normal tissue requires accounting for changes in patient anatomy during the course of treatment.

For example, in an exemplary embodiment, the AAR methodology may be used for radiation therapy planning by using the AAR methodology to automate the process of outlining objects and critical organs in the body region that is to receive radiation without the need for recontouring. For this purpose, the AAR methodology is applied to pretreatment images (CT, MRI, etc.) to identify objects and organs in the image and to segment such objects and organs as appropriate. The contours of the objects and organs are then provided as input to the radiation plan. Each time the patient visits for radiation therapy, the process is repeated to ascertain if there has been movement of objects or organs in the body region that is to receive radiation. The system creates a file of the object and organ contours in 3D space and provides such inputs into the radiation treatment planning software. In an alternative embodiment, the system may further show the distribution of a radiation dose simulated on the image having the contour lines for the images simultaneously illustrated so that the therapist may determine, before the dose is applied, whether the radiation dose is likely to impact tissue or an organ outside of the treatment area.

In an exemplary embodiment, the invention provides a computerized method of providing radiation therapy planning in patients receiving radiation treatment by:

(a) building a fuzzy anatomy model of the body region of interest from an existing set of patient images for the body region;

(b) obtaining a pretreatment image of a particular patient body region of interest that is to receive radiation therapy;

(c) using automatic anatomy recognition (AAR) to recognize and delineate objects in the particular patient body region of interest; and (d) providing contours of delineated objects as input to radiation treatment planning software.

Steps (b)-(d) may be repeated prior to respective patient visits for radiation therapy in order to assess changes between visits.

Figure 30:
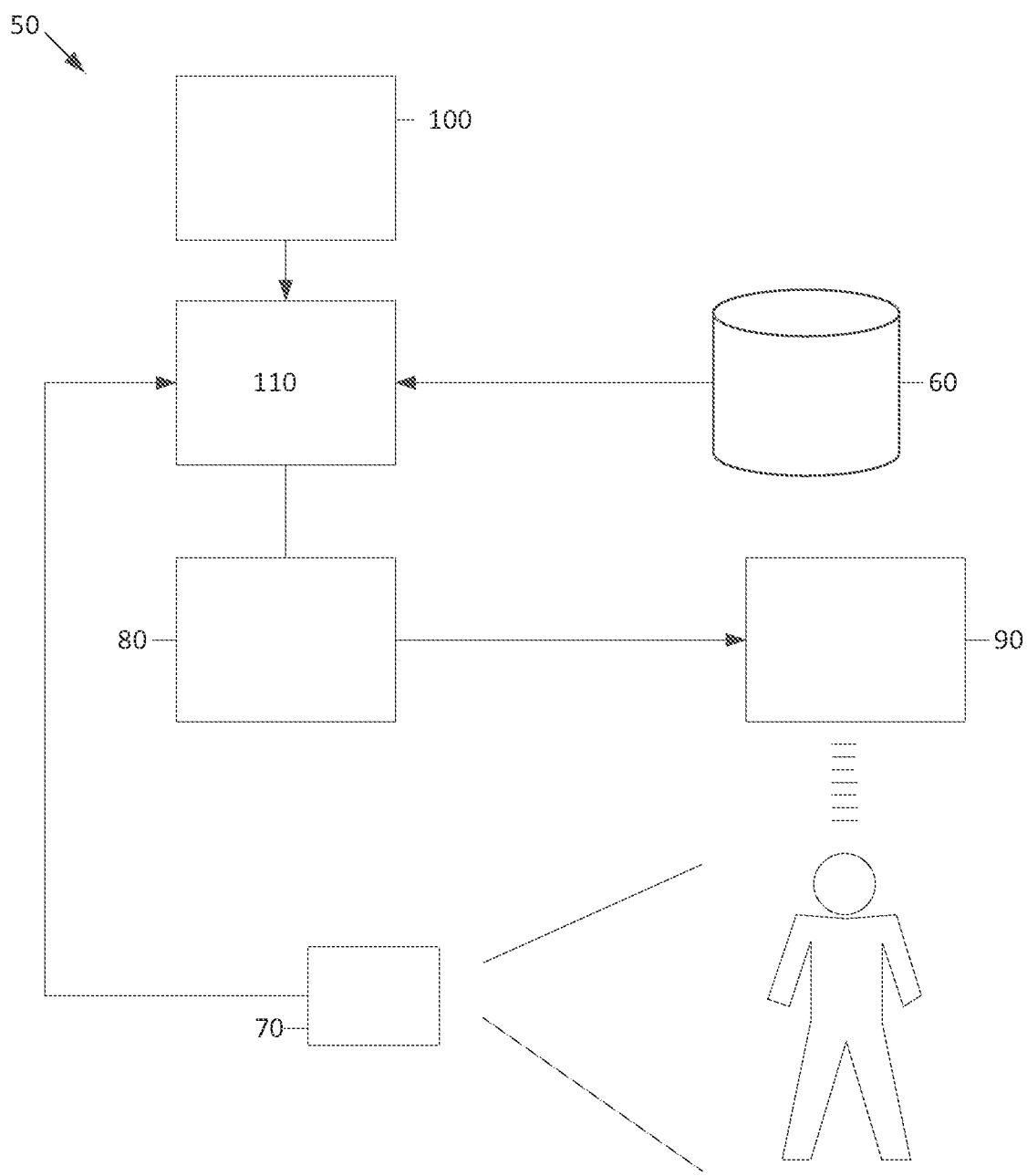
FIG. 30 illustrates a system in accordance with the invention for providing radiation therapy planning in patients receiving radiation treatment.

FIG. 30 illustrates a system 50 that provides radiation therapy planning in patients receiving radiation treatment in accordance with such a method. As illustrated in FIG. 30, the system 50 nominally includes a database 60 that stores image data from patient image sets, an imaging device 70 that obtains a pretreatment image of a particular patient's body region of interest that is to receive radiation therapy, radiation treatment planning software 80 that controls a device 90 for applying radiation to the region of interest, a memory 100 storing computer instructions for implementing the method, and a processor 110 that processes the computer instructions to build a fuzzy anatomy model of the body region of interest from existing patient image sets, to recognize and to delineate objects in the particular patient's body region of interest using automatic anatomy recognition (AAR), and to provide contours of delineated objects as input to the radiation treatment planning software.

Those skilled in the art will appreciate that automating the radiation therapy planning process in this fashion saves time and improves accuracy so as to significantly reduce dosage toxicity and to potentially save a patient's organs and other tissues from the adverse side effects of radiation therapy. Those skilled in the art will further appreciate that this approach may be used with any kind of high energy radiation beam therapies.

It will be appreciated that all of the methods described herein may be implemented in software that operates on a processor that executes instructions stored in a memory component. The processor may include a standardized processor, a specialized processor, a microprocessor, or the like. The processor may execute instructions including, for example, instructions for implementing the methods as described herein. On the other hand, the memory component stores the instructions that may be executed by the processor. The memory component may include a tangible computer readable storage medium in the form of volatile and/or nonvolatile memory such as random access memory (RAM), read only memory (ROM), cache, flash memory, a hard disk, or any other suitable storage component. In one embodiment, the memory component may be a separate component in communication with a processor, while in another embodiment, the memory component may be integrated into the processor. Such non-transitory memory components may be used as a computer readable storage device to store the instructions for implementing the methods and software features described herein.

Those skilled in the art also will readily appreciate that many additional modifications are possible in the exemplary embodiment without materially departing from the novel teachings and advantages of the invention. For example, the techniques of the invention are not limited to CT images but may also be used on other medical imaging modalities such as MRI, ultrasound, PET/CT, etc. Also, the adaptive radiation therapy methods described herein include any such methods known in the art including intensity modulated ratiotherapy (IMRT) and proton beam radiation therapy (PBRT). Accordingly, any such modifications are intended to be included within the scope of this invention as defined by the following exemplary claims.

What is claimed:

1. A computerized method, comprising the steps of:
building a fuzzy anatomy model of a body region of interest from an existing set of patient images for the body region;
obtaining an image of a particular patient body region of interest, wherein obtaining the image comprises mapping slice locations associated with the particular patient body region of interest from a scanner coordinate system to slice locations in a standardized anatomic space;
identifying where a volume-to-area correlation becomes maximal for one or more of an abdomen, a chest, or a neck of the patient;
using automatic anatomy recognition (AAR) to recognize objects in the particular patient body region of interest and to output spatial information associated with the recognized objects; and
delineating, using automatic anatomy recognition (AAR) and based at least on the spatial information associated with the recognized objects, the recognized objects to determine one or more contours or boundaries of the recognized objects.

2. A computerized method as in claim 1, wherein building a fuzzy anatomy model of the body region of interest comprises gathering image data from patient image sets, formulating precise definitions of each body region and organ and delineating them following said definitions, building hierarchical fuzzy anatomy models of organs for each body region, and selecting from the hierarchical fuzzy anatomy models the fuzzy anatomy model of the body region of interest.

3. A computerized method as in claim 2, wherein using AAR to recognize and delineate objects in the body region of interest comprises recognizing and locating organs in the image by employing the hierarchical models, and delineating objects in the body region of interest following a hierarchy of the hierarchical fuzzy anatomy models.

4. A computerized method as in claim 2, wherein object size and positional relationships of objects are specifically encoded into a hierarchy of the hierarchical fuzzy anatomy models and subsequently exploited to recognize and delineate the objects in the body region of interest.

5. A computerized method as in claim 2, further automatically determining an optimal hierarchy for the body region that will yield a best recognition and delineation results.

6. A computerized method as in claim 2, wherein using AAR to recognize objects starts from large, well-defined objects and proceeds down a hierarchy of the hierarchical fuzzy anatomy models in a global to local manner.

7. A computerized method as in claim 1, wherein using AAR to recognize and delineate objects in the body region of interest comprises creating a fuzzy model-based version of an Iterative Relative Fuzzy Connectedness (IRFC) delineation algorithm including an affinity function and a seed specification by integrating fuzzy model constraints into a delineation algorithm used to delineate the objects in the body region of interest.

8. A computerized method as in claim 1, wherein using AAR to recognize and delineate objects in the body region of interest comprises applying a one-shot method to roughly segment an organ and to exclude extraneous information in the image.

9. A computerized method as in claim 1, wherein using AAR to recognize and delineate objects in the body region of interest comprises applying a thresholded optimal search to further refine recognition in the image before recognizing and delineating an object in the body region of interest.

10. A computerized method as in claim 1, wherein the body region includes one or more of a pelvis, a thorax, an abdomen, or a neck region.

11. A computerized method as in claim 1, wherein mapping slice locations from the scanner coordinate system to the standardized anatomic space comprises mapping slice locations of an abdomen to the standardized anatomic space.

12. A computerized method as in claim 1, further comprising estimating body fat of the patient by measuring an area of fat from a single anatomic slice at a site of the maximum volume-to-area correlation and using the single anatomic slice as a marker.

13. A computerized method as in claim 11, further comprising providing slice localization in a patient's image by linear mapping whereby slice locations are linearly mapped from all patients so that a superior-most and inferior-most anatomic slice locations match in a longitudinal direction for all patients.

14. A computerized method as in claim 11, further comprising providing slice localization in a subject's image by nonlinear mapping whereby in addition to a superior-most and an inferior-most location, a plurality of key landmark locations chosen in a longitudinal direction also match for all subjects.

15. A computerized method as in claim 1, wherein the image is an image of a patient's thorax, further comprising automatically localizing lymph node stations in the body region of interest, comprising the steps of:
gathering image data from patient image sets;
manually delineating on the patient image sets various lymph node stations using a standard definition of the lymph node stations;
building at least one hierarchical fuzzy anatomy model of the lymph node stations from the delineations on the patient image sets; and
automatically locating the lymph node stations on the image of the patient's thorax using the at least one hierarchical fuzzy anatomy model.

16. A computerized method as in claim 15, wherein the standard definition of the lymph node stations is based on IASLC standard definitions.

17. A computerized method as in claim 15, wherein automatically locating the lymph node stations further comprises using object recognition algorithms to locate the lymph node stations.

18. A computerized method as in claim 17, wherein the object recognition algorithms comprise a thresholded optimal search algorithm and automatically locating the lymph node stations further comprises using the thresholded optimal search algorithm to refine object pose by an optimal search based on thresholding a test image.

19. A computerized method as in claim 17, wherein locating the lymph node stations comprises using the object recognition algorithms to perform a thresholded optimal search for a first set of objects and a one-shot method to search for a second set of objects.

20. A system, comprising:
- a database that stores image data from patient image sets;
- an imaging device that obtains an image of a particular patient body region of interest, wherein slice locations associated with the particular patient body region of interest are mapped from a scanner coordinate system to slice locations in a standardized anatomic space;
- a memory storing computer instructions; and
- a processor that processes said computer instructions to build a fuzzy anatomy model of the body region of interest from existing patient image sets, uses automatic anatomy recognition (AAR) to recognize and delineate objects in the particular patient body region of interest, and provides contours of delineated objects,
- wherein the processor further processes said computer instructions to identify where a volume-to-area correlation becomes maximal for one or more of a subject's abdomen, chest, or neck.

21. The computerized method as in claim 1, wherein the standardized anatomic space comprises locations of imaging slices associated with anatomic landmarks in a direction perpendicular to the imaging plane of the imaging slices.

* * * * *